(12) United States Patent
Lau et al.

(10) Patent No.: US 10,856,927 B2
(45) Date of Patent: Dec. 8, 2020

(54) TISSUE WELDING AND CUTTING APPARATUS AND METHOD

(71) Applicant: MAQUET CARDIOVASCULAR LLC, San Jose, CA (US)

(72) Inventors: Liming Lau, Mountain View, CA (US); Arnold M. Escano, Santa Clara, CA (US); Jerry Jarrard, Firestone, CO (US); Samuel Ho, Foster City, CA (US); Ryan C. Abbott, San Jose, CA (US); Arthur M. Lin, Fremont, CA (US); Jesse McQuiston, San Carlos, CA (US); Kenny L. Dang, Laguna Niguel, CA (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 385 days.

(21) Appl. No.: 15/482,310

(22) Filed: Apr. 7, 2017

(65) Prior Publication Data

US 2017/0258513 A1 Sep. 14, 2017

Related U.S. Application Data

(60) Division of application No. 14/551,599, filed on Nov. 24, 2014, now Pat. No. 9,636,163, which is a division
(Continued)

(51) Int. Cl.
*A61B 18/04* (2006.01)
*A61B 18/08* (2006.01)
(Continued)

(52) U.S. Cl.
CPC .......... *A61B 18/085* (2013.01); *A61B 17/29* (2013.01); *A61B 18/1445* (2013.01); *A61B 90/03* (2016.02);
(Continued)

(58) Field of Classification Search
CPC ................................................... A61B 81/085
See application file for complete search history.

(56) References Cited

U.S. PATENT DOCUMENTS

| 2,137,710 A | 12/1937 | Anderson |
| 4,031,898 A | 6/1977 | Hiltebrandt et al. |

(Continued)

FOREIGN PATENT DOCUMENTS

| AU | 2006229913 B2 | 11/2011 |
| CA | 2602015 A1 | 10/2006 |

(Continued)

OTHER PUBLICATIONS

PCT International Search Report, PCT/US2006/010569, dated Jul. 24, 2006, 8 pages.
(Continued)

*Primary Examiner* — Lee S Cohen
(74) *Attorney, Agent, or Firm* — Wesley Scott Ashton; Kevin T. Godlewski

(57) ABSTRACT

A surgical apparatus and methods for severing and welding tissue, in particular blood vessels. The apparatus includes an elongated shaft having a pair of relatively movable jaws at a distal end thereof. A first heating element on one of the jaws is adapted to heat up to a first temperature and form a welded region within the tissue, while a second heating element on one of the jaws is adapted to heat up to a second temperature and sever the tissue within the welded region. The first and second heating elements may be provided on the same or opposite jaws. A control handle provided on the proximal end of the elongated shaft includes controls for opening and closing the jaws, and may include an actuator for sending current through the first and second heating elements. The first and second heating elements may be electrically connected in series, and the first heating element may be bifurcated such that it conducts about one half of the
(Continued)

current as the second heating element. A force-limiting mechanism provided either within the control handle, in the elongated shaft, or at the jaws limits the pressure applied to the tissue by the jaws to ensure that the tissue is severed and the ends effectively welded within a short amount of time.

14 Claims, 21 Drawing Sheets

Related U.S. Application Data of application No. 13/494,985, filed on Jun. 12, 2012, now Pat. No. 8,894,638, which is a continuation of application No. 11/090,750, filed on Mar. 25, 2005, now Pat. No. 8,197,472.

(51) Int. Cl.
  *A61B 17/29* (2006.01)
  *A61B 18/14* (2006.01)
  *A61B 90/00* (2016.01)
  *A61B 17/00* (2006.01)
  *A61B 17/34* (2006.01)

(52) U.S. Cl.
  CPC ............... *A61B 2017/00084* (2013.01); *A61B 2017/00353* (2013.01); *A61B 2017/00504* (2013.01); *A61B 2017/2912* (2013.01); *A61B 2017/2936* (2013.01); *A61B 2017/2945* (2013.01); *A61B 2017/3445* (2013.01); *A61B 2018/1432* (2013.01)

(56) References Cited

U.S. PATENT DOCUMENTS

| | | |
|---|---|---|
| 4,071,028 A | 1/1978 | Perkins |
| 4,128,099 A | 12/1978 | Bauer |
| 4,281,646 A | 8/1981 | Kinoshita |
| 4,418,692 A | 12/1983 | Guay |
| 4,468,217 A | 8/1984 | Kuzmick et al. |
| 4,759,362 A | 7/1988 | Taniguchi |
| 4,767,519 A | 8/1988 | de Nora |
| 4,801,015 A | 1/1989 | Lubock et al. |
| 4,884,559 A | 12/1989 | Collins |
| 4,884,599 A | 12/1989 | Collins |
| 5,009,661 A | 4/1991 | Michelson |
| 5,052,402 A | 10/1991 | Bencini |
| 5,098,430 A | 3/1992 | Fleenor |
| 5,108,474 A | 4/1992 | Riedy et al. |
| 5,147,356 A | 4/1992 | Bhatta |
| 5,151,102 A | 9/1992 | Kamiyama et al. |
| 5,154,709 A | 10/1992 | Johnson |
| 5,156,613 A | 10/1992 | Sawyer |
| 5,160,334 A | 11/1992 | Billings |
| 5,217,460 A | 6/1993 | Knoepfler |
| 5,258,006 A | 11/1993 | Rydell et al. |
| 5,282,799 A | 2/1994 | Rydell |
| 5,290,278 A | 3/1994 | Anderson |
| 5,300,065 A | 4/1994 | Anderson |
| 5,312,426 A | 5/1994 | Segawa et al. |
| 5,314,424 A | 5/1994 | Nicholas |
| 5,318,040 A | 6/1994 | Kensey et al. |
| 5,336,221 A | 8/1994 | Anderson |
| 5,342,381 A | 8/1994 | Tidemand |
| 5,352,222 A | 10/1994 | Rydell |
| 5,356,408 A | 10/1994 | Rydell |
| 5,361,583 A | 11/1994 | Huitema |
| 5,364,395 A | 11/1994 | West, Jr. |
| 5,383,888 A | 1/1995 | Zvenyatsky et al. |
| 5,405,344 A | 4/1995 | Williamson et al. |
| 5,443,463 A | 8/1995 | Stern et al. |
| 5,445,638 A | 8/1995 | Rydell |
| 5,451,222 A | 9/1995 | De Maagd et al. |
| 5,453,599 A | 9/1995 | Hall, Jr. |
| 5,462,546 A | 10/1995 | Rydell |
| 5,472,442 A | 12/1995 | Klicek |
| 5,496,317 A | 3/1996 | Goble et al. |
| 5,507,744 A | 4/1996 | Tay et al. |
| 5,507,773 A | 4/1996 | Huitema et al. |
| 5,509,922 A | 4/1996 | Aranyi et al. |
| 5,514,134 A | 5/1996 | Rydell et al. |
| 5,562,503 A | 10/1996 | Ellman |
| 5,599,350 A | 2/1997 | Schulze et al. |
| 5,624,452 A | 4/1997 | Yates |
| 5,647,871 A | 7/1997 | Levine et al. |
| 5,669,934 A | 9/1997 | Sawyer |
| 5,674,219 A | 10/1997 | Monson et al. |
| 5,683,412 A | 11/1997 | Scarfone |
| 5,709,675 A | 1/1998 | Williams |
| 5,709,680 A | 1/1998 | Yates et al. |
| 5,716,366 A | 2/1998 | Yates |
| 5,722,962 A | 3/1998 | Garcia |
| 5,725,477 A | 3/1998 | Yasui |
| 5,741,285 A | 4/1998 | McBrayer et al. |
| 5,752,973 A | 5/1998 | Kieturakis |
| 5,755,717 A | 5/1998 | Yates et al. |
| 5,766,134 A | 6/1998 | Lisak et al. |
| 5,766,166 A | 6/1998 | Hooven |
| 5,776,130 A | 7/1998 | Buysse et al. |
| 5,807,393 A | 9/1998 | Williamson et al. |
| 5,810,810 A | 9/1998 | Tay et al. |
| 5,810,811 A | 9/1998 | Yates et al. |
| 5,827,271 A | 10/1998 | Buysse et al. |
| 5,833,690 A | 11/1998 | Yates et al. |
| 5,843,017 A | 12/1998 | Yoon |
| 5,849,011 A | 12/1998 | Jones |
| 5,853,410 A | 12/1998 | Greff et al. |
| 5,860,975 A | 1/1999 | Goble et al. |
| 5,871,496 A | 2/1999 | Ginn et al. |
| 5,891,141 A | 4/1999 | Rydell |
| 5,906,630 A | 5/1999 | Anderhub et al. |
| 5,908,415 A | 6/1999 | Sinofsky |
| 5,908,420 A | 6/1999 | Parins et al. |
| 5,911,719 A | 6/1999 | Eggers |
| 5,944,718 A | 8/1999 | Austin et al. |
| 5,947,984 A | 9/1999 | Whipple |
| 5,954,686 A | 9/1999 | Garito |
| 5,997,533 A | 12/1999 | Kuhns |
| 6,004,320 A | 12/1999 | Casscells et al. |
| 6,022,313 A | 2/2000 | Ginn et al. |
| 6,024,741 A | 2/2000 | Williamson et al. |
| 6,027,501 A | 2/2000 | Goble et al. |
| 6,033,424 A | 3/2000 | Ouchi |
| 6,039,733 A | 3/2000 | Buysse et al. |
| 6,059,781 A | 5/2000 | Yamanashi et al. |
| 6,066,151 A | 5/2000 | Miyawaki |
| 6,074,389 A | 6/2000 | Levine et al. |
| 6,110,190 A | 8/2000 | Ginn et al. |
| 6,113,596 A | 9/2000 | Hooven |
| 6,174,309 B1 | 1/2001 | Wrublewski et al. |
| 6,179,837 B1 | 1/2001 | Hooven |
| 6,190,386 B1 | 2/2001 | Rydell |
| 6,206,876 B1 | 3/2001 | Levine et al. |
| 6,251,092 B1 | 6/2001 | Qin |
| 6,254,623 B1 | 7/2001 | Haibel, Jr. et al. |
| 6,267,761 B1 | 7/2001 | Ryan |
| 6,270,492 B1 | 8/2001 | Sinofsky |
| 6,270,497 B1 | 8/2001 | Sekino |
| 6,273,887 B1 | 8/2001 | Yamauchi et al. |
| 6,352,503 B1 | 3/2002 | Matsui et al. |
| 6,352,532 B1 | 3/2002 | Kramer et al. |
| 6,391,029 B1 | 5/2002 | Hooven et al. |
| 6,406,425 B1 | 6/2002 | Chin |
| 6,406,454 B1 | 6/2002 | Hajianpour |
| 6,423,055 B1 | 7/2002 | Farr |
| 6,432,105 B1 | 8/2002 | Ellman et al. |
| 6,458,122 B1 | 10/2002 | Pozzato |
| 6,464,701 B1 | 10/2002 | Hooven et al. |
| 6,478,794 B1 | 11/2002 | Trapp |
| 6,517,536 B2 | 2/2003 | Hooven et al. |
| 6,521,307 B2 | 2/2003 | Weder |
| 6,522,933 B2 | 2/2003 | Nguyen |

(56) References Cited

U.S. PATENT DOCUMENTS

| | | |
|---|---|---|
| 6,524,307 B1 | 2/2003 | Palmerton et al. |
| 6,527,771 B1 | 3/2003 | Weadock et al. |
| 6,544,210 B1 | 4/2003 | Trudel et al. |
| 6,551,313 B1 | 4/2003 | Levin |
| 6,558,375 B1 | 5/2003 | Sinofsky |
| 6,572,609 B1 | 6/2003 | Farr |
| 6,576,033 B1 | 6/2003 | Booth |
| 6,579,278 B1 | 6/2003 | Bencini |
| 6,579,285 B2 | 6/2003 | Sinofsky |
| 6,582,451 B1 | 6/2003 | Marucci et al. |
| 6,582,536 B2 | 6/2003 | Shimada |
| 6,582,582 B2 | 6/2003 | Becking |
| 6,602,252 B2 | 8/2003 | Mollenauer |
| 6,605,055 B1 | 8/2003 | Sinofsky |
| 6,613,069 B2 | 9/2003 | Boyd et al. |
| 6,626,901 B1 | 9/2003 | Treat |
| 6,652,514 B2 | 11/2003 | Ellman |
| 6,656,177 B2 | 12/2003 | Truckai et al. |
| 6,663,610 B1 | 12/2003 | Thompson et al. |
| 6,676,656 B2 | 1/2004 | Sinofsky |
| 6,679,873 B2 | 1/2004 | Rabiner |
| 6,682,528 B2 | 1/2004 | Frazier et al. |
| 6,685,665 B2 | 2/2004 | Booth et al. |
| 6,695,837 B2 | 2/2004 | Howell |
| 6,702,780 B1 | 3/2004 | Gilboa |
| 6,746,504 B2 | 6/2004 | Booth |
| 6,770,072 B1 | 8/2004 | Truckai et al. |
| 6,773,409 B2 | 8/2004 | Truckai et al. |
| 6,802,843 B2 | 10/2004 | Truckai et al. |
| 6,821,273 B2 | 11/2004 | Mollenauer |
| 6,830,569 B2 | 12/2004 | Thompson |
| 6,860,880 B2 | 3/2005 | Treat et al. |
| 6,908,463 B2 | 6/2005 | Treat et al. |
| 6,958,070 B2 | 10/2005 | Witt et al. |
| 6,966,907 B2 | 11/2005 | Goble |
| 6,966,909 B2 | 11/2005 | Marshall et al. |
| 6,994,707 B2 | 2/2006 | Ellman |
| 7,033,356 B2 | 4/2006 | Latterell et al. |
| 7,083,620 B2 | 8/2006 | Jahns et al. |
| 7,094,231 B1 | 8/2006 | Ellman |
| 7,112,199 B2 | 9/2006 | Cosmescu |
| 7,147,637 B2 | 12/2006 | Goble |
| 7,204,835 B2 | 4/2007 | Latterell et al. |
| 7,211,080 B2 | 5/2007 | Treat et al. |
| 7,306,599 B2 | 12/2007 | Karasawa et al. |
| 7,316,683 B2 | 1/2008 | Kasahara et al. |
| 7,326,202 B2 | 2/2008 | McGaffigan |
| 7,329,257 B2 | 2/2008 | Kanehira et al. |
| 7,364,577 B2 | 4/2008 | Wham |
| 7,367,976 B2 | 5/2008 | Lawes et al. |
| 7,396,356 B2 | 7/2008 | Mollenauer |
| 7,513,896 B2 | 4/2009 | Orszulak |
| 7,632,270 B2 | 12/2009 | Livneh |
| 7,645,289 B2 | 1/2010 | Bayer |
| 7,695,470 B1 | 4/2010 | Stewart et al. |
| 7,699,861 B2 | 4/2010 | Bayer |
| 7,887,558 B2 | 2/2011 | Lin et al. |
| 7,918,845 B2 | 4/2011 | Saadat et al. |
| 7,918,848 B2 | 4/2011 | Lau et al. |
| 8,197,472 B2 | 6/2012 | Lau et al. |
| 8,221,306 B2 | 7/2012 | Okada et al. |
| 8,251,989 B1 | 8/2012 | Newton et al. |
| 8,257,352 B2 | 9/2012 | Lawes et al. |
| 8,425,508 B2 | 4/2013 | Kasahara et al. |
| 8,623,003 B2 | 1/2014 | Lau et al. |
| 8,657,818 B2 | 2/2014 | Lin |
| 8,894,638 B2 | 11/2014 | Lau et al. |
| 8,961,503 B2 | 2/2015 | Lau et al. |
| 9,402,679 B2 | 8/2016 | Ginnebaugh |
| 9,402,680 B2 | 8/2016 | Ginnebaugh et al. |
| 9,955,858 B2 | 5/2018 | Pamnani |
| 9,968,396 B2 | 5/2018 | Abbott |
| 2002/0019631 A1 | 2/2002 | Kidder et al. |
| 2002/0058938 A1 | 5/2002 | Comescu |
| 2002/0115997 A1 | 8/2002 | Truckai et al. |
| 2002/0128603 A1 | 9/2002 | Booth et al. |
| 2003/0014052 A1 | 1/2003 | Buysse et al. |
| 2003/0060816 A1 | 3/2003 | Iida |
| 2003/0073991 A1 | 4/2003 | Francischelli |
| 2003/0073994 A1 | 4/2003 | Schulze |
| 2003/0125734 A1 | 7/2003 | Mollenauer |
| 2003/0130654 A1 | 7/2003 | Kasahara et al. |
| 2003/0130674 A1 | 7/2003 | Kasahara et al. |
| 2003/0130675 A1 | 7/2003 | Kasahara et al. |
| 2003/0139649 A1 | 7/2003 | Kasahara et al. |
| 2003/0144652 A1 | 7/2003 | Baker |
| 2003/0144660 A1 | 7/2003 | Mollenauer |
| 2003/0163123 A1 | 8/2003 | Goble et al. |
| 2003/0171747 A1 | 9/2003 | Kanehira et al. |
| 2003/0187429 A1 | 10/2003 | Karasawa et al. |
| 2004/0006333 A1 | 1/2004 | Arnold |
| 2004/0054365 A1 | 3/2004 | Goble |
| 2004/0059397 A1 | 3/2004 | Sinofsky |
| 2004/0064151 A1 | 4/2004 | Mollenauer |
| 2004/0078035 A1 | 4/2004 | Kanehira et al. |
| 2004/0102450 A1 | 5/2004 | Ewing et al. |
| 2004/0133228 A1 | 7/2004 | Bayer |
| 2004/0176756 A1 | 9/2004 | McGaffigan |
| 2004/0204725 A1 | 10/2004 | Bayer |
| 2004/0260279 A1 | 12/2004 | Goble et al. |
| 2005/0033278 A1 | 2/2005 | McClurken et al. |
| 2005/0049633 A1 | 3/2005 | Watanabe |
| 2005/0072827 A1 | 4/2005 | Mollenauer |
| 2005/0113826 A1 | 5/2005 | Johnson |
| 2005/0113828 A1 | 5/2005 | Shields et al. |
| 2005/0171533 A1 | 8/2005 | Latterell et al. |
| 2005/0182398 A1 | 8/2005 | Paterson |
| 2006/0041254 A1 | 2/2006 | Francischelli et al. |
| 2006/0074444 A1 | 4/2006 | Lin et al. |
| 2006/0211916 A1 | 9/2006 | Kasahara et al. |
| 2006/0217697 A1 | 9/2006 | Lau et al. |
| 2006/0217706 A1 | 9/2006 | Lau et al. |
| 2006/0235379 A1 | 10/2006 | McClurken et al. |
| 2006/0271037 A1 | 11/2006 | Maroney et al. |
| 2007/0021405 A1 | 1/2007 | Abouabdellah et al. |
| 2007/0021424 A1 | 1/2007 | Abouabdellah et al. |
| 2007/0027141 A1 | 2/2007 | Abouabdellah et al. |
| 2007/0078456 A1 | 4/2007 | Dumbauld et al. |
| 2007/0149993 A1 | 6/2007 | Kasahara et al. |
| 2007/0173814 A1 | 7/2007 | Hixson et al. |
| 2007/0213749 A1 | 9/2007 | Kogasaka et al. |
| 2007/0260242 A1 | 11/2007 | Dycus et al. |
| 2007/0293856 A1 | 12/2007 | Paul |
| 2007/0293858 A1 | 12/2007 | Fischer |
| 2008/0015567 A1 | 1/2008 | Kimura |
| 2008/0015575 A1 | 1/2008 | Odom |
| 2008/0039835 A1 | 2/2008 | Johnson et al. |
| 2008/0154091 A1 | 6/2008 | Dejima et al. |
| 2008/0306335 A1 | 12/2008 | Lau et al. |
| 2009/0024121 A1 | 1/2009 | Kasahara et al. |
| 2009/0118730 A1 | 5/2009 | Mollenauer |
| 2009/0299367 A1 | 12/2009 | Ginnebaugh et al. |
| 2010/0048992 A1 | 2/2010 | Okada et al. |
| 2010/0292533 A1 | 11/2010 | Kasahara et al. |
| 2011/0046439 A1 | 2/2011 | Pamnani et al. |
| 2011/0046624 A1 | 2/2011 | Lin |
| 2011/0257643 A1 | 10/2011 | Lau |
| 2011/0288369 A1 | 11/2011 | Ginnebaugh |
| 2011/0288546 A1 | 11/2011 | Abbott |
| 2012/0283720 A1 | 11/2012 | Newton et al. |
| 2012/0316550 A1 | 12/2012 | Lau et al. |
| 2012/0316650 A1 | 12/2012 | Lau et al. |
| 2013/0018373 A1 | 1/2013 | Lau et al. |
| 2014/0194876 A1 | 7/2014 | Lau et al. |

FOREIGN PATENT DOCUMENTS

| | | |
|---|---|---|
| CA | 2602381 A1 | 10/2006 |
| DE | 10328514 B3 | 3/2005 |
| EP | 538984 A3 | 4/1993 |
| EP | 0538984 B1 | 4/1993 |
| EP | 538984 A2 | 7/1993 |
| EP | 1330991 A1 | 7/2003 |
| EP | 1632192 A1 | 3/2006 |

(56) References Cited

FOREIGN PATENT DOCUMENTS

| | | |
|---|---|---|
| EP | 1330991 B1 | 9/2007 |
| EP | 1878399 A1 | 1/2008 |
| EP | 1878400 A1 | 1/2008 |
| EP | 1894535 A2 | 3/2008 |
| EP | 1632192 B1 | 3/2009 |
| EP | 2106762 A1 | 10/2009 |
| EP | 1885270 B1 | 8/2010 |
| EP | 1861034 B1 | 9/2010 |
| EP | 2285305 A2 | 2/2011 |
| EP | 1894535 A3 | 3/2011 |
| JP | H07508666 A | 9/1995 |
| JP | H10511030 A | 10/1998 |
| JP | 2000135222 A | 5/2000 |
| JP | 2000139943 | 5/2000 |
| JP | 2003144451 A | 5/2003 |
| JP | 2005-058553 A | 3/2005 |
| JP | 2005514102 A | 5/2005 |
| JP | 2008534068 A | 8/2008 |
| JP | 2008534069 A | 8/2008 |
| JP | 2011521723 A | 7/2011 |
| JP | 4966959 B2 | 7/2012 |
| WO | 1993020769 A1 | 10/1993 |
| WO | 1997005829 A1 | 2/1997 |
| WO | 1997010764 A1 | 3/1997 |
| WO | 00/47124 A1 | 8/2000 |
| WO | 02/080794 A1 | 10/2002 |
| WO | 03/057058 A1 | 7/2003 |
| WO | 2003061456 A2 | 7/2003 |
| WO | 2003061456 A3 | 1/2004 |
| WO | 2005048863 A1 | 6/2005 |
| WO | 2006104835 A1 | 10/2006 |
| WO | 2006104836 A2 | 10/2006 |
| WO | 2006104836 A3 | 1/2007 |
| WO | 2009039179 A1 | 3/2009 |
| WO | 2009154976 A2 | 12/2009 |
| WO | 2009154976 A3 | 3/2010 |
| WO | 2009154976 A4 | 5/2010 |
| WO | 2009154976 A9 | 2/2011 |

OTHER PUBLICATIONS

PCT International Preliminary Report on Patentability, PCT/US2006/010569, dated Oct. 4, 2007, 10 pages.
PCT International Search Report, PCT/US2006/010568, dated Jul. 24, 2006, 3 pages.
PCT International Preliminary Report on Patentability, PCT/US2006/010568, dated Oct. 4, 2007, 7 pages.
European Examination Report, EP 06739388.4, dated Sep. 17, 2008, 7 pages.
English translation of the abstract for Japanese Publication No. 2003-144451 dated May 20, 2003.
English translation of the abstract for Japanese Publication No. 2003-294157 dated Mar. 10, 2003.
Stedman's Medical Dictionary, pp. 3 and 238 (1982), Waverly Press, Inc.
International Search Report and Written Opinion dated Jan. 19, 2010 for PCT Application No. PCT/US2009/045272; (20 pages).
Non-Final Office Action dated May 7, 2012 for U.S. Appl. No. 12/472,657; (22 pages).
U.S. Appl. No. 13/494,985, filed Jun. 12, 2012 (available via USPTO database).
U.S. Appl. No. 13/549,367, filed Jul. 13, 2012 (available via USPTO database).
U.S. Appl. No. 13/094,783, filed Apr. 26, 2011 (available via USPTO database).
U.S. Appl. No. 12/545,690, filed Aug. 21, 2009 (available via USPTO database).
Non-Final Office Action dated Mar. 14, 2012 for U.S. Appl. No. 13/094,783; (8 pages).
English translation of the abstract for JP Publication No. 2003-144451 dated May 20, 2003.
English translation of the abstract for JP Application No. 2003-294157 (Publication No. 2005-058553) dated Mar. 10, 2005.
European Examination Report, EP Application No. EP 06739387.6, dated Dec. 11, 2008 (4 pages).
U.S. Appl. No. 13/047,778 filed Mar. 14, 2011 (available via USPTO database).
U.S. Appl. No. 14/148,671 filed Jan. 6, 2014 (available via USPTO database).
U.S. Appl. No. 12/472,657 filed May 27, 2009 (available via USPTO database).
European Examination Report, EP Application No. 06739387.6, dated Dec. 11, 2008, 4 pages.
International Search Report and Written Opinion dated Jan. 19, 2010 for PCT Application No. PCT/US2009/045272.
L.S. Feldman et al. (eds.), Fundamentals of Electrosurgery Part I: Principles of Radiofrequency Energy for Surgery, the SAGES Manual on the Fundamental Use of Surgical Energy (FUSE), 2012, 15-59, Springer-Verlag, New York.
Dielectric Heating, downloaded Dec. 2, 2014 from http://www.comdel.com/dielectric-heating, 2 pages.
Ohanian, Hans C, Physics, 1985, 658-660, W.W. Norton & Company, Inc., New York.
How RF Heating Works, downloaded Dec. 2, 2014 from http://www.macrowave.com/rftech.html, 1 page.
Electrosurgery: the newest energy-based devices downloaded Dec. 3, 2014 from http://contemporary.obgyn. modernmedicine.com/contemporary-obgyn/cantent/tags/aescula . . ., 6 pages.
Joule heating, Wikipedia, downloaded Dec. 1, 2014 from http://en.wikipedia.org/wiki/Joule_heating, 6 pages.
PCT International Search Report and Written Opinion, PCT/US2006/010569, dated Jan. 4, 2007, 6 pages.
PCT International Preliminary Report on Patentability, PCT/US2006/010569, dated Sep. 25, 2007, 9 pages.
PCT International Search Report and Written Opinion, PCT/US2006/010568, dated Aug. 3, 2006, 8 pages.
PCT International Preliminary Report on Patentability, PCT/US2006/010568, dated Sep. 25, 2007, 6 pages
Stedman's Medical Dictionary, 1982, pp. 3 and 238, 24th ed., Williams & Wilkins, Baltimore, MD, US.
Final Office Action Issued in U.S. Application No. 15/618,112, dated Jun. 29, 2020, 10 pages.
Non-Final Office Action Issued in U.S. Appl. No. 15/618,112 dated Nov. 26, 2019, 11 pages.
Final Office Action Issued in U.S. Appl. No. 15/225,753, dated Feb. 8, 2017, 7 pages.
Non-Final Office Action Issued in U.S. Appl. No. 13/094,795 dated Sep. 29, 2014, 13 pages.
Final Office Action Issued in U.S. Appl. No. 13/094,795 dated Apr. 2, 2015, 13 pages.
Non-Final Office Action Issued in U.S. Appl. No. 15/432,699, dated May 16, 2019, 6 pages.
Non-Final Office Action Issued in U.S. Application No. 14/629,423 dated Mar. 15, 2016, 6 pages.
Non-Final Office Action Issued in U.S. Appl. No. 14/148,671, dated May 9, 2014, 5 pages.
Non-Final Office Action Issued in U.S. Appl. No. 13/549,367 dated Nov. 26, 2012, 6 pages.
Final Office Action Issued in U.S. Appl. No. 13/549,367 dated Aug. 9, 2013, 5 pages.
Final Office Action Issued in U.S. Appl. No. 13/549,367 dated May 2, 2013, 6 pages.
Final Office Action Issued in U.S. Appl. No. 13/047,778, dated Apr. 13, 2012, 6 pages.
Non-Final Office Action Issued in U.S. Appl. No. 11/090,330 dated Mar. 22, 2010, 6 pages.
Non-Final Office Action Issued in U.S. Appl. No. 11/090,330 dated Nov. 17, 2009, 6 pages.
Non-Final Office Action Issued in U.S. Appl. No. 11/090,330 dated Jan. 29, 2009, 5 pages.
Non-Final Office Action Issued in U.S. Appl. No. 11/090,330 dated Apr. 2, 2008, 13 pages.
Final Office Action Issued in U.S. Appl. No. 11/090,330 dated Aug. 6, 2010, 5 pages.

(56) References Cited

OTHER PUBLICATIONS

Final Office Action Issued in U.S. Appl. No. 11/090,330 dated May 15, 2009, 5 pages.
Non-Final Office Action Issued in U.S. Appl. No. 11/090,750 dated May 16, 2011, 8 pages.
Non-Final Office Action Issued in U.S. Appl. No. 11/090,750 dated Dec. 28, 2010, 5 pages.
Non-Final Office Action Issued in U.S. Appl. No. 11/090,750 dated Feb. 22, 2010, 9 pages.
Non-Final Office Action Issued in U.S. Appl. No. 11/090,750 dated Nov. 10, 2008, 13 pages.
Final Office Action Issued in U.S. Appl. No. 11/090,750 dated Apr. 2, 2008, 10 pages.
Final Office Action Issued in U.S. Appl. No. 11/090,750 dated Apr. 17, 2009, 9 pages.
Non-Final Office Action Issued in U.S. Appl. No. 11/090,750 dated Dec. 23, 2013, 7 pages.
Non-Final Office Action Issued in U.S. Appl. No. 11/090,750 dated May 17, 2013, 7 pages.
Final Office Action Issued in U.S. Appl. No. 11/090,750 dated Aug. 26, 2013, 7 pages.
Final Office Action Issued in U.S. Appl. No. 11/090,750 dated Aug. 19, 2012, 6 pages.
Non-Final Office Action Issued in U.S. Appl. No. 14/551,599 dated Feb. 4, 2016, 9 pages.
Final Office Action Issued in U.S. Appl. No. 14/551,599 dated May 26, 2016, 9 pages.
Non-Final Office Action Issued in U.S. Appl. No. 12/545,690 dated Nov. 5, 2015, 14 pages.
Non-Final Office Action Issued in U.S. Appl. No. 12/545,690 dated Apr. 28, 2014, 22 pages.
Non-Final Office Action Issued in U.S. Appl. No. 12/545,690 dated Jan. 8, 2013, 12 pages.
Final Office Action Issued in U.S. Appl. No. 12/545,690 dated Jul. 14, 2016, 20 pages.
Final Office Action Issued in U.S. Appl. No. 12/545,690 dated Dec. 15, 2014, 32 pages.
Final Office Action Issued in U.S. Appl/ No. 12/545,690 dated Oct. 21, 2013, 15 pages.
Non-Final Office Action Issued in U.S. Appl. No. 12/472,657 dated Jun. 3, 2014, 19 pages.
Non-Final Office Action Issued in U.S. Appl. No. 12/472,657 dated May 7, 2012, 13 pages.
Final Office Action Issued in U.S. Appl. No. 12/472,657 dated Feb. 4, 2015, 17 pages.
Final Office Action Issued in U.S. Appl. No. 12/472,657 dated Jan. 14, 2013, 17 pages.
Non-Final Office Action issued in U.S. Appl. No. 15/958,447 dated Sep. 2, 2020, 8 pages.

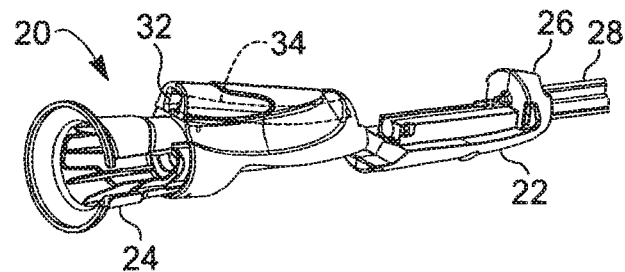
Fig.1A
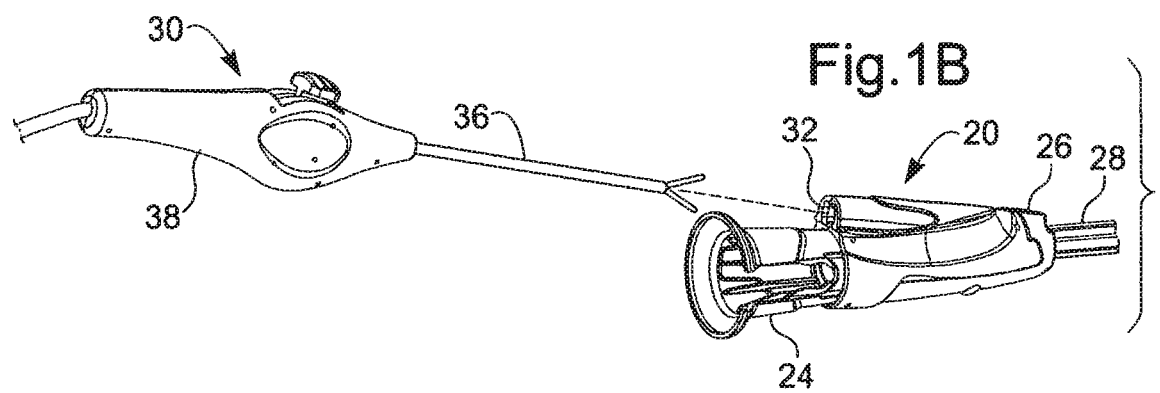
Fig.1B
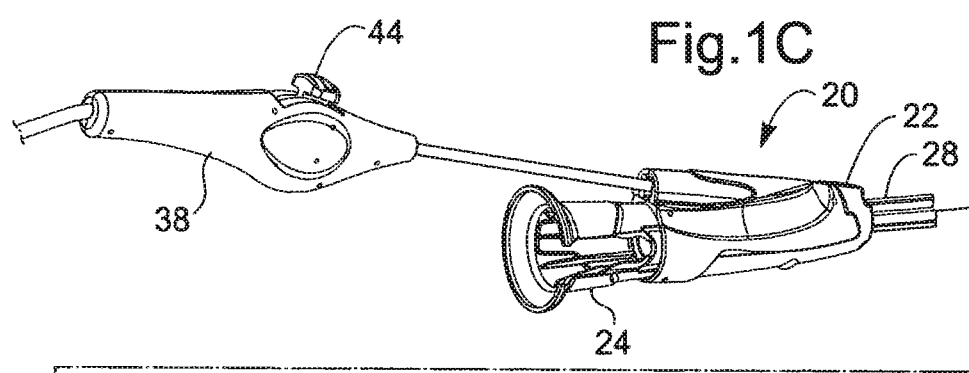
Fig.1C
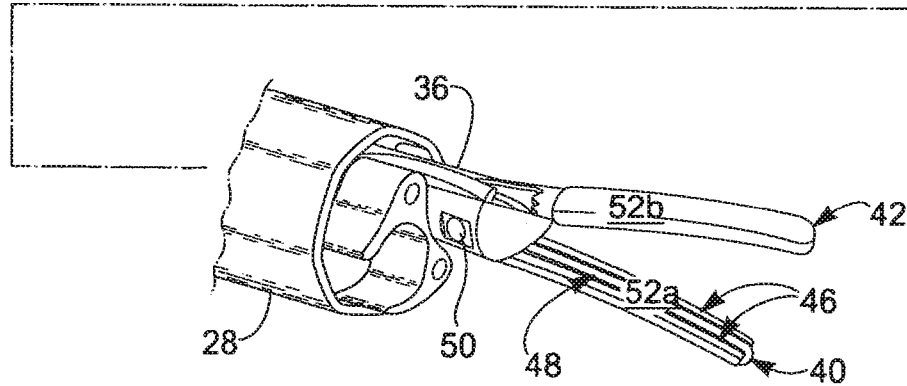

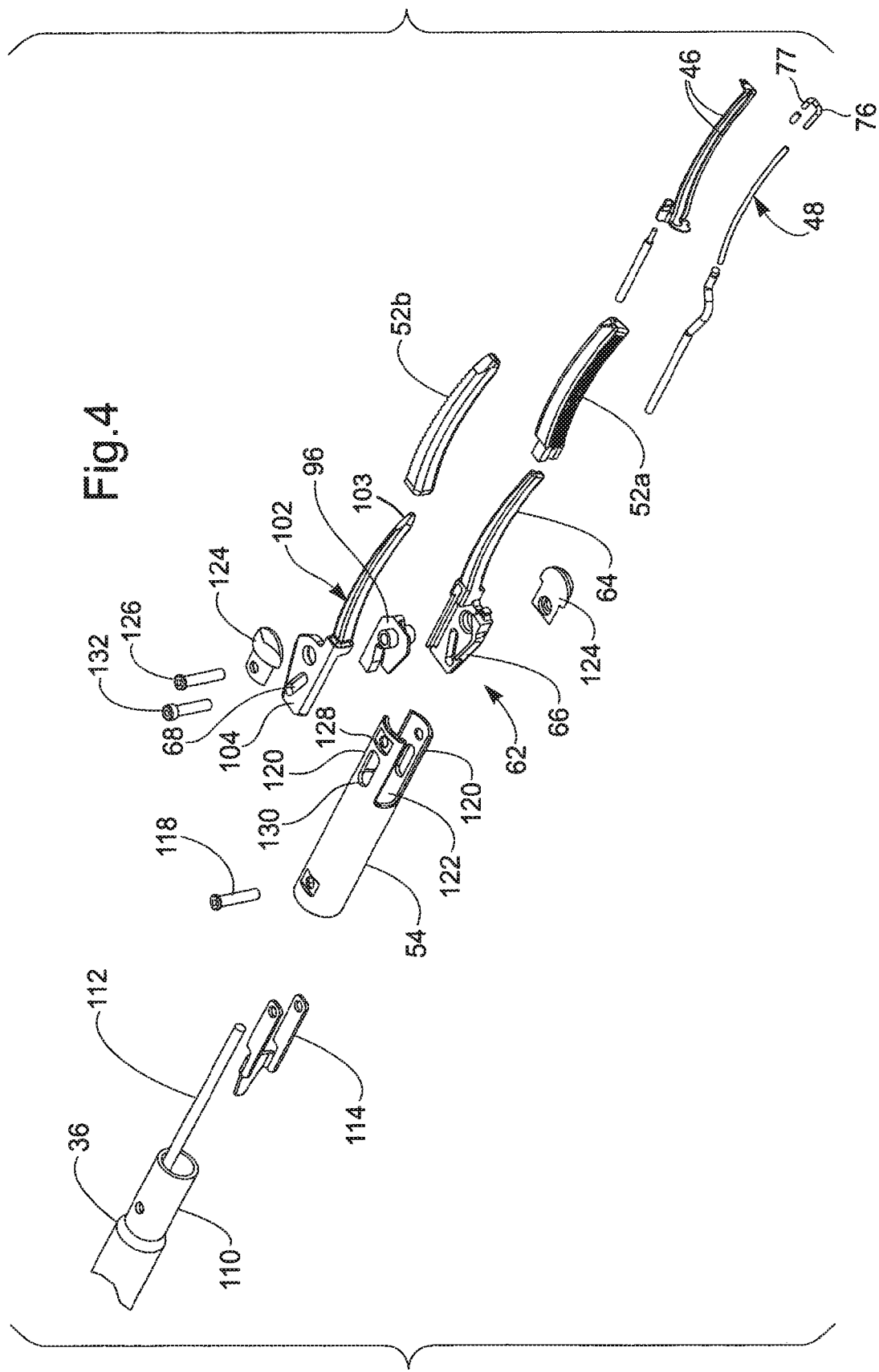

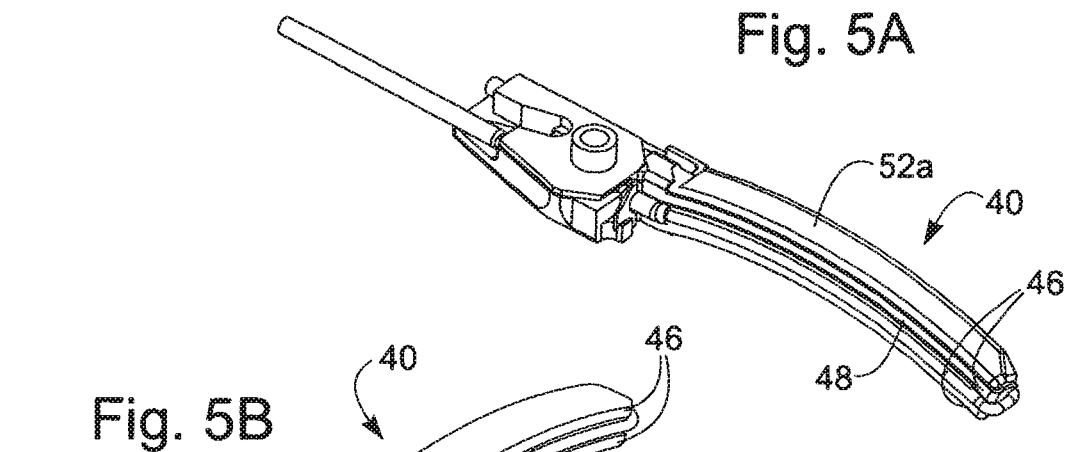
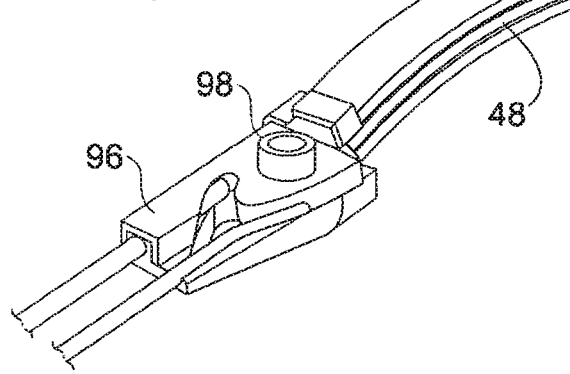
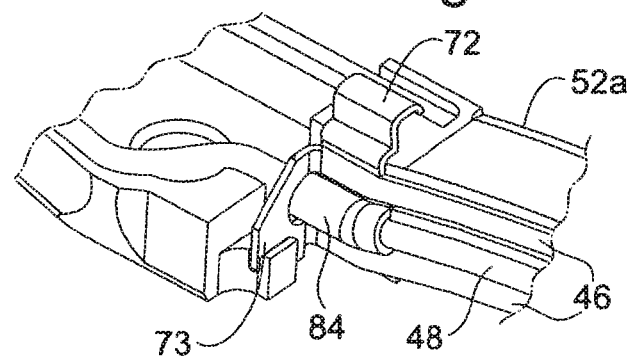
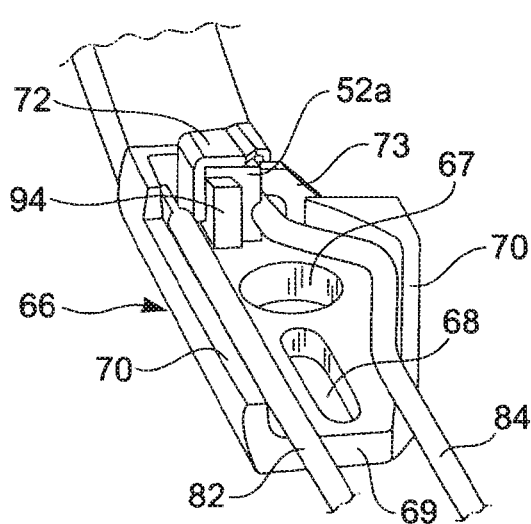

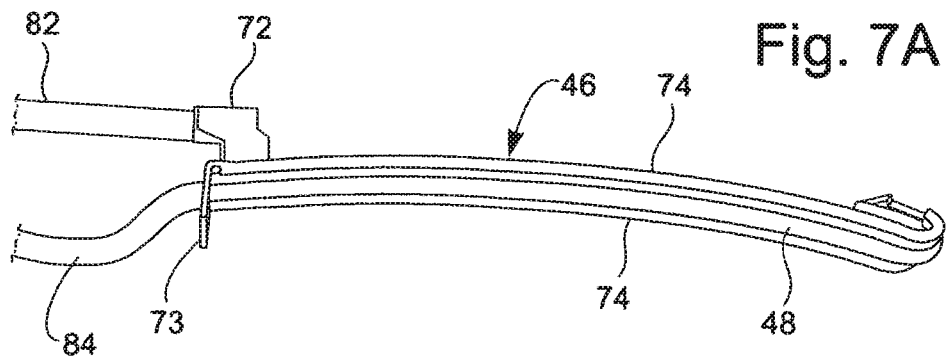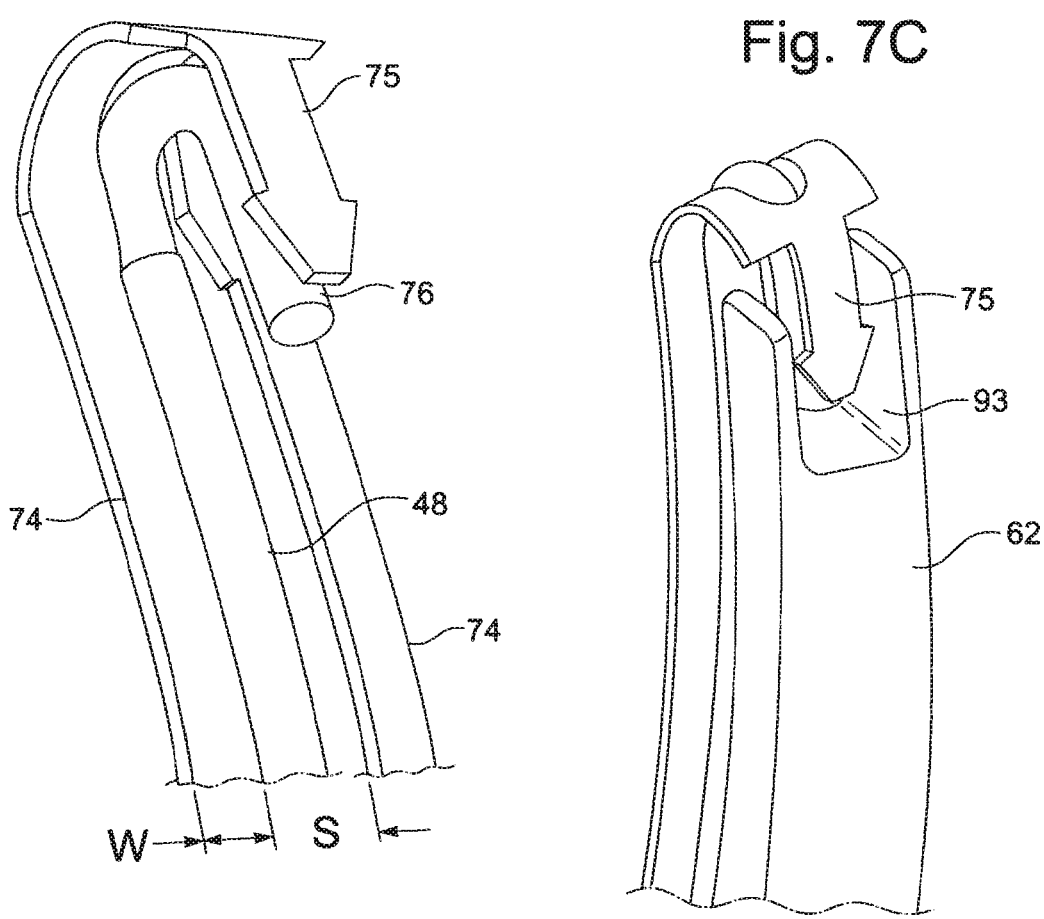

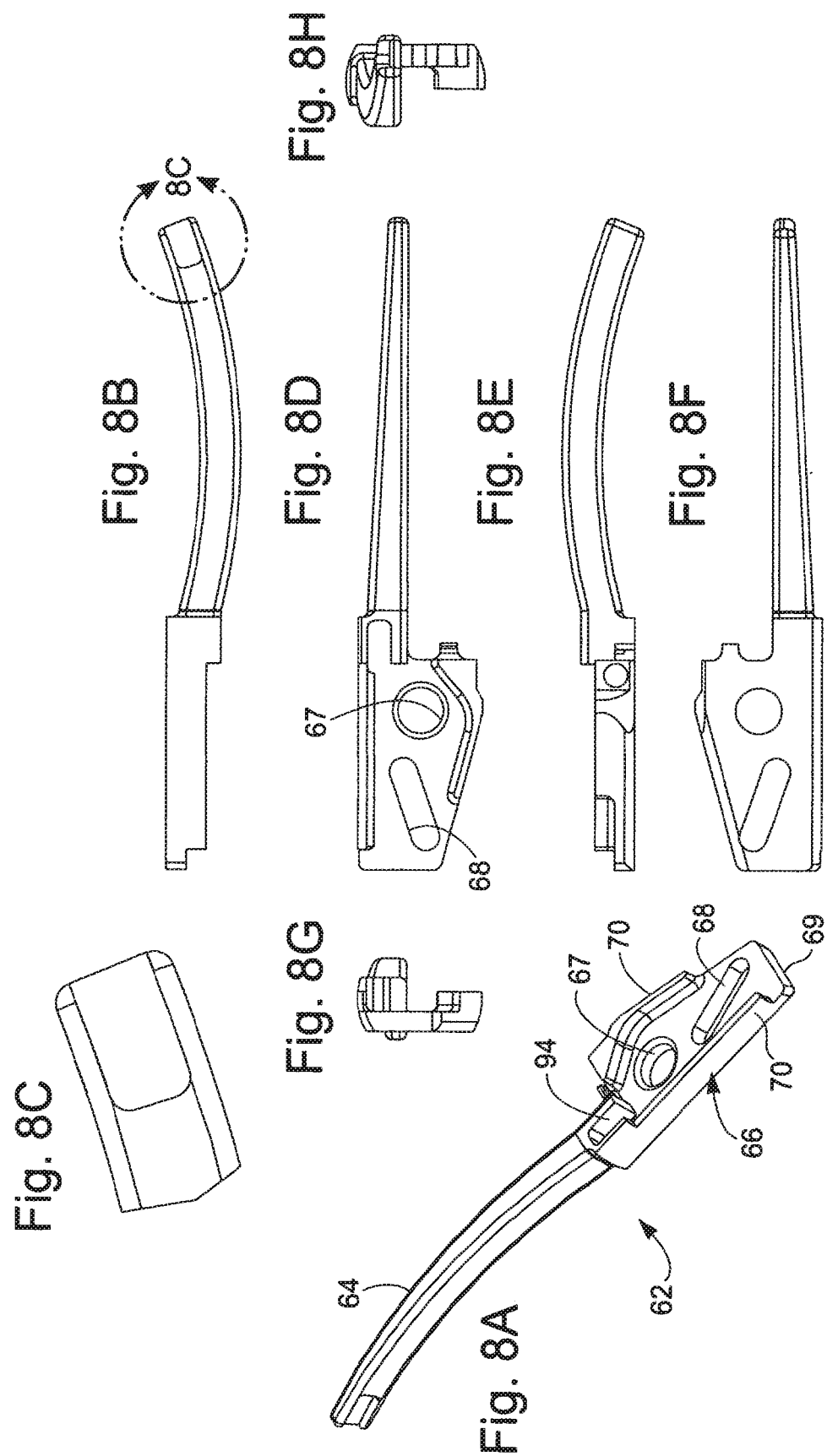

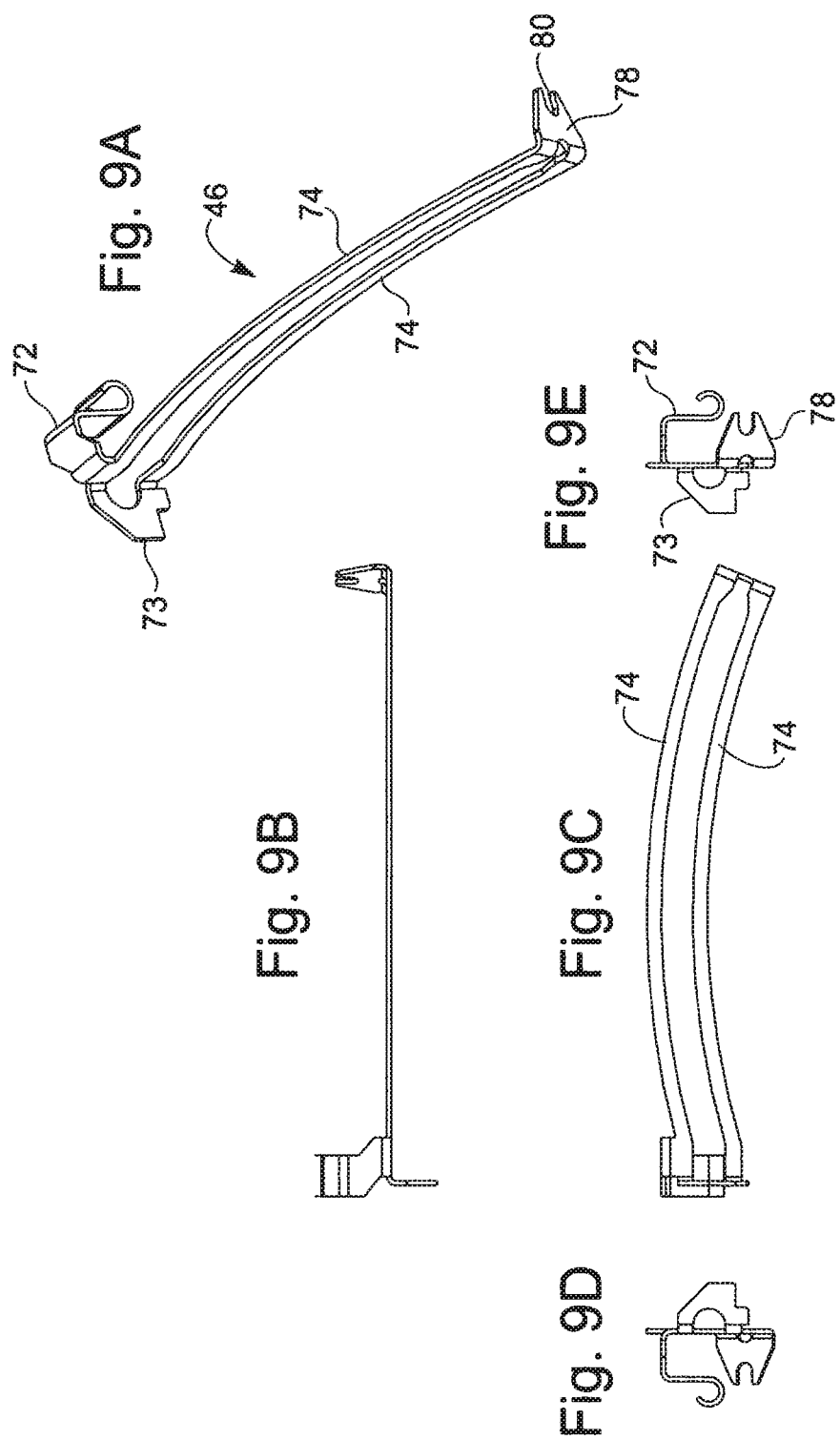

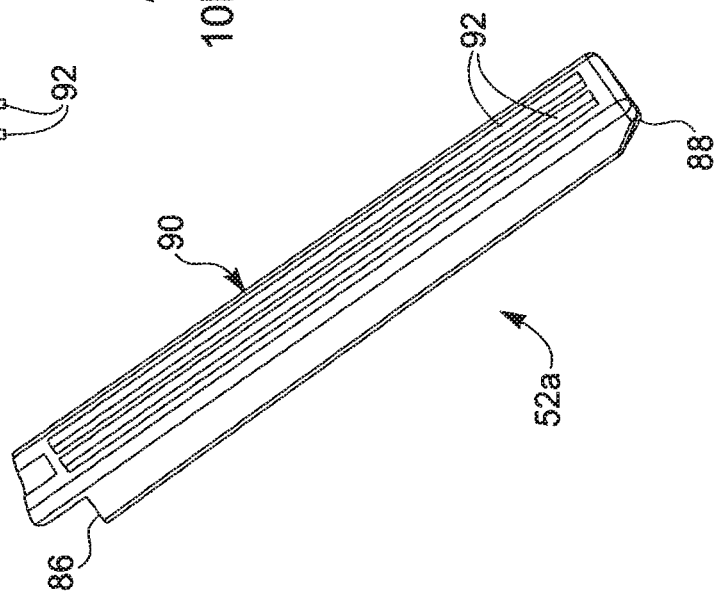
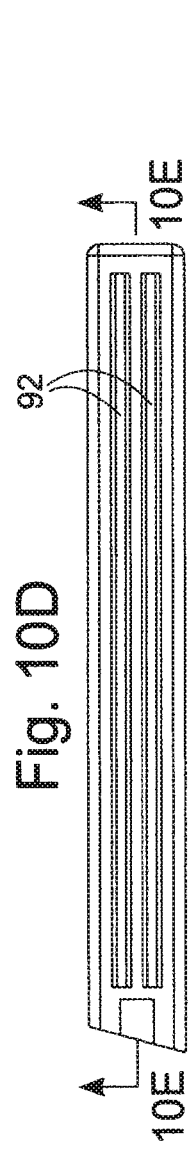
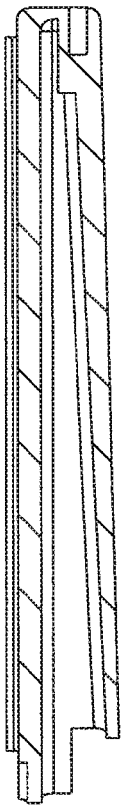

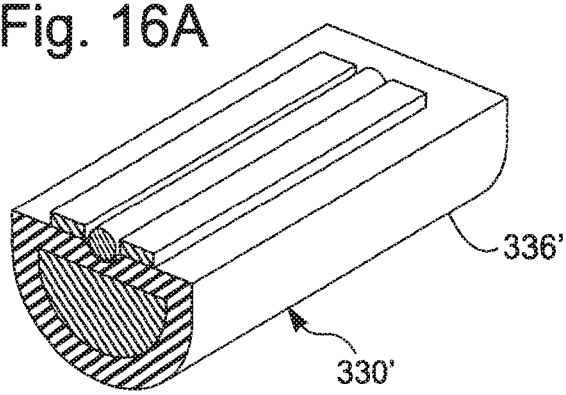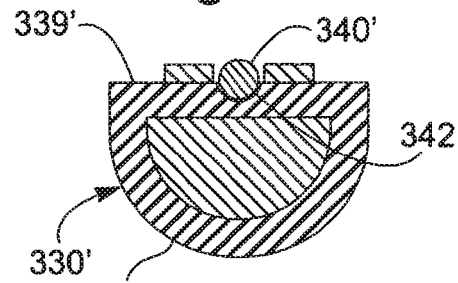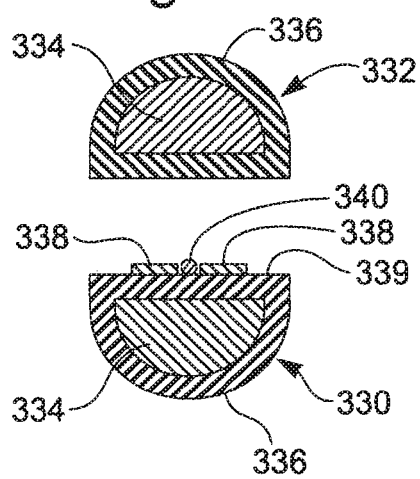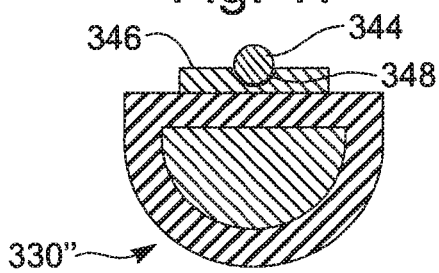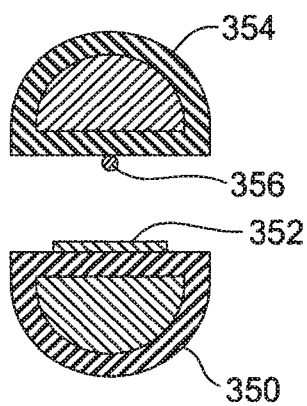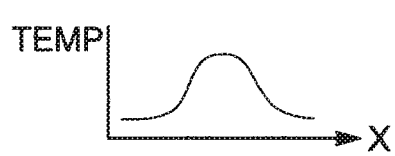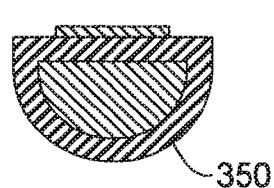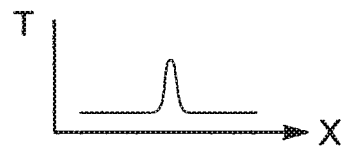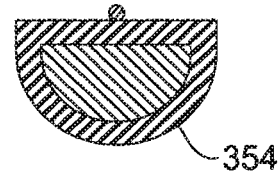

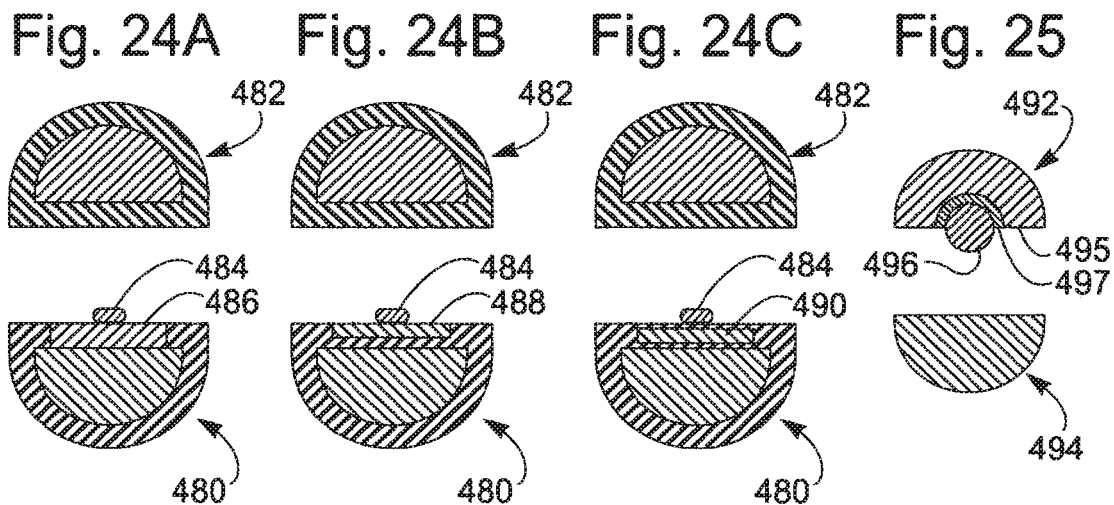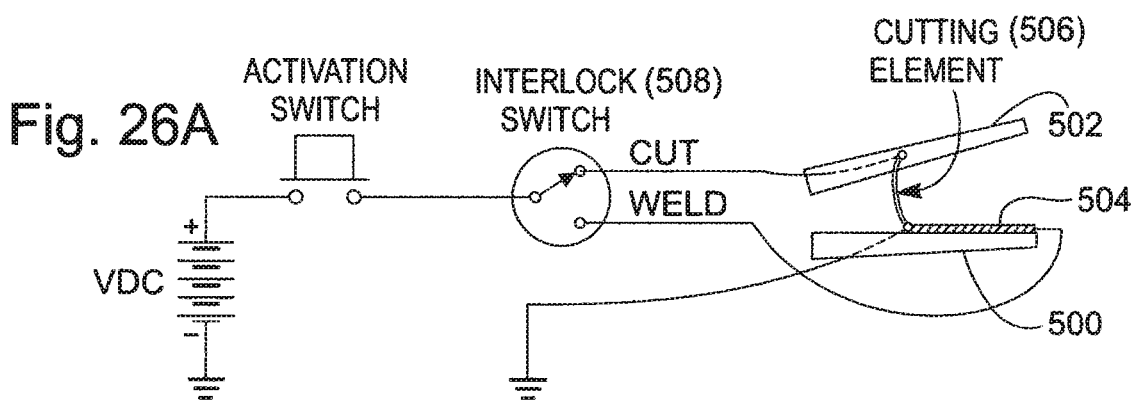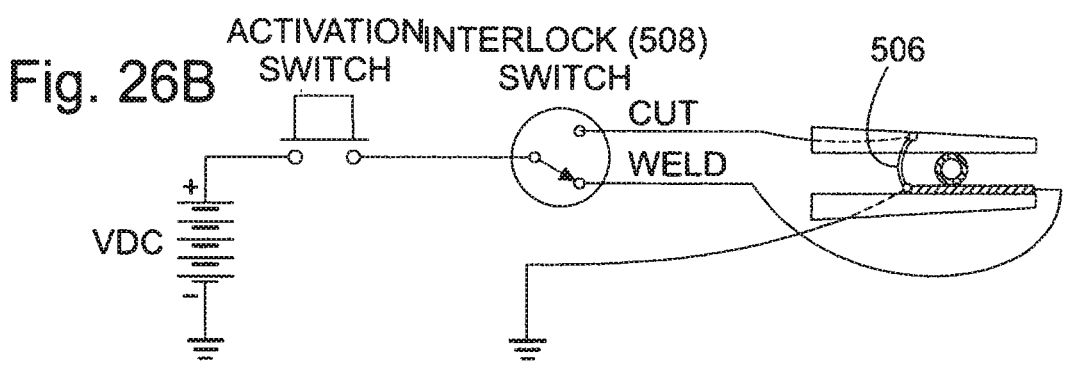

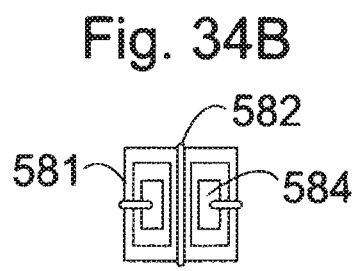
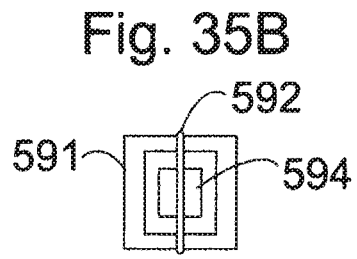
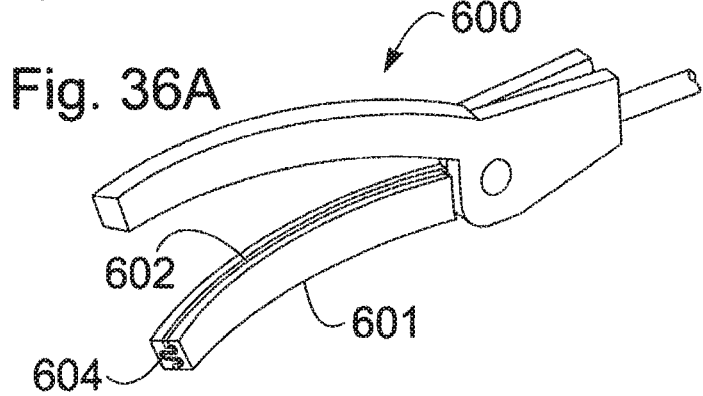
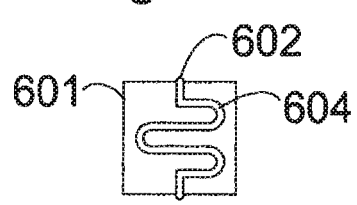
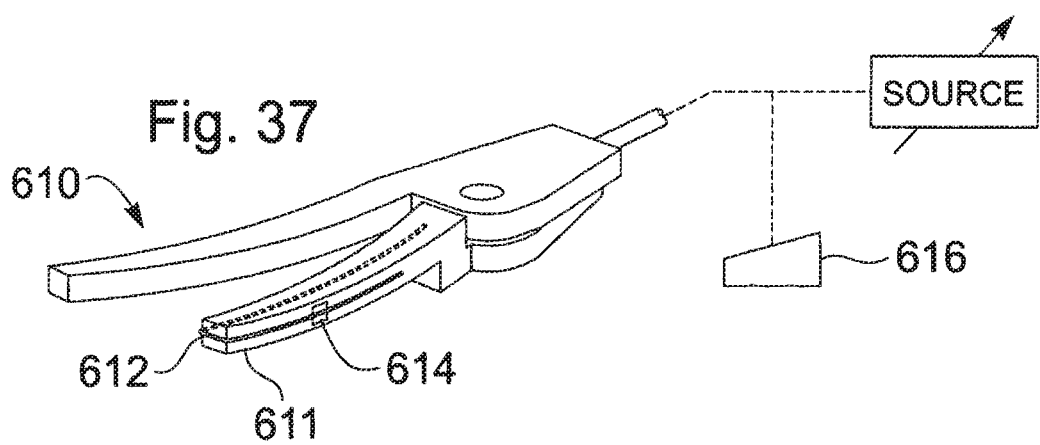

TISSUE WELDING AND CUTTING APPARATUS AND METHOD

RELATED APPLICATIONS

This application is a divisional of U.S. patent application Ser. No. 14/551,599 filed on Nov. 24, 2014 (now U.S. Pat. No. 9,636,163, issued on May 2, 2017), which is a divisional of U.S. patent application Ser. No. 13/494,985, filed Jun. 12, 2012, which issued as U.S. Pat. No. 8,894,638 on Nov. 25, 2014, which is a continuation of U.S. patent application Ser. No. 11/090,750, filed Mar. 25, 2005, now U.S. Pat. No. 8,197,472 issued on Jun. 12, 2012, the entire disclosures of which are expressly incorporated by reference herein. The present application is further related to U.S. Pat. No. 7,918,848, issued on Apr. 5, 2011, the entire disclosure of which is expressly incorporated by reference herein.

FIELD OF THE INVENTION

The present invention relates to surgical devices and methods for severing and sealing blood vessels and, in particular, to an endoscopic tissue welder.

BACKGROUND OF THE INVENTION

Endoscopic harvesting of vessels is well known in the surgical field and has been the subject of a great deal of recent technological advancement. Typically, the harvested vessel is used for bypass or as a shunt around an artery that has diminished flow from stenosis or other anomaly, such as a Coronary Artery Bypass Grafting (CABG) procedure. Often in CABG, a saphenous vein from the patient's leg is harvested for subsequent use in the surgery. Other vessels, such as the radial artery, can also be harvested and used in this manner. Vessel harvesting involves liberating the vessel from surrounding tissue and transecting smaller side branches, cauterizing, tying or ligating the vessel at a proximal site and a distal site, and then transecting the vessel at both sites before it is removed from the body.

Known endoscopic methods and devices for performing vessel harvesting are discussed in detail in U.S. Pat. No. 6,176,895 to Chin, et al., Re 36,043 to Knighton, U.S. Pat. No. 6,406,425 to Chin, et al., and U.S. Pat. No. 6,471,638 to Chang, et al., all of which are expressly incorporated herein by reference. Furthermore, various devices and methods disclosed in U.S. Pat. No. 5,895,353 to Lunsford, et al., and U.S. Pat. No. 6,162,173 to Chin, et al., and pending patent application Ser. No. 10/602,490 entitled "Apparatus and Method for Integrated Vessel Ligator and Transector" are also expressly incorporated herein by reference. Also, commercial vessel harvesting systems sold under the tradename VASOVIEW® Uniport Plus and VASOVIEW® 5 are available from Guidant Corporation of Santa Clara, Calif.

Numerous instruments are known which coagulate, seal, join, or cut tissue, and which are suitable, for example, for severing a target vessel from surrounding side branches and securing the separated ends to stanch bleeding. Such devices typically comprise a pair of tweezers, jaws or forceps that grasp onto and hold tissue therebetween. The devices may operate with a heating element in contact with the tissue, with an ultrasonic heater that employs frictional heating of the tissue, or with a mono- or bi-polar electrode heating system that passes current through the tissue such that the tissue is heated by virtue of its own electrical resistance. The devices heat the tissue to temperatures such that the tissue is either "cut" or "sealed", as follows. When tissue is heated in excess of 100° Celsius, the tissue disposed between the tweezers, jaws or forceps will be broken down and is thus, "cut". However, when the tissue is heated to temperatures between 50° to 90° Celsius, the tissue will instead simply "seal" or "weld" to adjacent tissue. In the context of the present application, the term "tissue welding" refers to procedures that cause otherwise separated tissue to be sealed, coagulated, fused, welded or otherwise joined together. Numerous devices employing the same general principle of controlled application of a combination of heat and pressure can be used to join or "weld" adjacent tissues to produce a junction of tissues or an anastomosis of tubular tissues.

Monopolar and bipolar probes, forceps or scissors use high frequency electrical current that passes through the tissue to be coagulated. The current passing through the tissue causes the tissue to be heated, resulting in coagulation of tissue proteins. In the monopolar variety of these instruments, the current leaves the electrode and after passing through the tissue, returns to the generator by means of a "ground plate" which is attached or connected to a distant part of the patient's body. In a bipolar version of such an electro-surgical instrument, the electric current passes between two electrodes with the tissue being placed or held between the two electrodes as in the "Kleppinger bipolar forceps" used for occlusion of Fallopian tubes. There are many examples of such monopolar and bipolar instruments commercially available today from companies including Valley Lab, Cabot, Meditron, Wolf, Storz and others worldwide.

A new development in this area is the "Tripolar" instrument marketed by Cabot and Circon-ACMI which incorporates a mechanical cutting element in addition to monopolar coagulating electrodes. A similar combined sealing and mechanical cutting device may also be known as a tissue "bisector," which merges the terms bipolar cautery and dissector. One tissue bisector is packaged for sale as an element of the VASOVIEW® Uniport Plus and VASOVIEW® 5 vessel harvesting systems by Guidant Corporation of Santa Clara, Calif.

In ultrasonic tissue heaters, a very high frequency (ultrasonic) vibrating element or rod is held in contact with the tissue. The rapid vibrations generate heat causing the proteins in the tissue to become coagulated.

Conductive tissue welders usually include jaws that clamp tissue therebetween, one or both of which are resistively heated. In this type of instrument, no electrical current passes through the tissue, as is the case for monopolar or bipolar cautery. Some tissue welders also perform a severing function without a mechanical knife. For example, the Thermal Ligating Shears made by Starion Instruments of Saratoga, Calif. is a, hand activated instrument that utilizes thermal welding to simultaneously seal and divide soft tissue during laparoscopic general surgery procedures. The Starion device uses a heating element at the tip of one of a pair of facing jaws combined with pressure to denature the protein molecules within the tissue. The denatured proteins bond together, forming an amorphous mass of protein, and fusing tissue layers together. The procedure can be used to fuse vessels closed. More highly focused heat may be applied in the center of the tissue within the jaws of the instrument, causing the tissue or vessel to divide, thus resulting in two sealed ends. A description of the Starion device is provided at www.starioninstruments.com.

Despite accepted means for severing and securing vessels, such as in a vessel harvesting procedure, there remains a need for an improved device that increases the operating efficiency of the device and ensures the least amount of trauma to surrounding tissue while simultaneously providing repeatable secure sealing of the severed vessel ends.

SUMMARY OF THE INVENTION

The present invention provides designs of tissue severing/sealing devices that control heat distribution within the distal jaws. In one embodiment, multiple heating elements are provided on one of the jaws of a tissue welding device. A primary heating element is positioned along the midline of the jaw length and is electrically connected to two secondary heating elements, one on each side of the primary heater. Electrical current passes through the primary heater and is then divided equally between the two secondary heaters. The electrical resistances of the three heating elements are designed such that the primary heater has the highest power dissipation (i.e., reaches the highest temperature), while the two secondary heaters have equal power dissipation but lower than that of the primary heater. This has the effect that the primary heater cuts tissue, while the secondary heaters seal or weld tissue. The three heating elements are separated by electrical insulation along their working lengths to prevent inadvertent contact, for example an air gap, silicone, or other such insulation.

The present invention provides a surgical apparatus for welding and severing tissue, comprising an elongated shaft having first and second relatively movable elongated jaws having jaw-facing surfaces attached to a distal end thereof. A first heating element for welding tissue and a second heating element for severing tissue are provided on the jaw-facing surface of the first jaw. The first heating element is adapted to heat up to a first temperature upon application of power, while the second heating element is adapted to heat up to a second temperature greater than the first temperature upon application of power so that the first heating element welds tissue while the second heating element cuts tissue. Desirably, the first heating element has a lower electrical resistance than the second heating element. Furthermore, the first heating element preferably has a wider profile than the second heating element in a plane transverse to the direction of elongation of the first jaw. Preferably, the first heating element has a lower profile relative to the second heating element in a direction toward the second jaw.

In a preferred embodiment, the second heating element extends generally centrally along the jaw-facing surface of the first jaw, and the first heating element comprises at least two welding members, one each on either side of the second heating element. The two welding members may be formed by a bifurcated segment of a one-piece heating element, the separated portions in the bifurcated segment being connected in parallel to a source of power. The first and second heating elements are desirably connected in series to a common source of power such that a current passing through one of the pair of welding members is about one half the current passing through the second heating element. Preferably, each of the welding members comprises a strip of material having a generally flat jaw-facing surface defining a lateral width, and the second heating element defines a cylindrical jaw-facing surface having a lateral width smaller than that of either of the welding members.

The second jaw may not include heating elements such that the first jaw is a "hot" jaw, and the second jaw is a "cold" jaw. A third heating element for welding tissue may also be provided on the jaw-facing surface of the first jaw. The third heating element is adapted to heat up to a temperature that is also lower than the second temperature (i.e., lower than a cutting temperature), and desirably to the first temperature, upon application of power. Preferably, a control handle is connected to a proximal end of the elongated shaft and has a control actuator mounted thereon for alternately separating and bringing together the jaw-facing surfaces of the elongated jaws. A force-limiting interface between the control actuator and the elongated jaws limits the magnitude of closing force of the jaws.

In accordance with one embodiment, the first jaw comprises a ceramic material having a thermal conductivity of less than 5.0 W/m-K. For example, the first jaw may comprise an inner member covered with the ceramic material. To reduce heat loss to the jaws, the inner member of the first jaw does not form a part of any electrical conduction path leading to either the first or second heating elements. The apparatus may further include a heat sink provided on the jaw-facing surface of one of the first or second jaws and positioned to influence lines of heat flux to remain within the jaws, and thermal insulation provided on the outboard side(s) of the heat sink.

The present invention also provides a surgical apparatus for welding and severing tissue, comprising first and second relatively movable elongate jaws having jaw-facing surfaces and an elongated shaft having the first and second relatively movable jaws attached to a distal end thereof. A first heating element for welding tissue is provided on the jaw-facing surface of one of the first or second jaws. A second heating element for severing tissue is provided on the jaw-facing surface of one of the first or second jaws. An electrical circuit path within the surgical apparatus includes a portion extending along the elongated shaft and through the first and second heating elements in series. Upon application of current through the electrical circuit path, the first heating element heats up to a first temperature and the second heating element heats up to a second temperature greater than the first temperature, so that the first heating element welds tissue while the second heating element cuts tissue.

In one preferred embodiment, the second heating element is provided on the jaw-facing surface of the second jaw, wherein the first heating element has a wider profile than the second heating element in a plane transverse to the direction of elongation of the first jaw. The first heating element desirably has a lower electrical resistance than the second heating element. Preferably, a control handle is connected to a proximal end of the elongated shaft and has a control actuator mounted thereon for alternately separating and bringing together the jaw-facing surfaces of the elongated jaws. A force-limiting interface between the control actuator and the elongated jaws limits the magnitude of closing force of the jaws.

Another aspect of the present invention is a surgical method of severing a target tissue while welding the severed ends. The method includes providing a surgical apparatus for welding and severing tissue including a pair of jaws adapted to open and close upon the target tissue, the jaws including first and second resistive heating elements. The jaws are closed upon target tissue and the first heating element is energized to a first temperature and for a sufficient period of time to form a welded region in the target tissue. The second heating element is also energized to a second temperature greater than the first temperature to sever the target tissue within the welded region. Preferably, step of electrically energizing the second heating element is performed after forming the weld in the target tissue. In a useful application of the surgical method, the target tissue is a target vessel, and the step of closing comprises transversely closing the jaws upon the target vessel.

A still further aspect of the present invention is a surgical apparatus for welding and severing tissue, comprising first and second relatively movable elongated jaws having jaw-facing surfaces. An elongated shaft supports the first and second relatively movable the jaws at a distal end thereof. An energy applicator is provided on the jaw-facing surface of the first jaw. The first jaw comprises a ceramic material having a thermal conductivity of less than 5.0 W/m-K to help reduce the amount of heat generated by the energy applicator that is lost to the jaws. The first jaw may consist essentially of the ceramic material, or may include an inner member covered with the ceramic material. Preferably, the inner member of the first jaw does not form a part of any electrical conduction path leading to the energy applicator. The ceramic material may be selected from the group consisting of alumina; machinable glass ceramic; zirconia; yttria; and partially stabilized zirconia.

Another aspect of the invention is a surgical apparatus for welding and severing tissue, comprising an elongated shaft having first and second relatively movable elongated jaws having jaw-facing surfaces attached to a distal end thereof. A first heating element is provided on the jaw-facing surface of the first jaw, and is adapted to heat up to a first temperature upon application of power. The first heating element is made of or is placed in electrical series contact with a temperature regulating material whose electrical resistance is not constant over a predetermined temperature range including the first temperature. In one embodiment, the temperature regulating material is a Positive Temperature Coefficient of Resistance (PTCR) material having an electrical resistance that will increase with increasing temperature such that the rate of temperature increase upon application of power slows down as the temperature of the temperature regulating material nears the first temperature. In an alternative embodiment, the temperature regulating material is a Polymer Positive Temperature Coefficient (PPTC) material having an electrical resistance that rapidly increases as the temperature of the temperature regulating material nears the first temperature. The apparatus may include a circuit that loops through the first heating element and through a device made of the temperature regulating material. In one exemplary construction, the temperature regulating material is formed into a rod-like element which is surrounded by a tubular layer of electrical insulation, and wherein the first heating element comprises an outer tube closely surrounding the electrical insulation.

In accordance with a still further aspect, a surgical apparatus for welding and severing tissue, comprising an elongated shaft having first and second relatively movable elongated jaws having jaw-facing surfaces attached to a distal end thereof. An energy applicator for welding tissue is provided on the jaw-facing surface of the first jaw, and a fasciotomy cutter is provided on one of the jaws. For example, the fasciotomy cutter comprises a knife blade on an exterior surface of one of the jaws. Alternatively, the energy applicator comprises a first heating element for welding tissue provided on the jaw-facing surface of the first jaw and adapted to heat up to a first temperature upon application of power, and the fasciotomy cutter comprises an extension of the first heating element that wraps around a distal tip of the first jaw. The first jaw may comprise a longitudinal main portion and a sloped distal end and wherein the first heating element extends along the main portion and then slopes downward to the distal end. In this construction, the fasciotomy cutter comprises a narrowed portion of the first heating element at the sloped distal end of the first jaw. Desirably, the sloped distal end of the first jaw comprises a pronounced rib around which the first heating element conforms. Alternatively, the fasciotomy cutter comprises a heating element provided on one of the jaws and supplied with power through a different circuit than the energy applicator.

Another aspect of the invention is a surgical apparatus for welding and severing tissue, comprising first and second relatively movable elongate jaws having jaw-facing surfaces that are provided on the distal end of an elongated shaft. An energy applicator for welding tissue is provided on the jaw-facing surface of the first jaw, and a resistance welder is provided on one of the jaws. In accordance with one embodiment, the energy applicator comprises a first heating element for welding tissue provided on the jaw-facing surface of the first jaw and adapted to heat up to a first temperature upon application of power, and the resistance welder comprises an extension of the first heating element that wraps around a distal tip of the first jaw. Preferably, the resistance welder has a surface area per length that is larger than the surface area per length of the first heating element for welding tissue. Alternatively, the resistance welder comprises a heating element provided on one of the jaws and supplied with power through a different circuit than the energy applicator.

BRIEF DESCRIPTION OF THE DRAWINGS

FIGS. 1A-1C are perspective views of a modular handle unit of a vessel harvesting system including a sled/adapter that permits a multipurpose handle base of the system to receive a tissue severing/welding device of the present invention;

FIG. 4 is an exploded perspective view of the distal end of the tissue severing/welding device of FIGS. 2A-2B;

FIGS. 5A-5B are perspective views of a "hot" jaw used in the exemplary tissue severing/welding device of the present invention;

FIGS. 6A-6B are enlarged perspective views of a proximal subassembly of the "hot" jaw of FIGS. 5A-5B;

FIGS. 7A-7C are perspective views of an exemplary heating element subassembly of the "hot" jaw of FIGS. 5A-5B;

FIGS. 8A-8H are perspective, plan, and elevational views of an exemplary inner jaw forming a portion of the "hot" jaw of FIGS. 5A-5B;

FIGS. 9A-9E are perspective, plan, and elevational views of an exemplary heating element for welding tissue used in the "hot" jaw of FIGS. 5A-5B;

FIGS. 10A-10H are perspective, plan, and elevational views of an exemplary boot for covering the inner jaw of FIGS. 8A-8H;

FIG. 15 illustrates in cross-section a "hot" jaw spaced from a "cold" jaw similar to those shown in FIGS. 5A-5B;

FIGS. 16A-16B show variations on the "hot" jaw of FIG. 15;

FIG. 17 illustrates another possible variation on a hot jaw of the present invention having only one heating element and a conductive plate for absorbing heat and welding tissue;

FIGS. 18A-18C illustrate alternative jaw configurations in cross-section that again includes multiple heating elements distributed on both jaws;

FIGS. 24A-24C illustrate three different alternative embodiments of tissue welding jaws that incorporate a material within the boots and adjacent the heating element that provide a "hot zone" for welding;

FIG. 25 illustrates a still further alternative embodiment of the present invention with multiple heating elements concentrically arranged in a hot jaw;

FIGS. 26A and 26B are schematic views of an exemplary tissue welder having a fasciotomy cutter;

FIGS. 34A, 34B, 35A, 35B, 36A, 36B and 37 illustrate a number of designs of tissue welder jaws having localized heaters on the distal end of one of the jaws.

DESCRIPTION OF THE PREFERRED EMBODIMENTS

Figure 2A:
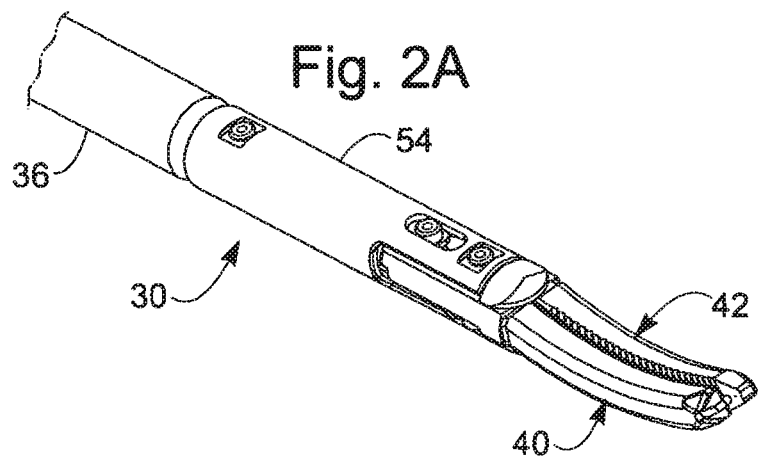
FIGS. 2A-2B are perspective views of the distal end of an exemplary tissue severing/welding device of the present invention showing a pair of clamping jaws in their closed position.
Figure 2B:
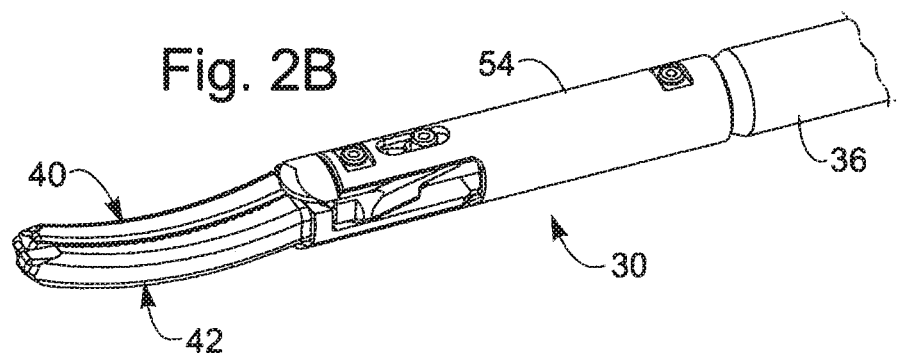

According to one aspect of the present invention devices and methods for sealing, or coagulating, and severing tissue during surgery are provided. The instruments incorporate means for controllably heating tissue while simultaneously applying a definite and controllable amount of pressure to the tissue being heated. Because of the combined application of heat and pressure, tissue proteins will become coagulated and blood vessels within the tissue will be sealed shut, achieving hemostasis. Optimal sealing or coagulating tissue means producing a strong and durable seal or coagulation or anastomosis with a minimal amount of collateral tissue damage.

One aspect of the present invention includes a method and system for the surgical treatment of biological tissue, wherein thermal energy and pressure are applied simultaneously, substantially simultaneously, consecutively, or alternatively, over a time such that tissue proteins are denatured and the tissue will adhere or join to itself or to other tissues, for the purpose of coagulating bleeding, sealing tissue, joining tissue and cutting tissue. The minimum amount of heat or thermal energy needed to accomplish these goals is expended, so as to minimize thermal damage to tissue adjacent to the treated site.

The devices of the invention may also incorporate means for cutting, or severing the tissue. "Severing" includes dissecting or tissue division, tissue disruption or separation, plane development, or definition, or mobilization of tissue structures in combination with a coagulation, or hemostasis or sealing of blood vessels or other tissue structures such as lymphatics, or tissue joining. Severing can be achieved by use of amounts of heat greater than the amount required to coagulate the tissues, yet a minimum amount of energy is used with the least amount of unwanted tissue necrosis. In conjunction with some aspect of the invention, severing can be achieved by other mechanical, ultrasonic, or electronic means, including, but not limited to, shearing action, laser energy, and RF, or a combination of two or more of the above. For example, a blade may be passed through the coagulated tissue while the tissue is being held in the jaws of the instrument.

The present invention desirably provides a tissue welder that can be incorporated as a component of an integrated vessel harvesting system, such as is disclosed in application Ser. No. 10/951,426, filed Sep. 28, 2004, which is expressly incorporated herein by reference. The vessel harvesting system is especially useful in minimally invasive endoscopic harvesting of blood vessels, including harvesting of internal thoracic artery, or vessels of the extremities along the radial artery in the arm for use in coronary artery bypass grafting, and the saphenous vein in the leg for use in both coronary artery bypass grafting and peripheral artery bypass. In this context, the tissue welder performs both a severing and securing/welding function in separating side branches from the target vessel that is being harvested. It should be understood, however, that various aspects of the tissue welder described herein may be utilized in conjunction with other surgical systems for coagulating and/or dissecting tissue.

The exemplary embodiment of the tissue welder of the present invention comprises a so-called "welding and severing device" that is used to close off and separate side branches from a primary vessel being harvested, and also possibly to sever the primary vessel. However, the device is disclosed herein are suitable for welding and severing tissue in general not just vessels. In its broadest sense, the term tissue welding and severing device refers to any and all devices that accomplish a single function or any combination of the functions of welding, ligating, cauterizing, coagulating and/or sealing, and severing or transecting target tissue. For example, electrocautery tools such as bipolar scissors (or other plural electrode-based devices), monopolar devices, tissue bisectors, or other such devices provide these functions alone or in conjunction with an integral blade or cutter. Other similar devices using various acceptable sources of energy for sealing the tissue (for example, RF, microwave, laser, ultrasound, direct thermal energy, etc.) are also within the scope of the present invention. Each device that acts on tissue to either weld or sever it will be termed an energy applicator. The welding and severing device could be a single tool or a combination of plurality of separate tools each having its own function useful in tissue severing, or more specifically in vessel harvesting.

Parenthetically, it is important to note that, while each of the various aspects of the present invention may be used to advantage in combination with the other aspects, each is believed to also be of patentable significance when used alone with otherwise conventional systems and techniques. Thus, the tissue welding devices and methods may be implemented using heating and control structures other than those disclosed herein, and in the context of systems other than those for vessel harvesting. Furthermore, various aspects of the tissue welder disclosed herein may be utilized with other welding and severing devices, such as bipolar scissors or tissue bisectors. Similarly, certain aspects of the coagulation function of the tissue welder may be combined with a mechanical cutter to provide the severing function.

Finally, it should be understood that the exemplary and/or alternative tissue welders and features described herein have numerous applications in addition to vessel harvesting. For example, a tissue welder may be utilized in gastric bypass surgery to resect and close a portion of the stomach. Similarly, volume reduction of the lungs in patients with emphysema can also be accomplished with the devices disclosed herein. Bowel resection is another potential application. Other surgical procedures include: femoral popliteal bypass; severing/ligating epigastric arteries for gastric reflux disease; fallopian tube ligation; vasectomies; severing/ligating arteries, veins, and bile ducts in gallbladder removal surgery; and nephrectomies where the ureters leading to the kidney are transected and ligated.

FIGS. 1A-1C illustrate a modular handle unit 20 of an exemplary vessel harvesting system comprising a mating handle base 22 and handle sled 24. The handle base 22 includes a distal flange 26 secured to an elongated cannula 28. The cannula 28 is sized to extend into a body cavity and provides a channel for various vessel harvesting tools. The handle sled 24 includes structure for mating with the handle base 22, as seen in FIG. 1A. Various modular handle units and vessel harvesting systems are illustrated and described in aforementioned application Ser. No. 10/951,426, filed Sep. 28, 2004.

In the particular embodiment of FIGS. 1A-1C, the handle sled 24 provides an adapter for multipurpose handle bases common to a number of vessel harvesting systems, such that a tissue welding and severing device 30 of the present invention may be used for vessel harvesting within the system. Specifically, the handle sled or adapter 24 provides a port 32 leading to an internal angled channel 34 through which the elongated shaft 36 of the welding and severing device 30 may extend. The handle base 22 and handle sled 24 couple such that the elongated shaft 36 is guided through the distal flange 26 and harvesting cannula 28. The final assembly as seen in FIG. 1C shows that some of the movement controls for the harvesting tools are located on the handle unit 20, while rotation of the welding and severing device 30 is accomplished by manipulating the entire handle 38 relative to the sled 24 with a second hand.

FIG. 1C also illustrates an enlarged distal end of the cannula 28 through which a distal end of the tissue severing/welding device 30 projects. The device 30 comprises a pair of relatively movable elongated jaws 40, 42 on its distal end, which are shown open. Preferably, a mechanism within the handle 38 includes an actuator 44 for opening and closing the jaws 40, 42. The jaws 40, 42 are elongated generally in a proximal-distal direction such that they are much longer in that direction than in either orthogonal or transverse axis.

It should be understood that the term "jaw" refers to a member that may be brought together with another similar member or other structure such that jaw-facing surfaces on both members are brought into contact or close proximity. A jaw may be provided on a clamp, tweezers, forceps, or similar grasping tools. The jaws 40, 42 are mounted such that their proximal ends are journalled about common or different but closely spaced pivots and their distal ends open and close. Of course, the jaws may be mounted for parallel movement instead of in a pivoting action. An exemplary embodiment of the present invention includes a "hot" jaw and a "cold" jaw, the difference being that only one jaw is actively heated. It should be emphasized, however, that certain aspects of the present invention are applicable to different jaw configurations, such as both being "hot" jaws, or both being "cold" jaws with a separate source of heat.

In a preferred embodiment, the first jaw 40 comprises a "hot" jaw, while the second jaw 42 is a "cold" jaw. The term "hot" refers to the presence of at least one active heating element thereon, while a "cold" jaw provides no active heating (but may become hot from indirect heating by the other jaw). In the illustrated embodiment, as seen in FIG. 1C, the first or "hot" jaw 40 includes a first heating element 46 for welding tissue and a second heating element 48 for severing tissue. The first heating element 46 is adapted to heat up to a first temperature upon application of current therethrough, while the second heating element 48 is adapted to heat up to a second temperature upon application of current therethrough which is greater than the first temperature. Conventional understanding is that when vascular tissue is heated in excess of 100° C., the tissue will be broken down and is thus, "cut". However, when vascular tissue is heated to temperatures between 50 to 90° C., the tissue will instead simply "seal" or "weld" to adjacent tissue.

Various means are described herein for ensuring that the first heating element 46 heats up to within a welding temperature zone but not to a cutting temperature threshold, while the second heating element 48 heats up past the welding temperature zone into the cutting temperature zone. For example, the relative electrical resistance values of the first and second heating elements 46, 48 may be such that they heat up to different temperatures. Alternatively, the materials used may be the same, but the first and second heating elements 46, 48 may be shaped in a manner that causes their differential heating. Still further, the current passed through the two heating elements may be unequal.

Figure 3A:
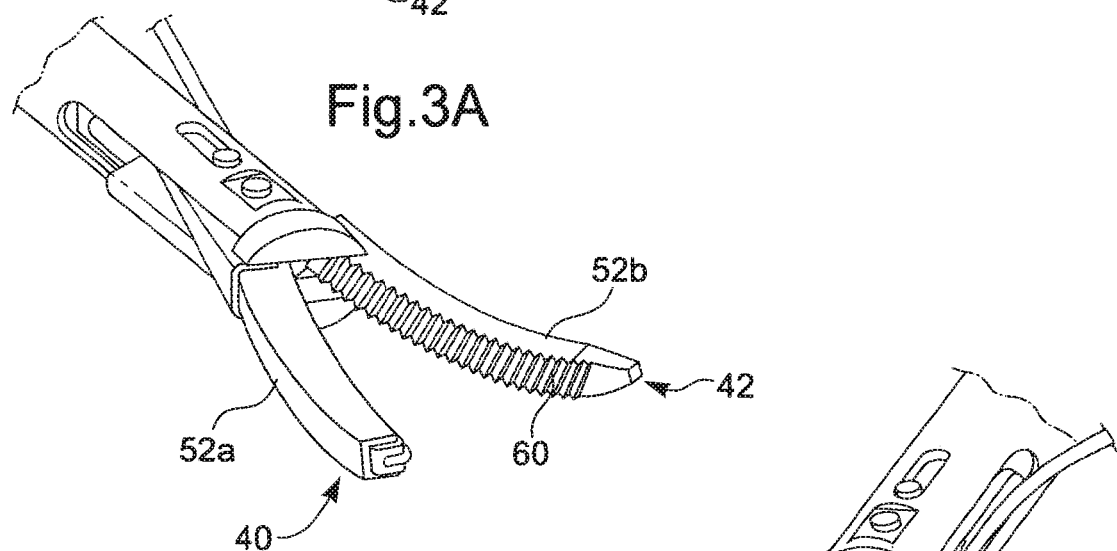
FIGS. 3A-3B are perspective views of the distal end of the tissue severing/welding device of FIGS. 2A-2B showing the clamping jaws in their open position.

FIG. 1C also basically illustrates a preferred configuration of the jaws 40, 42 and a distal end of the shaft 36 extending through a distal end of the elongated cannula 28. In particular, the jaws 40, 42 are arranged to pivot apart about a common axis, represented by pivot pin 50. An exemplary mechanism for opening and closing the jaws 40, 42 will be described in detail below. Each of the jaws 40, 42 includes an inner jaw member of rigid material and a boot 52a, 52b (as seen in FIG. 3A) surrounding the inner jaw member that is made of the material that resists tissue adhesions during operation of the device. In one embodiment, the inner jaw members are made of stainless steel, but other materials that provide less of a heat sink may be used. Preferably, the boots 52a, 52b are made of a heat-resistant silicone rubber. The boots 52a, 52b also provide some thermal insulation around the inner jaw members to reduce heat losses thereto. The first and second heating elements 46, 48 are arranged external to the boot 52a on the first jaw 40, in particular on a surface of the jaw that faces the other jaw.

FIGS. 2-7 provide a number of assembled, exploded, and other partial views of the distal end of an exemplary tissue welding and severing device 30 of the present invention. In FIGS. 2A-2B, the jaws 40, 42 are shown closed at the distal end of the welding and severing device 30. The device 30 includes a generally tubular distal tip 54 that fits on the end of the device shaft 36 and houses a mechanism (described below) for opening and closing the jaws 40, 42. Both jaws 40, 42 exhibit a shallow curvature along their lengths such that their jaw-facing surfaces contact along a curved line. In a preferred embodiment, the entire distal assembly of the device 30 including the jaws 40, 42 is sized to fit through a 5 mm diameter port, thus enabling use in minimally invasive surgery.

The jaws 40, 42 preferably incorporate a multiple heater welding system on a "hot" jaw 40. At a minimum, at least two heating element are provided, with one heating element adapted to sever tissue and a second heating element adapted to weld or coagulate tissue. In an exemplary embodiment, the jaw 40 incorporates a "tri-heater" arrangement with one heating element for cutting and two heating elements for welding disposed on either side of the cutter. Desirably, the heating elements extend longitudinally from a proximal to a distal end of the jaw 40, with the cutter generally centrally located and the two welders symmetrically located on either side.

Figure 3B:
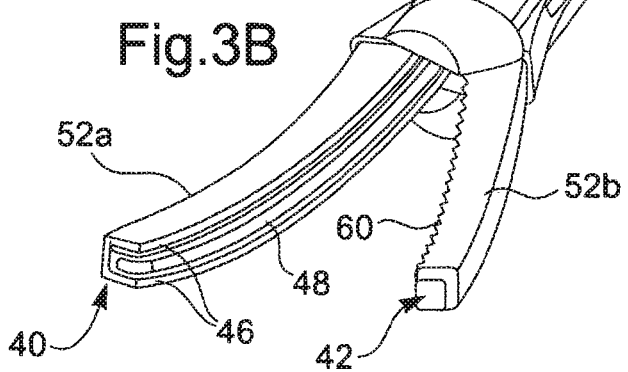

FIGS. 3A-3B illustrate the jaws 40, 42 in their open configuration. As can be seen in FIG. 3B, the first heating element 46 is preferably bifurcated into two welding members separated laterally, with a single second heating element 48 provided therebetween. The bifurcated welding members of the first heating element 46 each provide a weld region within the tissue, while the second heating element 48 cuts the tissue within the weld region. Technically, therefore, the hot jaw 40 includes three heating elements: a central cutting element and two adjacent welding elements. Although the exemplary embodiment combines the two adjacent welding elements in a single piece, they could easily be constructed separately. As mentioned above, one or both jaws 40, 42 include inner jaw members surrounded by a boot 52a, 52b. The boot 52b around the second jaw 42 is preferably provided with a series of lateral serrations 60 that facilitate gripping and prevent slipping of the tissue when clamped between the jaws. Because of the presence of the first and second heating elements 46, 48 on the exterior of the boot 52a on the first jaw 40, no serrations are necessary.

FIG. 4 shows the components of the distal end of the device 30 exploded, while FIGS. 5-7 best illustrate the specific shapes and subassembly of the first and second heating elements 46, 48, and how they mount on and cooperate with the first jaw 40. The inner jaw member 62 (seen isolated in FIGS. 8A-8H) of the first or "hot" jaw 40 comprises an elongated and curved distal portion 64 and a proximal pivot housing 66, including through holes for pivotal movement with respect to the other jaw. More specifically, the proximal pivot housing 66 of the inner jaw member 62 includes a large circular through hole 67 and an angled slot 68, both formed in an outer wall section 69. A pair of sidewalls 70 upstanding from the outer wall section 69 provide a space on the inner side of the pivot housing 66 within which electrical wires and a pivot mechanism are received, as explained below.

The first heating element 46 comprises a proximal crimp 72 and flange 73. Two elongated welding members 74 extend from the proximal crimp and flange in a distal direction and curl back upon themselves to terminate at a common barb 75 (see FIG. 7B). The elongated welding members 74 preferably comprise thin, rectangular strips each having a lateral width W that extend in parallel across a spaced distance S. Because the welding members 74 are connected at their proximal ends by the crimp 72 and flange 73 structure, and at their distal ends by the common barb 75, they define a bifurcated portion of the first heating element 46. In a preferred embodiment, the first heating element 46 comprises a single, homogeneous piece of metal (e.g., stainless steel) that has been formed into the illustrated shape by stamping, bending, machining, etc.

The second heating element 48 extends between and in parallel with the spaced welding members 74 and is separated therefrom by air gaps. The heating element 48 also extends in a distal direction the same length as the welding member 74 and curls back upon itself to terminate at a connection end 76 adjacent the barb 75 (see FIG. 7B). The connection end 76 and barb 75 are electrically connected using a resistance or spot weld, for example. In the context of the present application, the term "resistance weld" used to describe the joint between two mechanical parts encompasses all suitable varieties of such joints, including for example, spot welds, laser welds, soldered joints, brazed joints, etc.

As seen in the exploded view of FIG. 4, the heating element 48 may comprise an elongated wire or rod, and the connection end 76 may be formed by a separate U-shaped coupling 77 forming a series extension thereon. The second heating element 48 has a raised profile relative to the first heating element 46 in a direction toward the second jaw 42. This enhances the differential ability of the second heating element 48 to cut through tissue while the first heating element 46 welds. Furthermore, the strip-like welding members 74 of the first heating element 46 each have flat jaw-facing surfaces, while the second heating element 48 defines a cylindrical jaw-facing surface having a lateral width smaller than that of either welding member.

An exemplary first heating element 46 is seen isolated in FIGS. 9A-9E. These illustrations show a heating element 46 that is slightly different than the one shown in preceding figures, although either may be used with good results. The difference is in the distal end which exhibits a flange 78 that is bent, for example, at 90.degree. instead of curling back into the barb 75 toward the proximal end. The flange 78 is forked to define a generally semi-circular opening 80 that receives the second heating element 48. Although not shown, in this version the second heating element 48 curls 180.degree. into the opening 80 and is secured in electrical contact therewith using a resistance weld, for example.

Now with specific reference to FIGS. 5-7, the heating elements 46, 48 are shown having conductor wires attached thereto to form a series circuit. As seen in FIGS. 6B and 7A, a pair of insulated conductor wires 82, 84 form part of a circuit path through the heating elements 46, 48. The first conductor wire 82 is in electrical communication with the first heating element 46 by virtue of a resistance weld at the proximal crimp 72, while the second conductor wire 84 is in electrical communication with the second heating element 48. An insulated sleeve around the second conductor wire 84 extends through an aperture formed in the flange 73 of the first heating element 46. The barb 75 and connection end 76 are electrically connected such that the first and second heating element 46, 48 define a current loop all along the length of the jaw 40.

Current through the conductors 82, 84 therefore passes in series through the first and second heating elements 46, 48. Current through the two heating elements 46, 48 remains separated to the common distal end thereof, and in particular to the resistance weld between the barb 75 and connection end 76. Because of the bifurcation of the first heating element 46 into the separate welding members 74, each of the welding members 74 conducts in parallel approximately half of the current that passes through the second heating element 48. It should be understood, therefore, that if the heating elements are identical in shape and material, each welding member 74 would heat up to a temperature less than that which the second heating element 48 attains because of the split current. This differential helps ensure that the first heating element 46 reaches the welding zone temperatures, while the second heating element 48 reaches temperatures within the cutting zone. In the illustrated embodiment, the separate welding members 74 each have a wider profile (i.e., larger surface area) facing the tissue in a plane transverse to the direction of elongation of the jaw 40 than does the second heating element 48. This structural difference in conjunction with the lower current and thus lower temperature helps facilitate a welding action on the tissue as opposed to a cutting action, in contrast to the central heating element 48 which is both narrower and hotter (and raised up higher).

Advantageously, however, the second heating element 48 is constructed so as to have a higher electrical resistance than either of the welding members 74, and therefore even more of the already larger current dissipates as heat. This combined phenomena of higher current and higher resistance causes the second heating element 48 to heat up to a cutting temperature zone, while the first heating of the 46 only reaches temperatures in the tissue welding zone. In a preferred embodiment, the first heating element 46 is made of a suitable conductive metal such as 301 stainless steel, while the second heating element 48 comprises a tube of rigid material with filler having a higher magnitude of electrical resistance than the tube, the combination having an electrical resistance greater than stainless steel. In one specific embodiment, the tube is made of a nickel-chromium alloy such as INCONEL 625 and is filled with an electrically insulating but thermally conductive ceramic such as magnesium oxide (MgO) powder. Consequently, a greater current density passes through the hollow tube than if it were solid, and therefore the material reaches a higher temperature at any given current. Additionally, the inner thermally conductive ceramic does not unduly restrict conductive heat flow through the element 48. Preferably, the second heating element 48 has a relatively high resistance of about 0.2 Ohms, and the entire system of the first and second heating elements has an average resistance of about 0.72 Ohms, and preferably less than 0.8 Ohms.

It is important to understand that the present invention contemplates at least one cutting element and at least one welding element, electrically connected in series or not. For example, the illustrated embodiment may be modified by utilizing two current paths, one for the first (welding) heating element 46 and one for the second (cutting) heating element 48. Alternatively, one cutting element and a single (i.e., not bifurcated) welding element may be provided on the hot jaw, both forming a part of a common current path. Finally, the same arrangement can be utilized with separate current paths. Moreover, as mentioned above, the cutting element may be provided on one jaw while the welding element is provided on the opposite jaw. In each of these alternative configurations, the common denominator is that upon application of a common or separate currents, the cutting element reaches a higher temperature than the welding element.

FIGS. 10A-10H show a number of views of an exemplary boot 52*a* used on the "hot" jaw 40. As mentioned above, the boot 52*a* is made of material such as silicone rubber that resists tissue adhesions, and thus facilitates multiple tissue severing/welding operations prior to a reduction in the effectiveness of the jaws because of such tissue adhesions. The boot 52*a* provides electrical insulation between the heating elements 46, 48, and also provides thermal insulation, thus helping to retain heat to the space between the jaws as opposed to being lost to the often metallic inner jaws 62. The boot 52*a* generally comprises a hollow sleeve having an open proximal end 86 and a partially closed distal end 88. An upper surface 90 that faces the cold jaw 40 when the boot 52*a* is mounted on the hot jaw 40 includes a pair of longitudinally-oriented rails 92. As seen in FIGS. 10D and 10G, the rails 92 are generally evenly spaced apart and provide guide channels for the bifurcated first heating element 46 and the central second heating element 48. The distal end 88 of the boot 52*a* has an opening into which extend the joined and curled or bent distal ends of the two heating elements 46, 48. This holds the distal ends of the two electrodes on the hot jaw 40. It should be noted that the distal end of the inner jaw member 62 has a forked depression as seen at 93 in FIG. 7C. The insulating boot 52*a* is molded so that it has an inside shape which conforms within this depression 93, and also provides an outwardly opening cavity to receive the joined barb 75 and connection end 76. The arrowhead shape of the barb 75 helps secure the heating elements in place with respect to the soft insulating boot 52*a*, which, again, is preferably silicone rubber.

FIGS. 5-6 illustrate the integration of the combined heating elements 46, 48 and conductor wires 82, 84 into the inner jaw member 62. As seen best in FIG. 6B, the proximal crimp 72 secures the first heating element 46 and an extension of the silicone boot 52*a* to an upstanding flange 94 of the pivot housing 66. The conductor wires 82, 84 are routed through the space in the pivot housing 66 formed by the pair of sidewalls 70. The first conductor wire 82 extends straight along one side wall 70 and is resistance welded or otherwise secured to the proximal crimp 72 of the first heating element 46. The second conductor wire 84 follows a bent path along the other side wall 70 and passes through the aforementioned aperture formed in the proximal flange 73 of the first heating element 46, as seen in FIG. 6A. FIG. 5B shows a bushing 96 having an upstanding shaft stub 98 assembled over the pivot housing 66. The bushing 96 forms a part of a mechanism for opening and closing the jaws 40, 42, and will be more clearly described below.

One aspect of the present invention that facilitates assembly and thus reduces fabrication cost, is the integrated nature of the heating element subsystem. The subsystem is seen in FIGS. 6B and 7A, and consists of five parts: the first heating element 46, the second heating element 48, the pivot housing 66 (typically fabricated integral with the first inner jaw 62), and the two wires 82 and 84 that provide current through the series heating elements. These five parts are held together with several crimps, or desirably resistance welds, or both, and may be easily assembled prior to integration with the rest of the hot jaw 40.

As mentioned above, either or both of the jaws 40, 42 includes an inner jaw member covered with a boot. The exploded view of FIG. 4 shows both the inner jaw member 62 of the hot jaw 40, and an inner jaw member 102 of the second or "cold" jaw 42, along with the associated boots 52*a*, 52*b*. Both boots 52*a*, 52*b* fit over and surround the curved distal portions of the inner jaw members 62, 102, respectively.

In prior tissue welders, stainless steel inner jaw members were conveniently used as the return conduction path for the current passing through one or more electrodes. This had a distinct disadvantage in that some of the current was dissipated as resistance heat generated within the inner jaw member. This also had a disadvantage of heat conduction from heating element into jaw that resulted in less efficient energy delivery to tissue and potential inadvertent thermal injury. In one aspect the present invention not only physically decouples the heating elements 46, 48 from the first inner jaw member 62, in that a layer of the insulating boot 52*a* is interposed therebetween, but no current runs through the inner jaw member. The series connection between the distal barb 75 and connection end 76 means that the entire electrical conduction path along the hot jaw runs only through the heating elements 46, 48. In this way, the efficiency of conversion of electrical energy into desirable resistance heat is maximized, and the footprint of the device on tissue other than that directly in contact with the heating elements is minimized.

In addition to being able to weld and sever tissue, and in particular blood vessels, the jaws 40, 42 may also be capable of performing fasciotomy, or an incision through fascia (e.g., bands or fillets of fibrous tissue that separate different layers of tissue). As seen best in FIG. 3B, where the jaws 40, 42 are shown open, the second heating element 48, the "cutter wire," extends the full-length of the jaw along its midplane. In addition, it is positioned so as to be raised upward from the surrounding weld members of the first heating element 46 and thus presents the first surface of the hot jaw 40 to contact tissue received within the jaws. Fasciotomy can be performed by merely pushing the open jaws through a band of tissue with the second heating element 48 energized such that it cuts the tissue by heating it above the cutting temperature. Of course, in the exemplary embodiment the first heating element 46 also heats up, although this will have negligible impact on the fasciotomy procedure.

FIG. 4 also illustrates a tapered tip 103 on the distal end of the inner jaw member 102 of the second or "cold" jaw 42. This tip 103 helps facilitate blunt dissection of tissue when the device is used as such. The surrounding boot 52*b* will have a similar taper. In a preferred embodiment, the inner jaw member 102 has a generally rectangular cross-section, and the tip 103 has two tapers provided on the opposite straight sides. Of course, other arrangements such as a more rounded cross-section and a conically-tapered tip 103 may be substituted. Moreover, the inner jaw member 102 of the cold jaw 42 is slightly longer than the more blunt inner jaw member 62 of the first jaw 40 to further ease dissection of tissue.

Attachment of the jaws 40, 42 to the distal end of the tissue welder shaft 36, and an exemplary mechanism for opening and closing the jaws will now be described. With reference to the exploded view of FIG. 4, and also to FIGS. 3 and 5, the pivot housing 66 of the first inner jaw member 62 comes together with a proximal pivot housing 104 of the second inner jaw member 102, capturing the bushing 96 therebetween. The bushing 96 includes oppositely directed shaft stubs 98 that fit within the aligned apertures formed in the pivot housings 66, 104, such as the aperture 67 seen in FIG. 6B. The bushing 96 includes features on one side that mate with the particular shape of the pivot housing 66 and conductor wires 82, 84 arranged therein. In this regard, the bushing 96 is fixed with respect to the pivot housing 66 of the first inner jaw member 62. The pivot housing 104 of the second inner jaw member 102, on the other hand, includes a flat lower surface that slides across a flat upper surface of the bushing 96 when the housing pivots about the shaft stub 98. Consequently, the first inner jaw member 62 and second inner jaw member 102 are permitted to pivot with respect one another about the shaft stubs of the bushing 96.

The exploded view of FIG. 4 also shows the distal end of the flexible shaft 36 which includes a stepped-down portion 110. The flexible shaft 36 is hollow and receives a control rod 112 therethrough. A generally Y-shaped yolk 114 attaches to the distal end of control rod 112 through a resistance weld or similar expedient (not shown). Linear movement of the control rod 112 therefore also moves the yolk 114. The generally tubular shaft tip 54 fits over the stepped-down portion 110 and is secured thereto with a rivet 118.

With reference primarily to FIG. 4, but also FIGS. 2 and 3, the tubular shaft tip 54 includes a bifurcated distal end having a pair of arms 120 defining side openings 122 therebetween. As will be explained, the pivot housings 66, 104 of the jaws extend between the arms 120 and the side openings 122 permit pivotal movement thereof. The assembly of the two pivot housings 66, 104 with the bushing 96 therebetween is sandwiched between a pair of small spacers 124 that have flat inner surfaces and partial cylindrical outer surfaces. The spacers 124 include through bores that align with the apertures 67 in the pivot housings and with the inserted shaft stubs 98. The jaw assembly including spacers 124 then fits between the bifurcated arms 120 and is secured therein with a rivet 126 that passes through a pair of apertures 128 in the fingers, and through the aforementioned apertures. The jaws 40, 42 therefore pivot about the shaft stubs 98.

Both of the pivot housings 66, 104 include the angled slots 68 that are generally aligned with elongated slots 130 formed in both of the arms 120 of the shaft tip 54. As seen in the exploded view of FIG. 4, the angled slots 68 are oppositely oriented with respect to one another. The combined thickness of the assembled pivot housings 66, 104 fits between the bifurcated fingers of the yolk 114 and a rivet 132 passes through apertures in the distal ends of the yolk fingers and through the angled slots 68. In this way, linear movement of the yolk 114 translates into linear movement of the rivet 132, which in turn opens and closes the jaws 40, 42 through a camming action in the angled slots 68. The elongated slots 130 provide clearance for the rivet heads, ensure planar alignment of the rivets, and also facilitate assembly thereof. With the angled slots 68 oriented as shown, the jaws will be open when the control rod 112 is displaced distally, while proximal movement of the control rod closes the jaws.

Electricity can be delivered to the jaws 40, 42 through the conductor wires 82 and 84, best shown in FIG. 6B, or directly through the pivoting mechanism just described. For example, the control rod 112 may be electrically conductive and provide current to the inner jaw members and 62, 102 via the connecting the yolk, pins, and angled slots. The return current path might be provided by a single conductive wire. The illustrated embodiment utilizing conductor wires 82, 84 is preferred because it eliminates moving parts from the electrical conduction path.

Within the constraints of the small diameter design (less than 5 mm), the jaw movement mechanism should be relatively robust to be capable of applying a closing force of around 1-3 lb, preferably about 1 lb, and an opening force of around 1-3 lb. Further, the jaw opening distance at the distal tips thereof is desirably about 8 mm. In addition to welding and cutting tissue, the jaws can also be used for blunt dissection because of the tapered and rounded outer shape of the jaws. This blunt dissection can also be enhanced by the relatively robust opening force provided by the jaws.

As will be apparent, the jaw opening and closing function can be achieved in many different ways. The present invention, in its broad interpretation, is not particularly limited to any one type of mechanism. For example, instead of both jaws pivoting about a common axis, a series of linkage members may be utilized with the jaws pivoting about spaced axes. The form of jaw opening apparatus is preferably chosen to minimize cost and optimize transfer of linear force to pivoting movement of the jaws. Optionally, the pivoting mechanism is configured such that the jaw-facing surfaces of the jaws remain parallel.

An exemplary control handle 38 seen in FIGS. 11A-11C and 12 contains a mechanism for actuating the control rod 112 and opening and closing the jaws, in addition to several other desirable features. The control handle 38 is seen in elevation and two opposite partial sectional views in FIGS. 11A-11C. The control handle 38 includes an outer housing 140 formed by the juxtaposition of two molded housing halves 140a, 140b. The outer housing 140 includes a plurality of walls and/or bulkheads 141 that defined therebetween a series of internal housing cavities. A distal through bore formed in the outer housing receives the flexible shaft 36 leading to the distal jaws 40, 42. The aforementioned actuator 44, in the illustrated example, is journalled to pivot about a pin 142 fixed with respect to the housing, and includes a thumb pad 144 opposite the pin 142. A narrow section of the actuator 44 travels within a proximal-distal slot 146 in the housing 140 such that the thumb pad 144 provides a slider for the user. The actuator 44 is therefore constrained to pivot in a hollow space between the two housing halves 140a, 140b and the thumb pad 144 travels between opposite ends of the slot 146. Movement of the slider 144 in a distal direction (to the left in FIG. 11A) closes the jaws, while movement of the slider in the proximal direction (to the right in FIG. 11A) opens the jaws.

The exemplary control handle 38 includes circuitry for energizing the aforementioned heating elements at the distal end of the tool in addition to the mechanism for opening and closing the jaws. Although the invention is not limited to one particular switching arrangement, the exemplary embodiment includes a weld/cut switch that actuates both the welding heating element and the cutting heating element simultaneously, and coincident with the jaw closed position. Moreover, the control handle 38 includes a governor for limiting the force that can be applied by the jaws on tissue held therebetween.

Figure 11A:
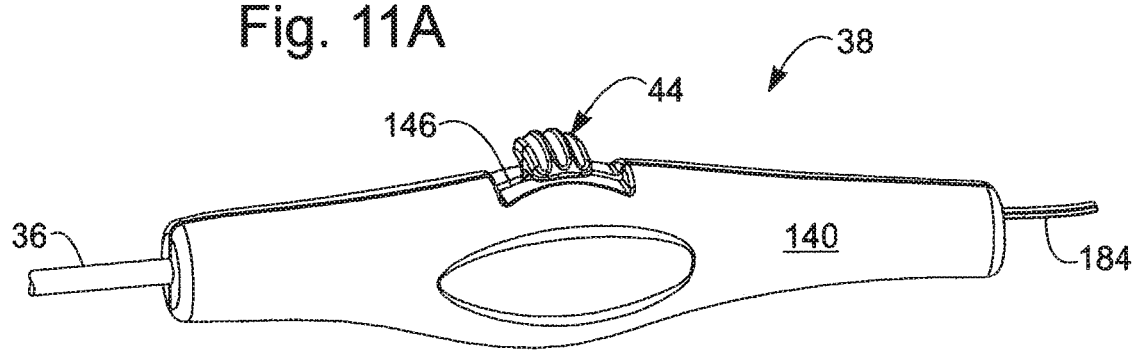
FIG. 11A is a perspective view of a proximal control handle of an exemplary tissue severing/welding device of the present invention.
Figure 11B:
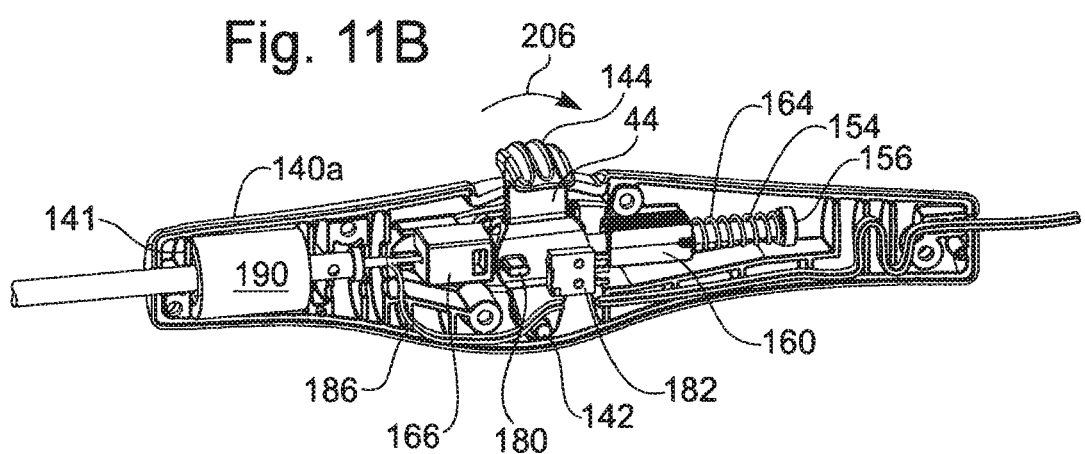
FIGS. 11B-11C are opposite longitudinal sectional views of the control handle of FIG. 11A including a passive smoke filter therein.
Figure 11C:
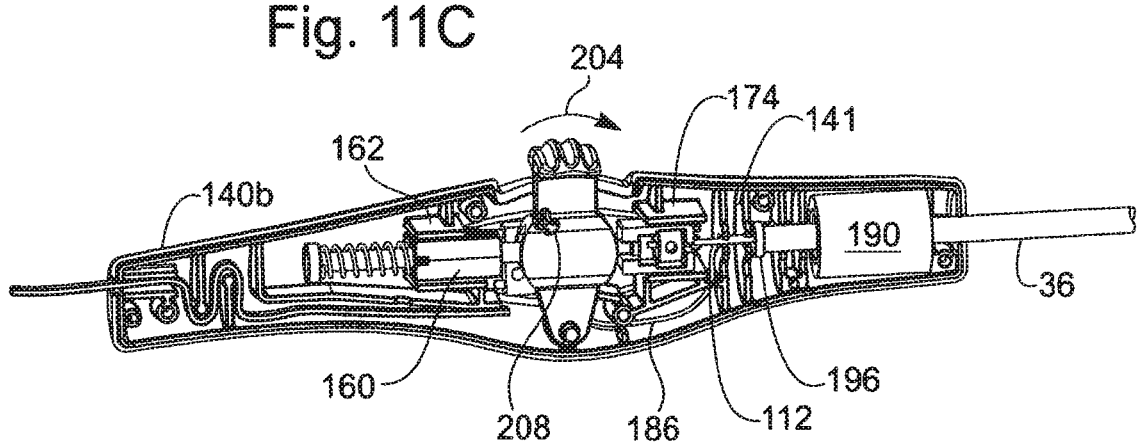
Figure 12:
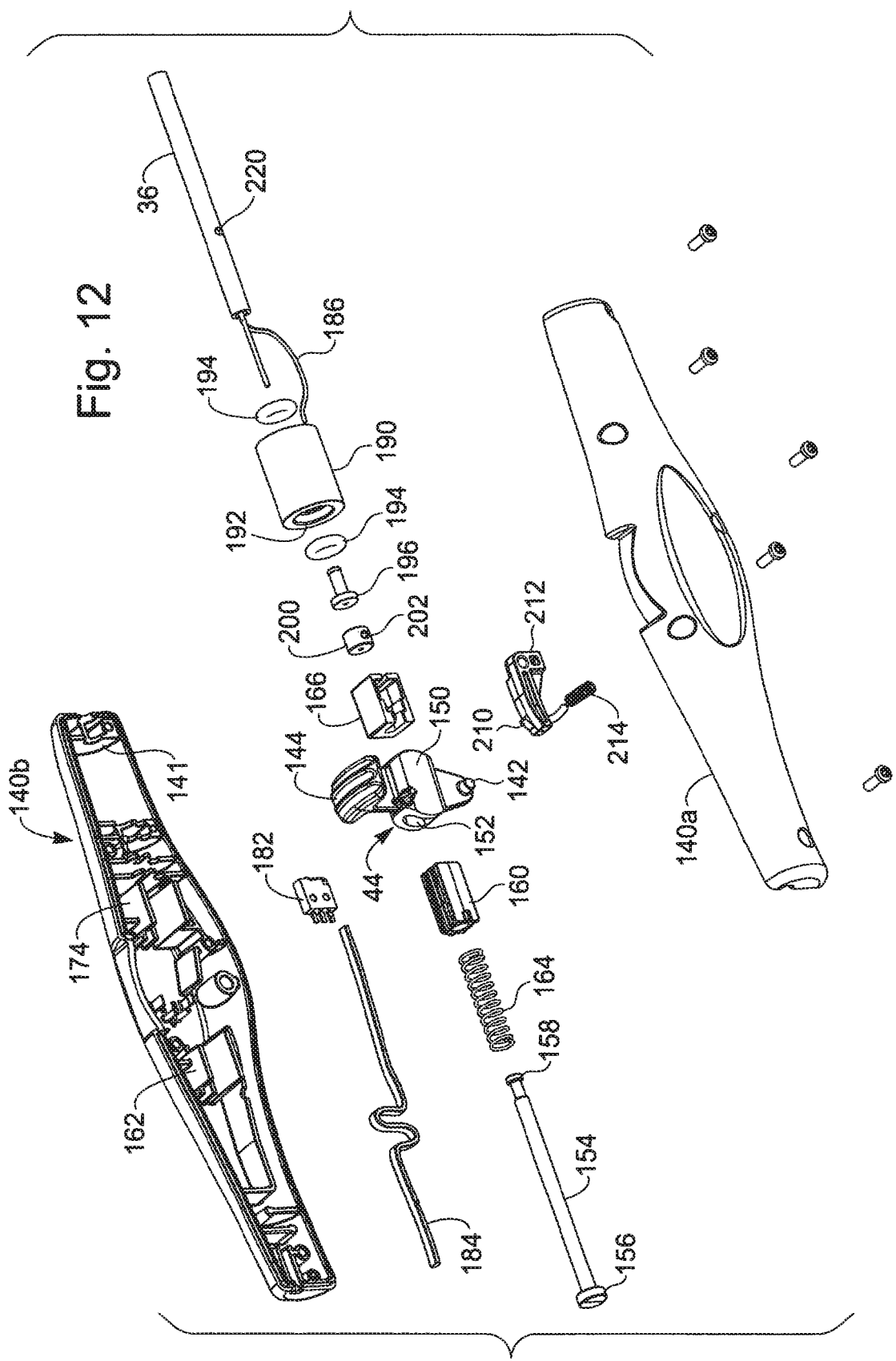
FIG. 12 is a perspective exploded view of the proximal control handle of FIG. 11A.

With reference still to FIGS. 11A-11C, and in particular the exploded view of FIG. 12, the actuator 44 possesses an enlarged mid-section 150 having a vertically elongated proximal-distal through bore 152 defined therewithin. The through bore 152 receives therein a rod 154 having a proximal head 156 and a distal head 158. The proximal end of the rod 154 extends through a force transfer block 160 and into a cavity to the proximal side of the actuator 44. The force transfer block 160 translates in a proximal-distal direction between a pair of guide walls 162 formed in the housing and includes a bore that slides over the rod 154. A force-limiting spring 164 closely surrounds the rod and is constrained between the proximal head 156 and the force transfer block 160. The distal end of the rod 154 extends to the distal side of the actuator 44 such that the distal head 158 is captured within a force coupler 166. FIG. 12 illustrates best the internal contours of the generally box-shaped force coupler 166 which includes a large cavity, a smaller cavity in which the distal head 158 is received, and a pair of slots on opposite ends thereof (elements not numbered for clarity). One side of the force coupler 166 is removed to facilitate assembly of the cooperating parts, as seen in FIG. 11C. Like the force transfer block 160, the force coupler 166 translates in a proximal-distal direction between a pair of guide walls 174 formed in the housing.

With specific reference to FIG. 11B, a small tang 180 projects laterally from the enlarged mid-section 150 of the actuator 44. The tang 180 is positioned to engage and trip a weld/cut switch 182 mounted within the housing 140. That is, the switch 182 is fixed with the respect to the housing 140, while the tang 180 pivots with the actuator 44. When the thumb pad 144 translates in a proximal direction within the slot 146, the actuator 44 pivots in a clockwise direction until the tang 180 actuates the lever of the weld/cut switch 182. An electrical wire 184 extends into the proximal end of the handle 38 and provides power to the switch 182. From there, an electrical lead 186 continues in the distal direction and passes through the flexible shaft 36 to the heating elements on the jaws at the distal end of the tool.

FIGS. 11B and 11C illustrate a cylindrical filter 190 captured between bulkheads 141 at the distal end of the housing 140. The generally tubular filter 190 is seen exploded in FIG. 12, and includes a stepped through bore 192 that receives, on either end, a pair of O-rings 194. The O-rings 194 each have an inner diameter that closely fits and seals around the flexible shaft 36. The shaft 36 extends into the distal end of the housing 140, through the filter 190, and terminates at a seal 196 adjacent one of the bulkheads 141 of the housing. As shown in FIG. 11C, the control rod 112 continues through the seal 196 and into the force coupler 166. A collar 200 received in the large cavity of the force coupler 166 fastens to the proximal end of the control rod 112 with a set screw 202. In this manner, the proximal end of the control rod 112 is constrained by the collar 200 within the force coupler 166.

In use, the operator slides the thumb pad 144 in a distal direction along the slot 146 as seen by arrow 204 in FIG. 11C to pivot the actuator 44 and open the jaws of the tool. As the actuator 44 pivots, its angular movement is accommodated by the elongated through bore 152 over the rod 154. A curved distal face of the enlarged mid-section 150 eventually contacts the proximal end of the force coupler 166 and acts as a cam to urge it in a distal direction. Because the collar 200 is constrained within the larger cavity of the force coupler 166, it also translates in a distal direction which, in turn, pushes the control rod 112 distally. In this embodiment, there is no clutch or force-limiter interposed between the actuator 44 and distal movement of the control rod 112 to open the jaws. Therefore, the extent that the jaws open is limited by the extent of travel of the thumb pad 144, or by the hinge mechanism of the jaws themselves.

Conversely, the operator slides the thumb pad 144 in a proximal direction along the slot 146 as seen by arrow 206 in FIG. 11B to pivot the actuator 44 and close the jaws of the tool. A curved proximal face of the enlarged mid-section 150 eventually contacts the distal end of the force transfer block 160 and acts as a cam to urge it in a proximal direction. Because the force transfer block 160 is free to slide over the rod 154, it moves in a proximal direction toward and compresses the spring 164. Compression of the force-limiting spring 164 applies a proximally-directed force to the proximal head 156 of the rod 154. Because the distal head 158 is constrained within the stepped cavity of the force coupler 166, which in turn is connected to the control rod 112, the resistance to proximal displacement of the rod 154 is provided by any force resisting closure of the jaws (assuming minimal frictional forces acting on the control rod 112). Prior to the jaws clamping any tissue, this resistance to proximal displacement of the rod 154 is minimal and proximal displacement of the force transfer block 160 translates into equivalent displacement of the control rod 112. However, when the jaws finally close on tissue, the maximum closing force of the jaws is limited by the stiffness of the spring 164. Specifically, after the jaws close a constant force is applied to the tissue therebetween because of the spring 164.

Through careful calibration of the force-limiting spring 164 in conjunction with the particular jaws on the tool, this closing force can be limited to less than that which would unduly crush or otherwise cause trauma to the tissue within the jaws. Those of skill in the art will understand that it is the pressure applied to the tissue that must be limited, and that the pressure partly depends on the shape and size of the jaws, as well as the elastic constant of the spring 164. Desirably, the force imparted on tissue by the jaws is between about 1-3 lbs (0.45-1.36 kg), and preferably about 1 lb, as regulated by the spring 164. This preferred range of force ensures the heating elements effectively weld and sever tissue held within the facing surfaces of the jaws in a reasonably short amount time, preferably within 5 seconds or less. That is, applying a force of less than 1 lb to tissue tends to delay the cutting function, while application of a force greater than 3 lbs tends to sever the tissue before an effective weld is formed. Again, this preferred force range and operation time to depend upon the size and shape of the jaws. However, given the constraints of endoscopic tissue welding, in particular during vessel harvesting procedures, these parameters are believed to encompass a wide range of suitable jaw types.

To better explained the desirable weld parameters of the tissue welder, the reader is directed back to FIGS. 8A-8H showing the inner jaw member 62 of the hot jaw, and FIGS. 10A-10H showing the boot 52a that covers the inner jaw member 62. The inner jaw member 62 has the curved distal portion 64 extending from the proximal pivot housing 66, and a length from the circular pivot hole 67 to its distal tip of approximately 0.740 inches (18.80 mm) As mentioned above, the inner jaw member 102 of the cold jaw 42 is slightly longer than the more blunt inner jaw member 62 of the first jaw 40 to ease dissection of tissue, and preferably has a length of approximately 0.765 inches (19.43 mm). Desirably, the jaw member 62 is made of stainless steel, although other materials, thermally conductive or otherwise, may be utilized. The transverse cross-sectional shape of the distal portion 64 is approximately square adjacent the pivot housing 66, having a dimension on each side of approximately 0.060 inches (1.52 mm). The dimension of the tissue-facing side of the distal portion 64, seen in FIG. 8E, remains constant along the length of the jaw member 62, while the perpendicular dimension seen in FIGS. 8D and 8F gradually tapers smaller toward the distal tip to a final dimension of about 0.031 inches (0.79 mm). The boot 52a seen in FIGS. 10A-10H has an overall length sufficient to cover the curved distal portion 64, and a transverse tissue-facing width of approximately 0.082 inches (2.083 mm). The dimensional parameters of the boot 52b of the cold jaw are equivalent, although the two boots perform different functions and are thus configured differently.

The previously mentioned desirable clamping force of the jaws of between 1-3 pounds can also be characterized in terms of pressure on the tissue to produce the most effective balance between severing and welding. Using the approximate dimensional values given above, the jaws desirably exert a pressure on the tissue of between about 25-75 psi, averaged transversely across the tissue-facing surfaces of the boots 52a, 52b. It should be understood that this range is an estimate based on the non-uniform contours of the tissue-facing surfaces of the boots 52a, 52b, and those of skill in the art will understand that structural modifications to the jaws may affect the preferred force and/or pressure range. Moreover, the temperature to which the heating elements on the jaws rise also affects the preferred force applied, as well as the duration of the weld. Once again, a commonly accepted range of temperatures at which human tissue may be welded is 50 to 90° C., while severing occurs at temperatures of 100° C. and above. Using these guidelines, if the exemplary jaws apply a clamping force of between 1-3 pounds on tissue and the welding and severing heating elements are energized to these temperatures, a preferred duration of weld is between 1-5 seconds. If the clamp duration is too short, the weld may not be effective and the tissue is less likely to completely sever, while an excessive duration above 5 seconds may tend to char tissue.

Still with reference to FIG. 11B, movement of the actuator 44 in the direction of arrow 206 also displaces the tang 180 into engagement with the weld/cut switch 182. Even if the intervening force-limiting spring 164 limits further closure of the jaws, the actuator 44 can continue movement until the switch 182 is tripped. The control handle 38 of the present invention further includes feedback to indicate to the user aurally and via tactile sensation through the thumb pad 144 when the switch 182 has been tripped, both on and off. More particular, FIGS. 11C and 12 illustrate a small protrusion 208 projecting laterally from the actuator 44. This protrusion pivots along with the actuator and engages a small tooth 210 provided on a pivoting detent lever 212 (see FIG. 12). Although not shown in FIG. 11C, the detent 212 pivots about a point fixed within the housing 140 and the tooth 210 is biased upward by a detent spring 214. The protrusion 208 cams past the tooth 210 which displaces and provides both an audible and tactile click to the user at the point that the switch 182 is tripped ON. Movement of the actuator 44 in the opposite direction also causes the protrusion 208 to cam past the tooth 210, thus indicating when the switch 182 is turned OFF. In an exemplary procedure, the weld time is typically less than 5 seconds.

The exemplary control handle 38 illustrated in FIGS. 11A-11C and FIG. 12 further includes a system for capturing smoke or particulate matter that is generated by the distal jaws at the operating site within the tissue cavity. As mentioned above, various end effectors may be utilized with certain aspects of the present invention, with resistance heating elements being featured as the exemplary embodiment. Most of these end effectors, including resistance heating elements, often cause a substantial amount of smoke to be generated from the heated tissue. Often, the operation is performed using $CO_2$ insufflation which creates a pressure gradient forcing gas in a proximal direction through the flexible shaft 36.

To control egress of this smoke through the flexible shaft 36, the control handle 38 provides the aforementioned passive filter 190. The flexible shaft 36 includes at least one gas escape port 220 at its proximal end. This port 220 is positioned between the O-rings 194 and within the hollow interior of the filter 190. The hollow cavity within the filter 190 provides a venting chamber or space to receive the gasses from the port 220. In addition, the proximal end of the flexible shaft 36 is capped by the seal 196 which conforms closely around the control rod 112 and electrical lead 186. All of these seals force any gas (and smoke or particulate matter) traveling proximally through the flexible shaft 36 to exit through the gas escape port 220. Consequently, the gas is forced through the gas permeable material of the filter 190 which traps any smoke or particulate matter before it reaches the interior of the housing 140. From there, the now filtered gas, predominantly $CO_2$, passes through the various cavities within the housing 140 and exits through random fissures and openings therein.

Figure 11D:
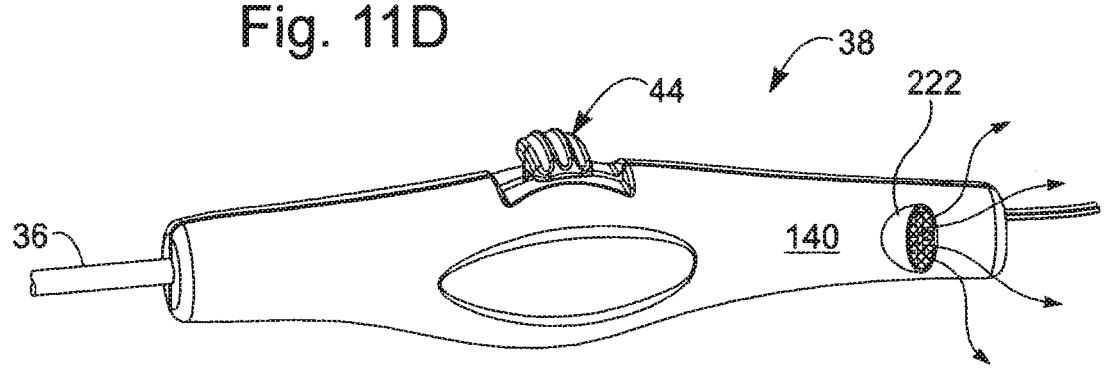
FIGS. 11D-11F illustrate control handles having alternative smoke filter configurations.
Figure 11E:
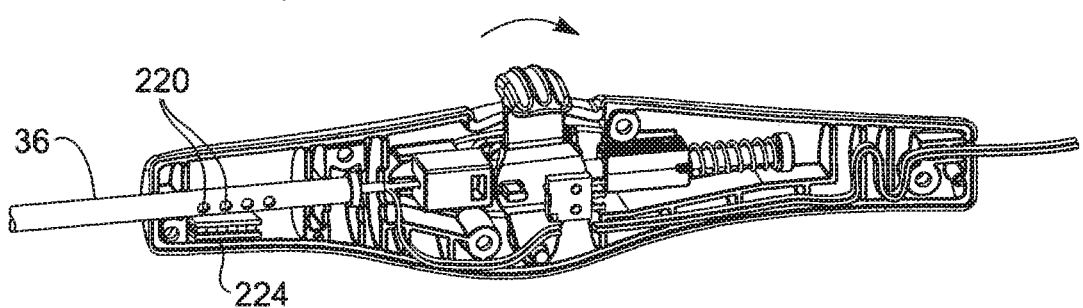
Figure 11F:
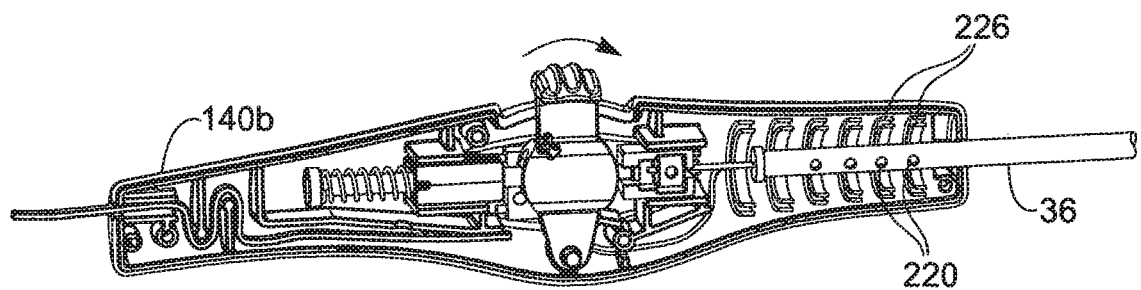

Several alternative configurations for filtering smoke generated by the tissue welding procedure are seen in FIGS. 11D-11F. First of all, FIG. 11D illustrates the exemplary control handle 38 having a small exhaust fan 222 mounted near its proximal end. The exhaust fan 222 helps pull gas passing through the elongated shaft 36 through the aforementioned passive filter 190. In many instances means for gas insufflation is provided in the overall system within which the tissue welders is used, which provides a positive pressure within the body cavity and forces gas proximally through the elongated shaft 36. However, in some procedures either no insufflation is used or it does not generate sufficient pressure, in which case the auxiliary fan 222 helps pull the gas through the filter 190.

FIG. 11E illustrates the interior of an alternative control handle in which a cooling apparatus 224, such as a Peltier cooler, is mounted adjacent the gas escape ports 220 in the elongated shaft 36. The smoke emitted from the port 220 connect is on the cooling apparatus 224, which effectively passively filters the gas which is then permitted to exit from various openings in the handle.

Alternatively, FIG. 11F illustrates a further alternative control handle in which a plurality of louvers or fins 226 are arranged adjacent the gas escape ports 220. The fins 226 diffuse and condense the smoke traveling proximally through the elongated shaft 36, and thus act as a passive filter. The gas is then permitted to exit from various openings in the handle. Because the surface area through which the smoke exhausts is expanded, the density of that smoke is decreased making it less noticeable as it exits the handle. In the illustrated embodiment, the fins 226 are configured as a series of concentric annular elements, but other arrangements are possible.

Figure 13A:
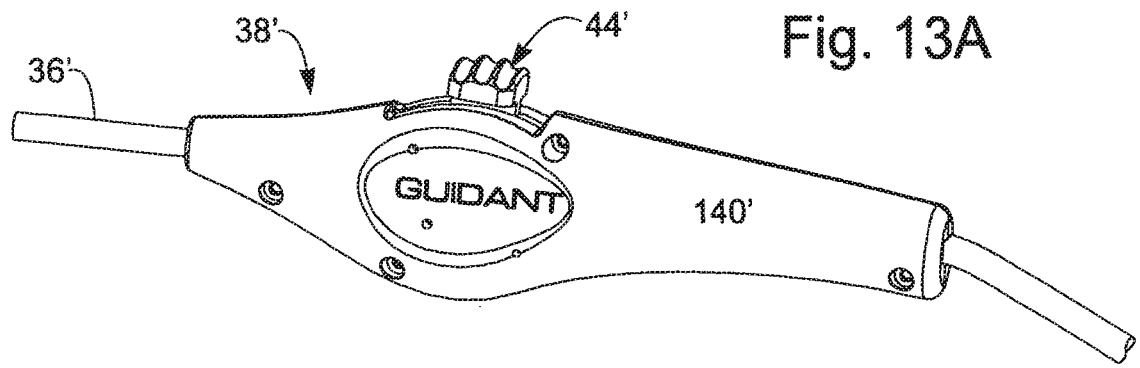
FIG. 13A is a perspective view of an alternative control handle of the present invention.
Figure 13B:
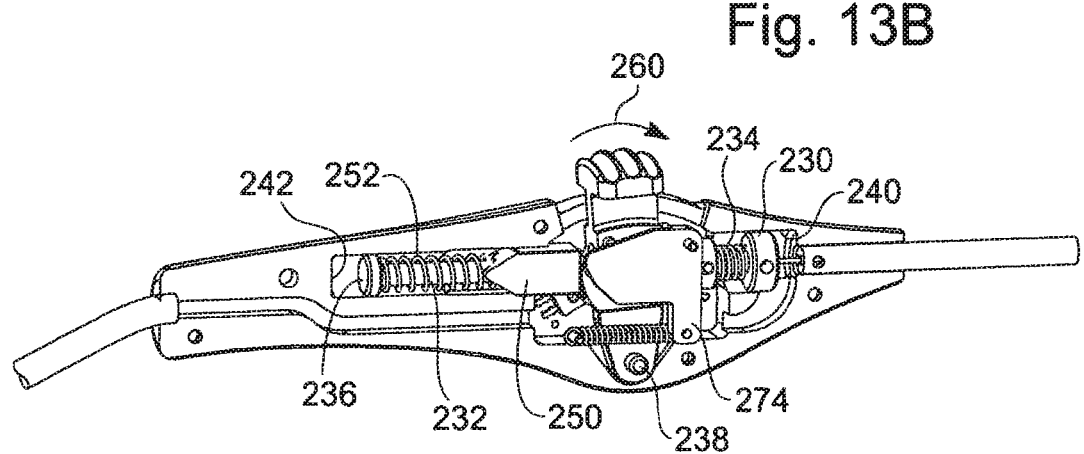
FIGS. 13B-13C are opposite longitudinal sectional views of the control handle of FIG. 13A.
Figure 13C:
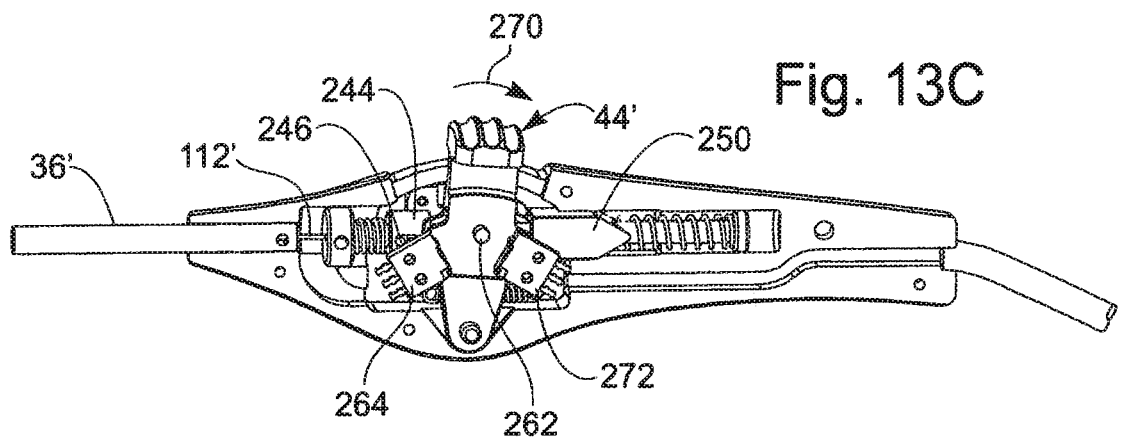

FIGS. 13A-13C illustrate an alternative control handle 38' similar to that described above but including a separate electrical circuit for a fasciotomy cutter provided on a distal tool. As mentioned above, fasciotomy comprises an incision through fascia (e.g., bands or fillets of fibrous tissue that separate different layers of tissue). The tissue welding/ cutting jaws may also be adapted to include such a fasciotomy cutter which enables the tool to be moved linearly through to cut tissue without opening and closing the jaws. The fasciotomy cutter may be a separate heating element provided on the forward end of one of the jaws, or within the jaws. Some of the elements illustrated for the alternative control handle 38' are common to the control handle 30 described above with respect to FIGS. 11-12, and therefore will be given the same element number with a prime "'" designation.

As seen in FIGS. 13B-13C, the flexible shaft 36' from the distal tool enters the molded housing 140', and a control rod 112' projects therefrom into a cavity formed within the housing and is fixed to an enlarged collar 230. Although not shown, a shaft member 232 fastened to the collar 230 extends in a proximal direction through a fasciotomy spring 234, and through an actuator 44' to terminate at a proximal head 236. The actuator 44' is much like the actuator 44 described above, with a body that pivots about a pin 238 and has an elongated through bore for passage of the shaft 232. The distal end of the shaft 232 having the collar 230 thereon translates within a proximal-distal cavity 240, while the proximal end of the shaft having a proximal head 236 translates within a proximal-distal cavity 242. Because the control rod 112' is rigidly fastened to the collar 230 which in turn is fastened to the shaft 232, movement of the shaft produces identical movement of the control rod.

With particular reference to FIG. 13C, an annular cam follower 244 surrounds the shaft 232 between the actuator 44' and the fasciotomy spring 234. The cam follower 244 includes a short slot (not numbered) within which extends a small pin 246 projecting laterally from the shaft 232. In the position illustrated, the actuator 44' is in a neutral position not in contact with the cam follower 244, which in turn is therefore biased in a proximal direction by the fasciotomy spring 234 as far as the pin 246 and slot permit. A second cam follower 250 surrounds the shaft 232 between the actuator 44' and the fasciotomy spring 234. A force-limiting spring 252 is concentrically constrained around the shaft 232 between the proximal head 236 and the second cam follower 250. As noted, the actuator 44' is in the neutral position out of contact with the second cam follower 250, and thus the force-limiting spring 252 remains uncompressed.

A user displaces the thumb pad of the actuator 44' in a proximal direction as indicated by arrow 260 in FIG. 13B, which pivots the actuator 44' and urges the cam follower 244 in a proximal direction. Compression of the fasciotomy spring 234 causes proportional displacement of the collar 230 and control rod 112', therefore opening the jaws of the tool. At a certain distance of travel, the collar 230 reaches the end of the cavity 240 and further movement of the control rod 112' is impeded, corresponding to the maximum opening distance of the jaws. However, because the cam follower 244 includes the linear slot in which the pin 246 travels, the actuator 44' can continue its movement forcing the cam follower 244 proximally against the compressive force of the spring 234. The user experiences a resistance to movement of the actuator 44' during this stage, which is an indication that the fasciotomy heater is activated. In particular, a tang 262 (FIG. 13C) on the actuator 44' eventually engages a fasciotomy switch 264 at the point that the fasciotomy spring 234 is being compressed. Although the circuitry is not shown, the switch 264 is supplied with current and when switched ON provides current to leads extending through the flexible shaft 36' to the distal end of tool and fasciotomy heating element.

Conversely, the user displaces the actuator 44' in a proximal direction as indicated by arrow 270 in FIG. 13C to close the jaws. A proximal face of the actuator 44' cams against the follower 250, which in turn acts against the force-limiting spring 252. As in the earlier embodiment, a minimal reaction force exists prior to the jaws closing and thus movement of the actuator 44' causes proportional movement of the control rod 112'. At the point that the jaws close over tissue, the force-limiting spring 252 determines the amount of pressure that may be applied to the tissue before further movement of the actuator 44' merely compresses the spring without moving the control rod 112'. Near the limit of travel of the actuator 44' in the direction of arrow 270, the tang 262 engages a weld/cut switch 272 mounted within the housing 140', thus actuating the welding and cutting heating elements at the distal end of the tool. The alternative control handle 38' further includes a detent 274 that acts in the same manner as the detent 212 described above and indicates to the user when the weld/cut function is ON and OFF.

Figure 14A:
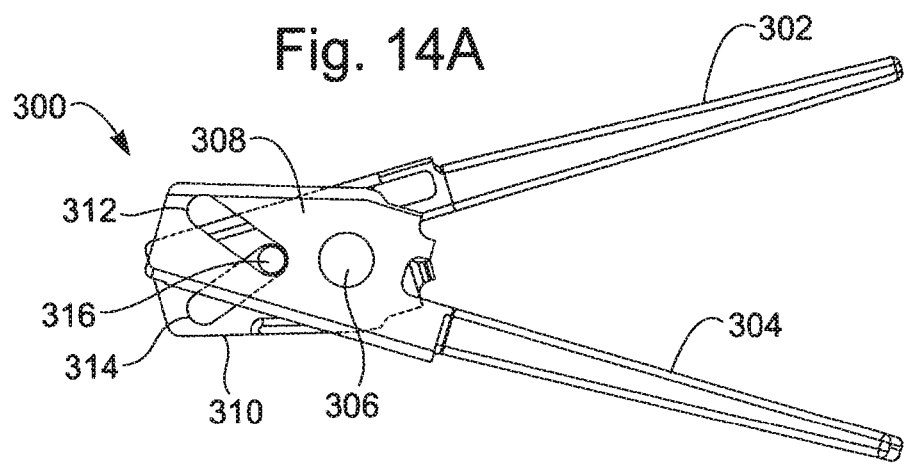
FIGS. 14A-14C are elevational views of pair of jaws in open and closed positions that illustrate a preferred jaw opening mechanism of the present invention.
Figure 14B:
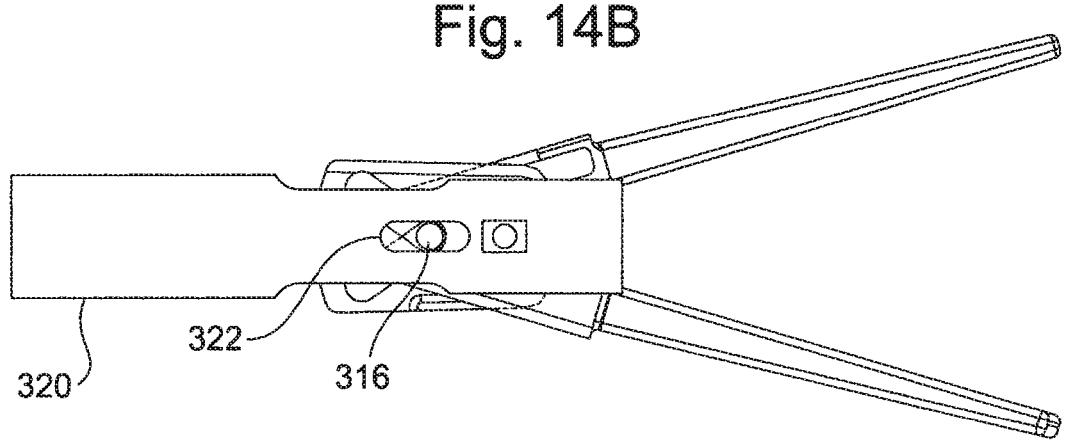
Figure 14C:
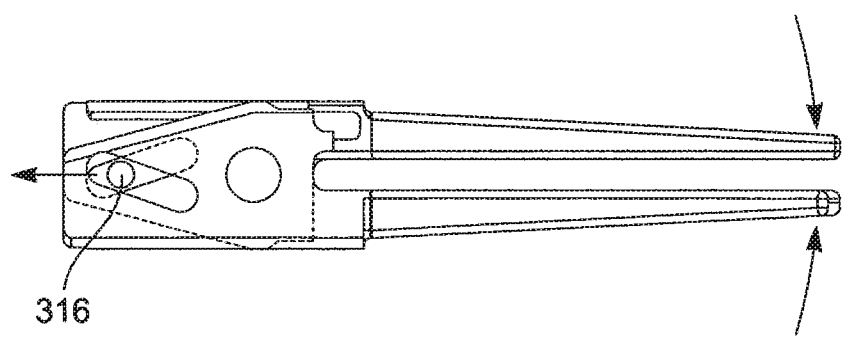

FIGS. 14A-14C illustrate a preferred linkage 300 between a control rod and the jaws for opening and closing the jaws. In the jaw opening mechanisms of the prior art, certain disadvantages were recognized that increase the overall size of the jaw assembly, increase the cost of construction, exposed electrical connections to wear, or sacrificed mechanical and electrical consistency by including excess sources of friction, and sacrificed electrical consistency by relying on moving mechanical connections for electrical continuity, for example. The exemplary linkage 300 and the associated "hard-wired" electrical connection reduces the overall size of the jaws assembly, reduces the number of components and associated cost and complexity, improves the robustness of the mechanics, and improves the mechanical and electrical reliability (i.e., consistency) of the device.

A pair of jaws 302, 304 are shown open in FIGS. 14A and 14B. Each jaw includes a through bore that is journalled about a shaft 306, such as the shaft stub 98 as seen in FIG. 5B. In this manner, proximal housings 308, 310 of the respective jaws pivot with respect to one another. An angled slot 312, 314 is provided in each pivot housings 308, 310. An actuating pin 316 extends into both of the angled slot 312, 314 and is connected to a proximal control rod (not shown). FIG. 14B illustrates the distal end of a tool shaft 320 that encompasses the pivot housings 308, 310. The tool shaft 320 includes a linear slot 322 within which the actuating pin 316 translates. The distal end of the tool shaft 320 shown is analogous to the shaft tip 54 seen in FIGS. 2 and 4.

FIG. 14C shows movement of the actuating pin 316 to the left which causes the jaws 302, 304 to close. That is, the pin 316 cams the angled slots 312, 314 such that their proximal ends come together as seen. Of course, the reverse movement of the actuating pin 316 causes the jaws to open again. Because of the simplicity of the mechanism, the overall size of the jaw assembly can be reduced so that it fits through a 5 mm inside diameter tube. Furthermore, the reduction in the number of parts obtains an equivalent reduced manufacturing time and complexity, for a lower manufacturing cost. The moving parts consist of the actuating pin 316 translating within the three slots, and the two jaws which pivot with respect one another. This reduces the sources of friction and thus improves mechanical reliability. Finally, the angle of the slots 312, 314 may be adjusted to change the actuation force required to open and close the jaws. That is, a shallower angle would necessitate a lower force from the control rod to actuate the jaws. The trade-off, of course is that the opening distance of the jaws is concurrently reduced.

Clearly, the dual- or tri-heating element function can be achieved in many different ways. The present invention broadly includes a heating element for cutting tissue and a heating element for welding tissue, and is not particularly limited to any one type of either apparatus. Examples include, but are not limited to two, three, or more heating elements, cutting and welding heating elements separately activated or connected in series or parallel, or both, heating elements on one or both jaws, etc. The form of the multiple heating elements is preferably chosen so that they are relatively close together and one reliably cuts and the other reliably welds a variety of tissue. Optionally, the multiple heating elements are configured such that they operate substantially simultaneously and ensure good hemostasis of the welded tissue. The power applied and shape of the heating elements are chosen to ensure that inadvertent tissue charring or other such damage does not occur inadvertently during normal operation of the device. The primary clinical benefits of the heating elements of the present invention include but are not limited to balance of power outputs from cutter and welder(s) for consistently strong welds, as well as thermal efficiency for faster weld times.

It should be understood that the force-limiting function of the spring within the control handle can be achieved in many different ways. The present invention, in its broad interpretation, is not particularly limited to any one type of mechanism for limiting the closing force of the jaws, but is characterized by a force-limiting interface between the control actuator and the elongated jaws for limiting the magnitude of closing force of the jaws. Examples include, but are not limited to the aforementioned spring provided within the control handle, a similar spring provided distal to the control handle, a pressure transducer on the jaws which provides feedback to the user or other device for limiting the force applied by the jaws, compliant jaws, etc. The form of the force-limiting apparatus is preferably chosen to limit the pressure applied to tissue by the particular jaws. Optionally, the force-limiting apparatus is configured simply in a cost-effective manner. The force-limiting apparatus is chosen to ensure that crushing of tissue does not occur inadvertently during normal operation of the device.

While the tissue welding system described thus far is believed to be particularly effective, the present invention also provides a number of alternative jaw and heating elements which are each believed to be patentable in its own right. A number of these alternatives will now be described briefly with reference to FIGS. 15-37. It should be understood by the reader that generally, any of these jaw or heating element configurations can be coupled with any of the aforementioned control handle/shaft embodiments. For example, if a particular jaw includes a fasciotomy cutter in addition to a tissue cutter and a tissue welder, it may be used with the control handle 38' of FIGS. 13A-13C, but also aspects of the control handle 38 of FIGS. 11-12 may be substituted.

Prior to a discussion of the multiple alternative embodiments, it is important to understand the basic structure of the exemplary embodiment described above. FIG. 15 illustrates in cross-section a first jaw 330 spaced from a second jaw 332. Both jaws include an inner jaw 334 surrounded by a boot 336. As will be understood shortly, the materials of the inner jaws 334 and boots 336 may be specifically designed to control the heat concentration/dissipation within the jaws 330, 332. In the exemplary embodiment, however, the inner jaws 334 are made of stainless steel while the boots 336 are silicone. The lower jaw 330 is the "hot" jaw, and includes multiple heating elements outside the boot 336. Specifically, a first heating element 338 extends along the inner or jaw-facing surface 339 of the first jaw 330, and comprises at least two welding members, one each on either side of a centrally disposed second heating element 340. Both the first and second heating element 338, 340 are positioned outside the boot 336, which is shown having a planar jaw-facing surface 339 and a rounded outer surface (not numbered). The first heating element 338 is supplied with power and acts as a welding heater, while the second heating element 340 reaches a higher temperature and, also because of its smaller cross-section, acts as a cutting heater. As described above, in some embodiments, the welding members of the first heating element 338 are connected electrically in series with the single second heating element 340, but in parallel with each other. The lower current through the parallel welding members results in less heat generation and lower tissue temperatures than the cutting heater, facilitating tissue welding.

FIGS. 16A-16B show a slight variation on a first jaw 330' wherein the outer boot 336' defines a centrally located and longitudinally directed channel or depression 342 within which the second heating element 340' resides. A comparison of the cross-sections of FIGS. 15 and 16B shows that the second heating element 340' is somewhat larger in diameter than the earlier heating element 340, which size difference is accommodated by the depression 342. In this way, various configurations of cutting heaters may be utilized without unduly increasing the elevation relative to the first heating elements 338.

FIG. 17 illustrates another possible variation on the hot jaw 330" in which only one heating element 344 is provided. Instead of a second heating element, the first heating element 344 is placed on a conductive plate 346, preferably within a centrally located channel or depression 348. Although not shown, the conductive plate 346 is desirably electrically insulated from the heating element 344. When the heating element 344 is activated, it generates sufficient heat to cut through tissue while the conductive plate 346 absorbs some of the heat to function as tissue welding surfaces. The conductive plate 346 may be made of copper, aluminum, or ceramics high in thermal conductivity, such as Alumina. An insulating layer between the heater 344 and depression 348 may be provided by a layer of ceramic, Teflon, polyimide, or other such material capable of withstanding high temperatures. With the passively heated weld plate 346, this design only requires a single electrical circuit looped through the heating element 344.

The use of a heat sink on both sides of the tissue welder in jaws to limit thermal spreading is also contemplated by the present invention. A heat sinking wire or jaw insert may be provided on both sides of the hot wire, such as in the position of the heating elements 338 in FIG. 15. Alternatively, the heat sink may be provided on the jaw opposite the hot wire. In either situation, heat flux transfer lines will travel from the hot wire to the heat sink, thus limiting thermal spread and volume of tissue heated. To further enhance this focused heating, thermal insulation may be provided on the outboard faces of the heat sinks or jaws to retain the applied heat inside the jaws.

In each of the designs shown in FIGS. 15-17, the temperature profile achieved is a high temperature along the jaw midline for cutting, with a lower temperature on both sides for welding without cutting. This results in the formation of a wider, more consistent weld band than with a single heater over the midline of the boot, as present in prior art devices. In particular, when used to cut and weld vessels, the resulting wider weld band is stronger and more consistently prevents subsequent leaks.

Now with reference to FIGS. 18A-18C, an alternative jaw configuration is shown that again includes multiple heating elements, but instead of all being on one of the jaws they are distributed on both jaws. More particularly, a first jaw 350 possesses a first heating element 352 in the shape of a relatively wide plate on the jaw-facing surface of the boot. A second jaw 354 includes a second heating element 356 comprising a relatively narrow wire, again placed on the jaw-facing surface of the boot. The second heating element 356 is desirably positioned at the approximate lateral midline of the second jaw 354. Because the heating elements 352, 356 are on different jaws, they may conveniently be supplied with power through separate circuits. Through choice of materials, current supplied, and size difference between the two heating elements, the first heating element 352 welds tissue while the second heating element 356 reaches a higher temperature and cuts tissue. FIGS. 18B and 18C schematically illustrates the temperature profiles of the jaw-facing surfaces of the two jaws 350, 354 when the respective heating elements are activated.

Because the heating elements 352, 356 of FIG. 18A may be energized through separate circuits, they may be activated at different times. One embodiment of the present invention is a two-stage heating process in which current runs through the first heating element 352 to form a weld band in the tissue or vessel. Subsequently, current passes through the second heating element 356 to generate a localized hot zone and cut the tissue or vessel in the middle of the weld band. As mentioned above, the total weld time is desirably less than 5 seconds, and therefore one method contemplated is to energize the first heating element 352 for between 3-5 seconds, switch the first heating element off, energize the second heating element 356 until the tissue or vessel severs, and then switch the second heating element off.

Certain designs of tissue welder jaws of the prior art included a stainless steel inner jaw covered with a silicone boot or jacket. A heating element outside of the silicone boot was directly attached to the stainless steel inner jaw on its underside (i.e., on the side facing away from the other jaw), and the inner jaw therefore served as a return path for the electrical current through the heating element. However, with this configuration the stainless steel inner jaw retains a significant amount of heat energy during the thermal welding process, thereby adversely affecting the consistency and efficiency of the thermal tissue-welding system. Furthermore, the electrical contact between the heating element and stainless steel created a direct heat conduction flow path. To address this thermal inefficiency, the present invention contemplates limiting the amount of heat energy that is transferred to the inner jaws either at the attachment of the heating element to the jaw and/or along the length of the heating element, and also by material choice.

For example, the inner jaws may be fabricated of a thermally-insulating material having significantly lower thermal conductivity than stainless steel (17.9 Watts per meter-Kelvin: W/m-K). More specifically, the inner jaws are desirably fabricated of a material having a thermal conductivity of less than about 5.0 W/m-K. A number of ceramics having the desirable low thermal conductivity are suitable, including alumina, machinable glass ceramic (e.g., MACOR), zirconia, yttria, and partially stabilized zirconia (e.g., YTZP). MACOR has a thermal conductivity of about 1.6 W/m-K, zirconia is 1.675 W/m-K, and YTZP is 2.2 W/m-K. The inner jaws may be formed completely of one of these low thermal conductivity materials, or a conventional stainless steel inner jaw may be completely or partly coated with the material, which impedes conductive thermal transfer to the stainless steel. The material may be fabricated by machining (e.g., MACOR) or ceramic injection molding (e.g., zirconium and YTZP). In addition, the electric circuit for the heating element may be formed as conductive traces on the ceramic material, as opposed to using the inner jaw as the return current path, even if an inner jaw is still used. Through the use of these traces 366, 370, and by choosing a relatively electrically insulating inner jaw 362, current does not pass through the inner jaw.

For example, FIGS. 19A-19E illustrate an exemplary jaw 360 including an inner jaw 362 of a low thermal conductivity material (<5.0 W/m-K) having a sloped distal end. A heating element 364 is seen on an inside face of the inner jaw extending longitudinally along a main portion and then sloping downward along with the inner jaw. The heating element 364 forms a part of the circuit completed by a number of copper traces extending along the inner jaw 362. More specifically, a first trace 366 extends along one lateral side of the jaw 360 and connects with the heating element 364 near the distal tip thereof, as seen at 368. The return current from the proximal end of the heating element 364 passes through a second trace 370 that is connected to a ring-shaped conductor 372 that may be used to surround a pivot shaft. Although not shown, electrical wires along a flexible delivery shaft of the tissue welder complete the circuit.

Figure 19A:
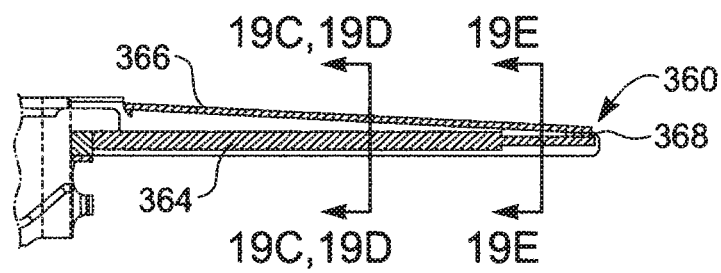
FIGS. 19A-19E illustrate an exemplary jaw including an inner jaw of a low thermal conductivity material.
Figure 19B:
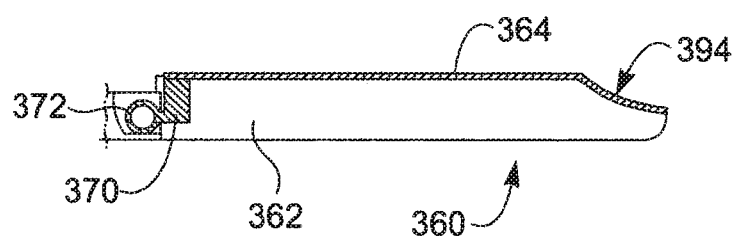
Figure 19C:
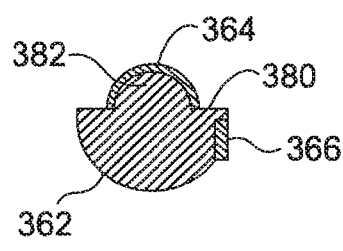
Figure 19D:
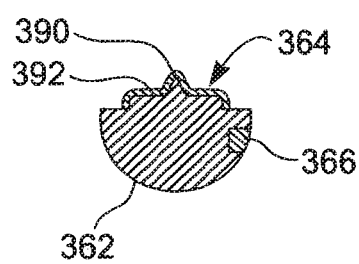

FIGS. 19C and 19D illustrate two alternative cross-sections for a midportion of the jaw 360. In FIG. 19C, the inner jaw 362 is generally semi-cylindrical in shape with a flat clamping surface 380 interrupted by a centrally located semi-cylindrical rail 382. The relatively thin heating element 364 conforms in a semi-tubular shape around the rail 382. In this configuration, the apex of the heating element 364 imparts the greatest pressure to tissue clamped between the jaw 360 and the opposing jaw (not shown), and thus performs the cutting function. The lateral portions of the heating element 364 to both sides of the apex are in relatively lesser degrees of contact/pressure with the tissue, but are still heated, and effectively weld the tissue on both sides of the cut line. FIG. 19D illustrates an alternative shape for the heating element 364 which exhibits both an upstanding narrow central rail 390 and a pair of relatively flat shoulders 392 adjacent the rail. The upstanding rail 390 performs the cutting action, while the flat shoulders 392 weld the adjacent tissue.

Figure 19E:
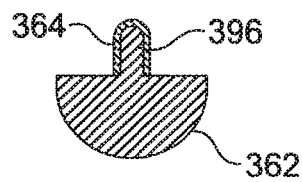

The jaw 360 of FIGS. 19A-19E further includes a distal fasciotomy section 394 at the point at which the inner jaw 362 slopes. FIG. 19A depicts a narrowing of the heating element 364 in this section, and FIG. 19E shows the cross-section of the inner jaw 362 which includes a relatively pronounced rib 396 around which the heating element conforms. Because of this pronounced shape of the heating element 364 in the sloped section 394, forward movement of the jaws through tissue with the element 364 activated easily performs a cutting action. The jaws can be open or closed. In this embodiment, the fasciotomy heater is merely an extension of the joint cutting and welding heater, and all of these portions of the heating element 364 are energized simultaneously. As was explained above, however, a separate fasciotomy cutter having the shape and position as shown may also be provided so that it can be turned off when the tissue severing and welding operation is underway, and vice versa.

Figure 20:
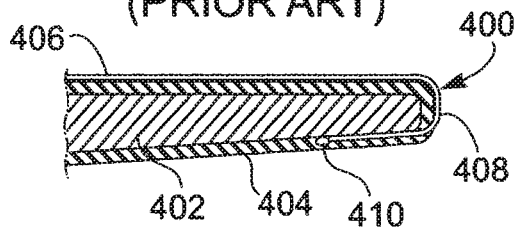
FIG. 20 illustrates a longitudinal cross-section of a "hot" jaw of the prior art.

As mentioned above, the present invention provides a number of solutions to reduce heat loss to the jaws and thus make them more efficient for tissue welding, including modifying the arrangement of the heating element, inner jaw, and silicone boot. FIG. 20 illustrates a conventional longitudinal cross-section of a "hot" jaw 400 having an inner jaw 402 surrounded by a silicone boot 404. A heating element 406 is shown extending along an upper or clamping face of the jaw 400. The heating element 406 extends around a distal end of the jaw 400 at 408, passes through an aperture formed in the boot 404, and electrically communicates with the inner jaw 402 at a solder point or resistance weld 410, for example. The inner jaw 402 is made of stainless steel and provides a return current path for the electricity passing through the heating element 406. With this configuration, a significant amount of heat is stored by the inner jaw 402, with heat loss exacerbated by the physical connection between the heating element and the inner jaw.

FIGS. 21A-21E illustrate a number of alternative jaw cross-sections that reduce the amount of heat lost to the inner jaw, typically stainless steel. It should be understood that certain of these variations may not be mutually exclusive, and can be combined into numerous permutations within the scope of the present invention.

Figure 21A:
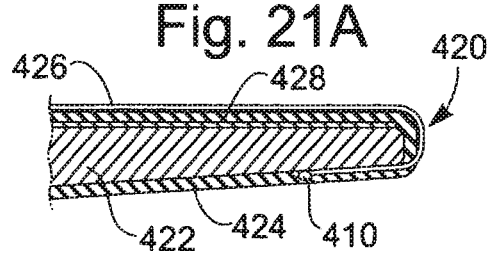
FIGS. 21A-21E illustrate a number of alternative jaw cross-sections that reduce the amount of heat lost to the inner jaw.

In FIG. 21A, a "hot" jaw 420 is constructed much like the jaw 400 of the prior art with an inner jaw 422 of stainless steel, a silicone boot 424, and a heating element 426 that extends along the jaw and wraps around the distal end to be resistance welded to the underside of the inner jaw. Again, the inner jaw 422 provides a return current path. To reduce the amount of heat lost to the inner jaw 422, the inner jaw has a coating 428 on its upper surface of a thermally-insulating material having significantly lower thermal conductivity than stainless steel (17.9 Watts per meter-Kelvin: W/m-K), and preferably less than about 5.0 W/m-K. For example, a ceramic zirconia-based coating having a thermal conductivity of about 1.675 W/m-K may be used. In this way, a thermally insulating barrier extends along the majority of the heat generating portion of the heating element 426, thus impeding conductive heat flow to the inner jaw 422.

Figure 21B:
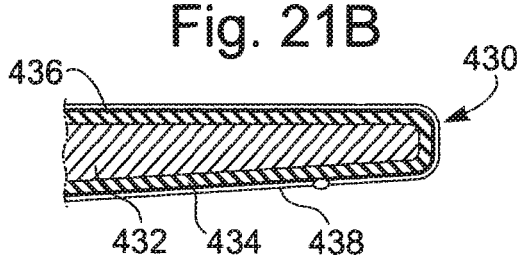

An alternative jaw 430 in FIG. 21B comprises an inner stainless steel jaw 432, a silicone boot 434 therearound, and a heating element 436 on its upper surface. Instead of using the inner jaw 432 as a return current path, the heating element 436 wraps around the distal end of the jaw 430 and connects to a conductive wire 438, for example, which physically decouples the heating element 436 from the inner jaw 432. The heating element 436 and wire 438 may be connected through a solder point or other similar expedient. In an exemplary combination, the jaw 430 shown in FIG. 21B may be supplemented by a ceramic coating such as that shown at 428 in FIG. 21A to further reduce heat loss to the inner jaw 432.

Figure 21C:
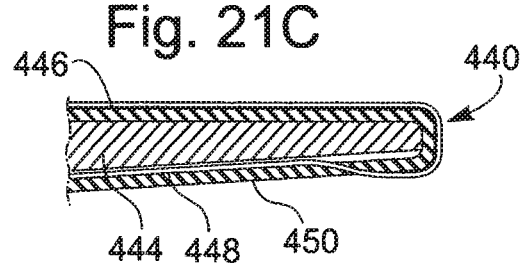
Figure 21D:
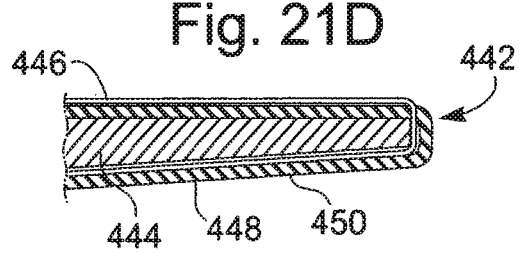

FIGS. 21C and 21D illustrate, respectively, similar jaws 440, 442 in which the inner jaws 444 are again not used as a current return path. The inner jaws 444 could be stainless steel, or a ceramic to reduce the potential for heat loss thereto. The heating elements 446 both connect to wires 448 extending proximally through a space between the inner jaws 444 and the surrounding boots 450. If the jaws 444 are stainless steel, then the wires 448 are insulated such that there is no electrical contact therebetween. The difference between the jaws 440, 442 and the jaw 430 in FIG. 21B is that the wires 448 are concealed underneath the boot 450, as opposed to extending along the outside of the boot. To help prevent tearing of the typically silicone boot 450, the heating elements 446 extends into apertures that are not at the distal tip of the jaws 440, 442. In FIG. 21C, the aperture is on the underside of the jaw 440, while in FIG. 21D the aperture is on the upper face of the jaw 442.

Figure 21E:
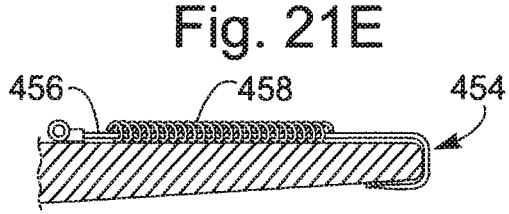

FIG. 21E illustrates a still further alternative jaw 454 that improves over the prior art jaw designs by improving the rate of transfer of heat to the tissue from a heating element 456. Specifically, a coil spring 458 is placed around the heating element 456 to help transfer heat more quickly to the tissue. Desirably, a very close-loop coil should be used to prevent tissue buildup between cycles, and may be coated with a nonstick media such as silicone to further help prevent tissue buildup. The spring 458 may be attached mechanically to the heating element 456 such as with a ceramic material to prevent an electrical short-circuit. Further, the coil spring 458 desirably has approximately the same electrical resistance as the material of the heating element 456 so that the magnitude of power applied to the heating element need not be significantly increased.

Figure 22A:
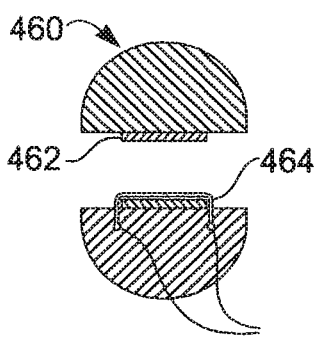
FIGS. 22A and 22B schematically illustrate two different sets of jaws having tissue clamping plates thereon and either a single or dual heating elements electrically connected in parallel.
Figure 22B:
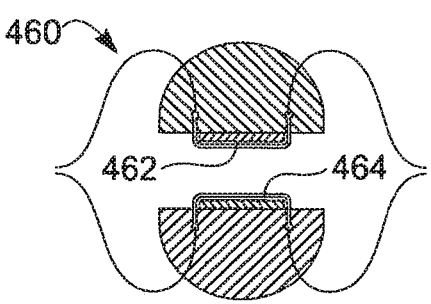

FIGS. 22A and 22B schematically illustrate two different sets of jaws 460 having tissue clamping plates 462 thereon and either a single or dual, heating elements 464 electrically connected in parallel. FIGS. 22A and 22B represent jaw configurations for a variety of different materials and combinations, including heaters on one or both sides of the tissue and various materials used to clamp the tissue. For example, ceramic jaws 460 (e.g., Macor) may be used.

Figure 23:
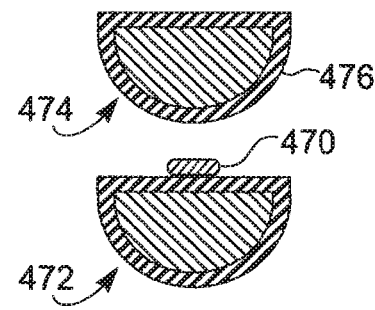
FIG. 23 illustrates another sample test set up with a single heater on a lower jaw and no heater on an upper jaw.

FIG. 23 illustrates another configuration wherein a single heater 470 is provided on a lower jaw 472 while an upper jaw 474 has no heater, but both include surrounding boots that help promote tissue release. The upper jaw 474 is reversed such that the rounded surface 476 of the boot faces the first jaw 472. This configuration may help promote tissue release from the boots.

Jaws with Passive Welding Segments

In most of the earlier-described embodiments, multiple heaters are used, with at least one that performs a cutting function and one that performs a welding function. The present invention also contemplates providing a single heating element that performs both these functions, such as the embodiment seen in FIG. 19D. In addition, the present invention encompasses jaws that include a single heating element for cutting tissue in conjunction with a passive region surrounding the heating element that coincidentally also heats up and provides a tissue welding area. Essentially, these designs are intended to better control heat application and temperature distribution within the tissue during thermal welding in order to achieve a wider weld band, a more consistent weld bandwidth, a thinner cut band with respect to the weld band, and/or decreased or more consistent weld times.

FIGS. 24A-24C illustrate three different alternative embodiments of tissue welding jaws that incorporate a material within the boots and adjacent to the heating element that provide a "hot zone" for welding. More specifically, each of these jaw designs includes a hot jaw 480 shown spaced from a cold jaw 482. Both the hot jaw 480 and the cold jaw 42 include inner jaws surrounded by boots, as has been described. Directly, the cross-sectional shape of the jaws 480, 482 is semi-cylindrical with a flat jaw-facing surface and a rounded outer surface. Each of the hot jaws 480 is provided with a heating element 484 centrally located and longitudinally disposed on the flat jaw-facing surface of each boot.

In FIG. 24A, a strip of thermally conductive material 486 extends underneath the heating element 484 and forms a continuation of the boot (i.e., has a similar thickness as the boot). In FIG. 24B, a strip of thermally conductive material 488 likewise runs co-extensively under the heating element 484. In contrast to the strip 486 in FIG. 24A, the strip 488 of FIG. 24B is somewhat thinner and resides in an inset of the boot. Finally, the hot jaw 480 of FIG. 24C includes a strip of thermally conductive material 490 that is embedded within the boot, as can be achieved by various molding techniques. Each of these strips 486, 488, 490 absorbs some of the heat generated by the heating element 484 and more quickly spreads heat to tissue within a "hot zone" defined between the jaws and within the width of the respective strips. The strips 486, 488, 490 may be made of a suitable metal such as, for example, stainless steel. This hot zone forms a seal in the tissue and eventually the heating element 484 reaches a temperature that severs the tissue within the hot zone. The rate of temperature increase and material selected are such that the tissue is welded across the width of each of these strips 486, 488, 490 prior to the tissue being severed by the heating element 484. In a variation on these embodiments, both boots on the hot jaw 480 and cold jaw 482 may be provided with the strips of thermally conductive material to further enhance heating of the tissue within the hot zone.

Multiple Heating Elements and Staged Heating

FIG. 25 illustrates a still further alternative embodiment of the present invention in which multiple heating elements are used. A hot jaw 492 is shown spaced from a cold jaw 494. The hot jaw 492 includes an electrically conductive first heating element 495 having a semi-annular configuration and a rod-like second heating element 496. A semi-annular layer of insulation 497 is interposed between the first and second heating elements which are concentrically arranged. After tissue has been clamped between the jaws 492, 494, the first heating element 495 is energized such that its temperature reaches a weld zone and forms a weld band in the tissue. After a predetermined amount of time, current is run through the second heating element 496 which heats up to a higher temperature through either higher current or higher resistance, wherein the tissue is severed in the middle of the weld band.

In a slight variation on previously described embodiments, the second heating element 496 may have a wire diameter that increases from a proximal end of the jaw to the distal end. In this way, a constant temperature along the jaw is maintained because more heat is lost from the distal end. Those of skill in the art will understand that there are other ways to ensure a constant temperature along the length of the jaw, such as by varying the materials and/or resistance of the heating element 496.

Fasciotomy Cutters Incorporated into Tissue Welding Jaws

In addition to being able to weld and sever tissue, tissue welders of the present invention may also be capable of performing fasciotomy, or an incision through facia or layers of tissue. This is particularly advantageous when the tissue welder is used in an vessel harvesting operation in which various layers of facia surround the target vessel. A tissue welder that incorporates a fasciotomy cutter allows for rapid, continuous transection of tissue and vessels, typically under visualization with an endoscope.

FIGS. 26A and 26B are schematic views of an exemplary tissue welder having a fasciotomy cutter. A hot jaw 500 and a cold jaw 502 are schematically illustrated on the right side, open in FIG. 26A and closed in FIG. 26B a heating element 504 is provided on the jaw-facing surface of the hot jaw 500 and may take form of any of the various embodiments described herein. In addition, a cutting element 506 is located at the apex of the jaws 500, 502, approximately perpendicular to the heating element 504. Both the heating element 504 and cutting element 506 are connected to a power supply as shown and wired in parallel to an interlock switch 508. When the jaws 500, 502 are open and the device is activated by the user, current is routed through the cutting element 506. Conversely, when the jaws are closed and the device is activated by the user, current is routed to the welding element 504. The user could have control of both the activation switch and the interlock switch 508, or the interlock switch could be mechanically linked to the position of the jaws.

Figure 27:
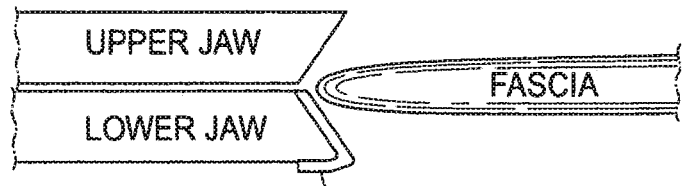
FIG. 27 is a side elevational view of the distal tips of upper and lower jaws having a fasciotomy heater wire on a leading edge and angled toward one another such that when the jaws are closed they guide the facia toward the heater wire.

A variation on the fasciotomy cutter shown in FIGS. 26A-26B is to place a fasciotomy heater wire 510 on the distal end of one of the jaws as seen in FIG. 27. A similar arrangement was shown previously in FIG. 19B, though the fasciotomy wire 510 may form a series extension of the welding element, or may be a separately activated heating element as in FIGS. 26A-26B. The distal tips of the upper and lower jaws in FIG. 27 are angled in a proximal direction toward one another such that when the jaws are closed they guide the facia toward the heater wire 510.

Figure 28:
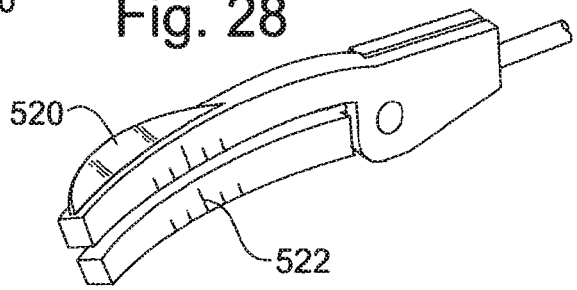
FIG. 28 illustrates a pair of tissue welding jaws having a fasciotomy cutter comprising a knife edge or blade longitudinally disposed on a midline of an outer surface of one of the jaws.

FIG. 28 illustrates a still further fasciotomy cutter 520 on a pair of tissue welding jaws. In this case the cutter 520 comprises a knife edge or blade longitudinally disposed on a midline of an outer surface of one of the jaws. The blade 520 could be retractable such that the user only extends it when fasciotomy is desired. Further, the knife blade 520 could be resistively heated such that it more easily slices through facia.

FIG. 28 illustrates a still further alternative aspect of the present invention wherein indicator markings 522 are placed on the side of one or both of the jaws. The indicator markings 522 could be placed in millimeters increments so that adjustments in power setting and weld time can be made to account for varying vessel sizes. Preferably, a centering marker larger than the others is provided as shown such that the user can optimally center a vessel within the jaws.

Control of Temperature Increase

Figure 29:
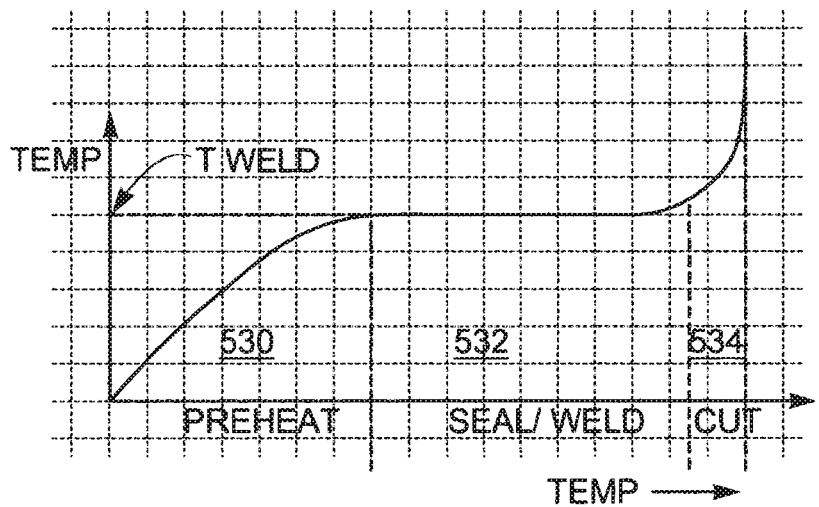
FIG. 29 is a graph of the temperature of a tissue welder heating element over time.

Current tissue welders utilize a constant DC current to drive the heating elements. Therefore, the power delivered to the heater is constant ($P=I^2 \cdot R$). A typical graph of the temperature of the heating element over time is shown in FIG. 29. After switching current on, there is a preheat phase 530 in which time the heating element's temperature increases to the weld temperature. After that, there is a period of time 532 when the tissue is sealed or welded. Finally, the heating element temperature increases further at 534 to cut the tissue. The time necessary for the preheat stage 530 is essentially wasted, and slows down the overall operation when a number of welding steps are required. Increasing the current during the preheat stage 530 would shorten this time, but might cause the temperature to overshoot the weld temperature and perhaps form charring. Such overshoot might also cause the tissue to be severed before being probably sealed.

Figure 30:
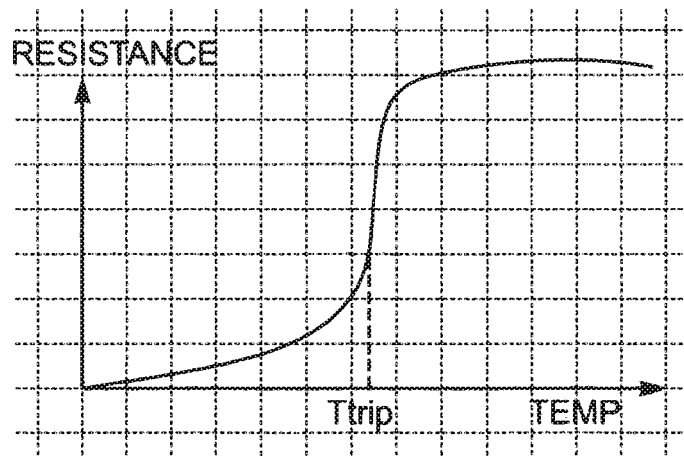
FIG. 30 is a curve of the electrical resistance of a Polymer Positive Temperature Coefficient (PPTC) device versus temperature.
Figure 31A:
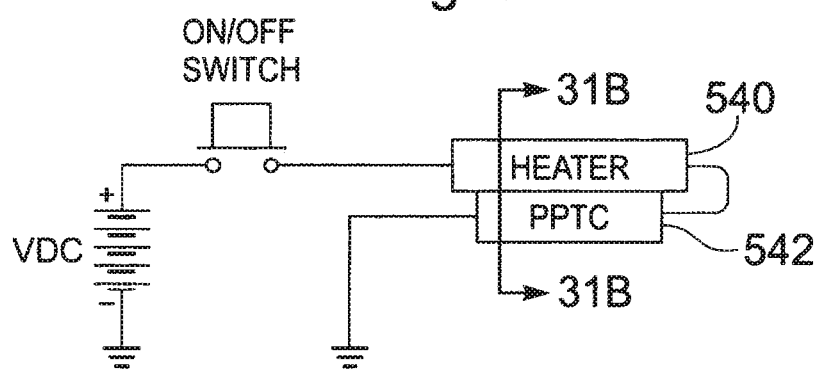
FIGS. 31A and 31B schematically illustrate a circuit having a heating element and a PPTC device electrically connected in series therewith.
Figure 31B:

One solution to this issue is to place a Polymer Positive Temperature Coefficient (PPTC) device, which has a resistance that varies as in the curve of FIG. 30, in series electrically with the heating element. These devices exhibit a rapid increase in their resistance at their trip temperature. FIGS. 31A and 31B schematically illustrate a circuit having a heating element 540 that represents any of the heating elements described herein. The circuit loops through the heater 540 and through a PPTC device 542 electrically connected in series therewith. Through the choice of the PPTC material, the temperature at which the material becomes highly resistive equals the weld temperature. This allows the material to be used as a temperature control switch that regulates the temperature of the heating element 540 by acting as a closed switch below the weld temperature, and as an open switch above the weld temperature. Therefore, a higher current can be used to raise the temperature of the heating element 540 more rapidly and reduce the preheat time, but the PPTC element 542 prevents overshoot of the temperature.

Figure 32A:
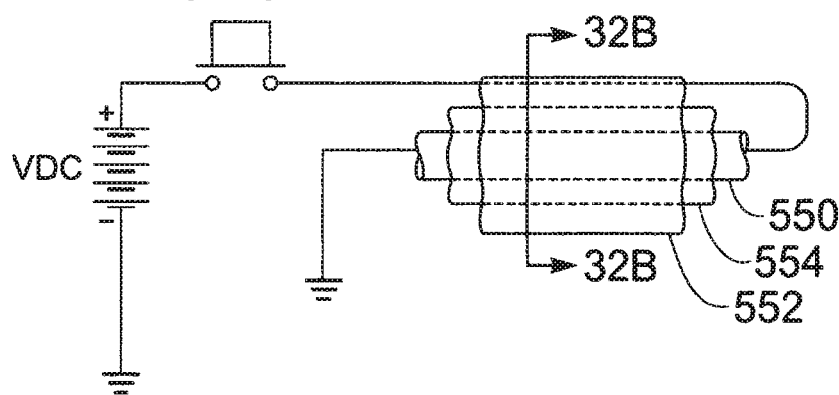
FIGS. 32A and 32B illustrate a rod-like PPTC element concentrically arranged within an outer tubular heating element with a tubular layer of electrical insulation therebetween.
Figure 32B:
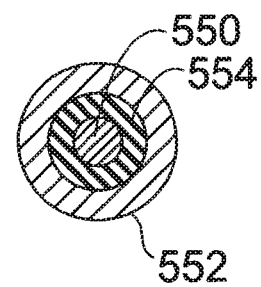

An alternative configuration of the use of PPTC material is seen in FIGS. 32A and 32B. In this version, a rod-like PPTC element 550 resides concentrically within an outer tubular heating element 552 with a tubular layer of electrical insulation 554 therebetween. This configuration of heating element 552 more closely resembles the earlier-illustrated tubular embodiments. The circuit passes through the outer heating element 552 and back through the centrally located PPTC element 550. The insulation around the rod-like PPTC element 550 must have a high resistivity to block DC current, but should be thin enough to allow good heat transfer between the heater and the PPTC material. In this way, even or monolithic heating of the entire assembly is not unduly hindered.

In an alternative embodiment not specifically illustrated, any of the heating elements disclosed herein may be constructed of a Positive Temperature Coefficient of Resistance (PTCR) material whose electrical resistance is not constant over a predetermined temperature range including the weld temperature, and typically exhibits a generally linear relationship between electrical resistance and temperature (i.e., higher resistance at higher temperatures). This allows for rapid initial rate of temperature increase, so that the heating element rapidly approaches the desired welding temperature. As the temperature approaches the weld temperature, the rate of increase slows down due to the increased resistance of the PTCR element. This prevents the heating element from overshooting the desired temperature, and potentially prematurely transecting the tissue or vessel. Advantageously, the rapid initial rate of temperature increase reduces the overall welding time. Instead of using PTCR as the heating element itself, an alternative is to place a PTCR element in series with the heating element, much like is shown in FIGS. 31 and 32 with respect to PPTC elements. As the PTCR element is heated from the applied current, the total resistance of the circuit increases resulting in less current through the heating element and a similar temperature governing effect.

In prior art systems, the constant current delivered to the heater is set by using a control knob on the power supply. If the current is set high to rapidly increase the heater temperature, an inadequate weld may result. Conversely, if the current is set low, the weld times may be too long. Furthermore, a current setting that is optimal for a given size vessel may be inadequate for different vessel diameter.

Figure 33A:
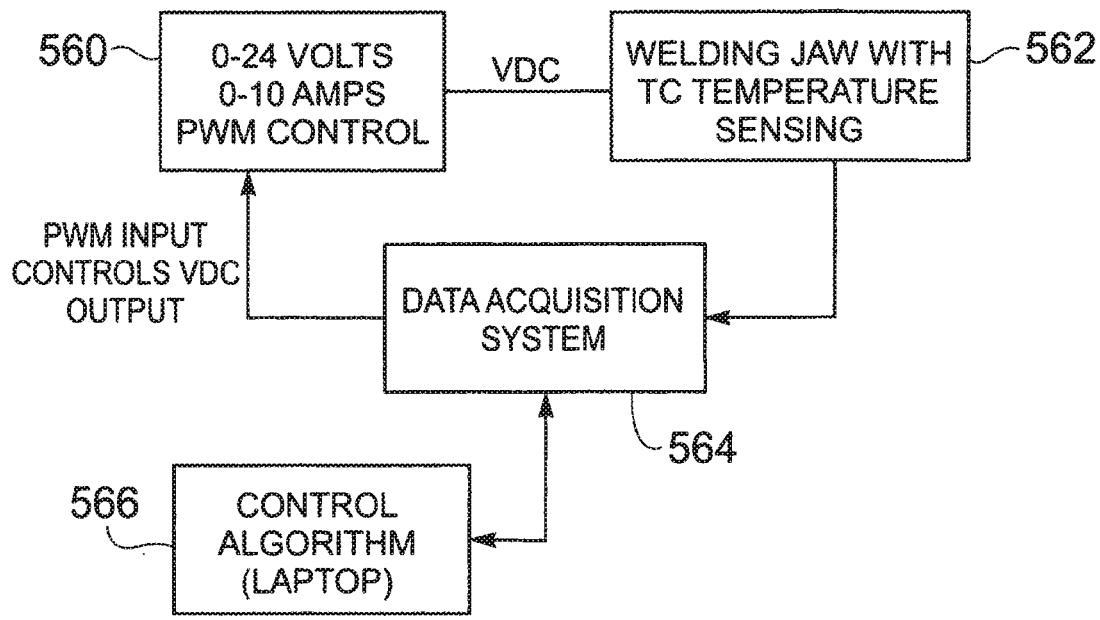
FIGS. 33A-33C illustrate a system which actively monitors and controls the temperature of tissue within the jaws of the thermal tissue welding device of the present invention.
Figure 33B:
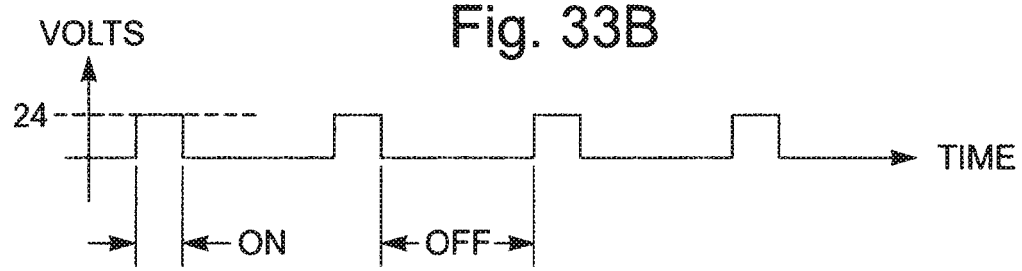
Figure 33C:
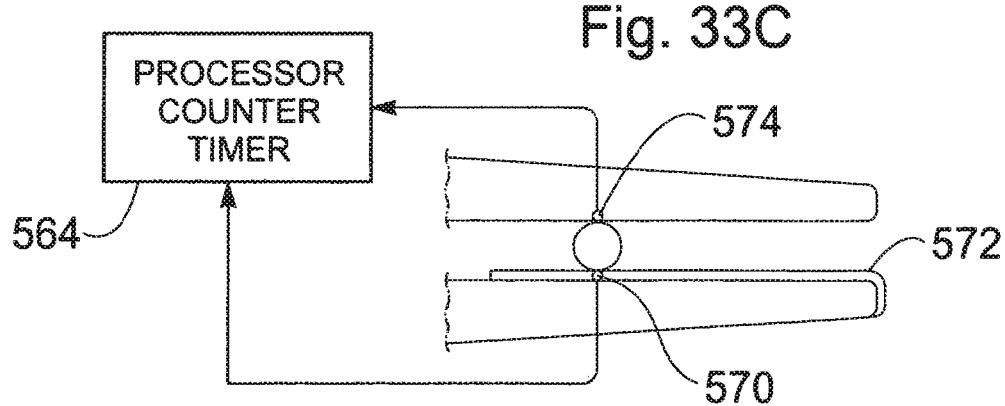

One methodology for closely controlling the temperature of the heating element in any of the embodiments described above is to utilize temperature sensing and feedback through a processor, as seen in FIGS. 33A-33C More specifically, FIG. 33A illustrates a system which actively monitors and controls the temperature of tissue within the jaws of the thermal tissue welding device. The system comprises a controllable DC power supply 560, tissue welding jaws with temperature sensing capacity 562, a processor having a data acquisition system 564, and a control algorithm 566 such as within a laptop interfaced with the processor. The power supply 560 desirably provides 100 W DC, and its output may be varied from 0-24 VDC using a pulse width modulated (PWM) input control signal (FIG. 33B), where the duty cycle of the PWM input signal determines the level of the DC voltage output (i.e., $V_{out}=24$ (1-duty cycle)). Input for the power supply 560 is received from the data acquisition system 564, and the power supply output is connected to the heater of the tissue welding device.

In an exemplary configuration as seen in FIG. 33C, one of the tissue welding jaws has a thermocouple 570 placed in thermal contact with the center of the heating element 572.

A second thermocouple 574 may also be provided in the opposing jaw for measuring the tissue temperature. These thermocouples are connected to the inputs of the processor/data acquisition system 564. As the jaws are heated, the processor/data acquisition system 564 collects temperature data and translates it to the control algorithm 566. In a prototypical version, a Proportional Integral Derivative (PID) control algorithm is implemented in Visual Basic on a laptop for controlling the power supply output voltage. In a commercial design, the laptop and data acquisition functions will be implemented in the power supply using a microcomputer and A/D and CJC chips, and the algorithm will be written in C or C++.

The advantages of the active feedback system as seen in FIG. 33A include the ability to maintain optimal temperatures for sealing and cutting regardless of tissue type or geometry. Furthermore, the ability to automatically adjust power delivered to the heating element to minimize the initial preheat time, followed by a lower power setting to form the weld reduces the overall operation time. Moreover the system automatically adjusts for different vessel diameters. Furthermore, the temperature waveform may be used to determine the endpoint, or completion of the weld. The current method of waiting until severed vessels dropped from the jaws may result in longer than necessary weld times and unnecessary sticking and charring.

Tissue Welder with Resistance Welding Capability

During certain procedures such as vessel harvesting, devices of the present invention may inadvertently cause avulsion of incident vessels. More generally, blunt dissection, mechanical cutting of surrounding tissue, or incomplete tissue welding or other cautery may result in bleeding within the internal cavity. The present invention also encompasses supplemental heaters which may be used to stop such bleeding by creating "spot welds," or localized areas of cauterized tissue by resistive heating of the tissue.

For example, FIGS. 34A, 34B, 35A, 35B, 36A, 36B, and 37 illustrate a number of designs of tissue welder jaws having localized heaters or welders on the distal end of one of the jaws. In general, the surface area per length of each of the resistance welders is larger than the surface area per length of the associated heating element for welding tissue so that a wider distribution of heat can be applied at that point.

FIGS. 34A-34B illustrate a set of jaws 580, including a hot jaw 581 which has a heating element 582 (i.e., for welding and/or severing) on its inside or jaw-facing surface, as described above. A separate circuit energizes a flat ribbon heater 584 on the distal tip of the hot jaw 581 for resistance welding. The separate activation circuit helps prevent thermal damage to the heating element 582 which otherwise would be activated along with the ribbon heater 584. Further, the separate circuit has user controls by clearly differentiating between tissue welding and resistance welding.

FIGS. 35A-35B illustrate a set of jaws 590, including a hot jaw 591 which has a heating element 592. A flat ribbon heater 594 is provided on the distal tip of the hot jaw 591 and is connected in series with the heating element 592. The ribbon heater 594 increases the surface area of the heating element 592 in contrast with a straight wire.

FIGS. 36A-36B illustrate a set of jaws 600, including a hot jaw 601 which has a heating element 602 on its inside face. The distal end of the hot jaw 601 includes a shaped wireform heater 604 connected in series with the heating element 602 which provides the ability to cauterize small areas of tissue in contact with the distal jaw tip when the heating element is activated. The serpentine band pattern of the heater 604 increases the length of exposed heater wire on the distal face of the jaw 601, and thus increases the amount of energy that can be delivered to the tissue from the surface in contrast with a portion of straight wire as is seen in earlier embodiments.

Finally, FIG. 37 illustrates a still further set of tissue welding jaws 610 including a hot jaw 611 having a heating element 612 thereon. Instead of the heating element 612 terminating at the distal tip of the jaw 611, it extends farther around the outside of the jaw and includes a widened pad 614 for resistance welding. Because the pad 614 or flat electrode is exposed on the outside of the jaw, it can be more easily positioned against the target tissue. A source of power and a separate foot switch 616 for activating one or both of the circuits is shown.

In an alternative arrangement not specifically illustrated, a monopolar RF welder may be implemented using any of the previously described configurations. More particularly, the tissue welding device may be disconnected from the DC power supply and connect to an RF power source (such as a bovie unit) prior to resistance welding. The existing heating element circuit delivers the RF energy to the tissue, and the return path is through the patient's grounding path. Alternatively, both DC and RF power sources may be connected to the device, and a separate control allows the user to switch between the two as desired.

It will also be appreciated by those of skill in the relevant art that various modifications or changes may be made to the examples and embodiments described without departing from the intended scope of the invention. In this regard, the particular embodiments of the invention described herein are to be understood as examples of the broader inventive concept disclosed.

What is claimed is:

1. A surgical apparatus for welding and severing tissue comprising:
    an elongated shaft;
    a first jaw and a second jaw, wherein the second jaw is relatively movable with respect to the first jaw, wherein the first jaw and the second jaw extend from a distal end of the shaft and each of the first jaw and the second jaw comprises a jaw-facing surface;
    a first heating assembly configured to weld tissue, sever tissue, or both weld and sever tissue, wherein the first heating assembly is a component of one jaw of the first and second jaws; and
    a second heating assembly configured to spot weld tissue, wherein the second heating assembly is a component of the same jaw as the first heating assembly; and
    a control assembly operably connected to activate the first heating assembly and the second heating assembly.

2. The surgical apparatus of claim 1, wherein the first heating assembly includes a heating element actuatable by the control assembly to generate heat for welding tissue, severing tissue, or welding and severing tissue.

3. The surgical apparatus of claim 2, wherein the heating element is disposed, at least in part, on the jaw-facing surface of the one jaw of the first and second jaws.

4. The surgical apparatus of claim 2, wherein the second heating assembly comprises a first ribbon heater.

5. The surgical apparatus of claim 4, wherein the control assembly comprises a first activation circuit that energizes the heating element and a separate second activation circuit that energizes the ribbon heater.

6. The surgical apparatus of claim 5, wherein the second heating assembly comprises a second ribbon heater and the heating element of the first heating assembly is disposed between the first ribbon heater and the second ribbon heater.

7. The surgical apparatus of claim 1, wherein the second heating assembly includes a heater actuatable by the control assembly to generate heat for resistance welding of tissue.

8. The surgical apparatus of claim 7, wherein the heater is disposed on a surface of a distal tip of the one jaw, wherein the surface of the distal tip of the one jaw constitutes a substantially different surface from the jaw-facing surface of the one jaw.

9. The surgical apparatus of claim 8, wherein the surface of the distal tip intersects substantially orthogonally with the jaw-facing surface of the one jaw and the heater comprises a ribbon heater.

10. The surgical apparatus of claim 8, wherein the surface of the distal tip intersects substantially orthogonally with the jaw-facing surface of the one jaw and the heater comprises a shaped wireform heater provided with a serpentine band pattern.

11. The surgical apparatus of claim 7, wherein the heater is disposed on an outside surface of the one jaw, wherein the outside surface of the one jaw constitutes a substantially different surface from the jaw-facing surface of the one jaw and the heater comprises a widened pad electrode configured for resistance heating.

12. The surgical apparatus of claim 1, wherein the control assembly comprises a first circuit connected to energize the first heating assembly and a second circuit connected to energize the second heating assembly, wherein the control assembly is configured to energize only one of the first heating assembly and the second heating assembly at a time.

13. A surgical apparatus for welding and severing tissue comprising:
an elongated shaft;
a first jaw and a second jaw, wherein the second jaw is relatively movable with respect to the first jaw, wherein the first jaw and the second jaw extend from a distal end of the shaft and each of the first jaw and the second jaw comprises a jaw-facing surface;
a first heating assembly configured to weld tissue, sever tissue, or both weld and sever tissue, wherein the first heating assembly is a component of one jaw of the first and second jaws, and wherein the first heating assembly includes a heating element; and
a second heating assembly configured to spot weld tissue, wherein the second heating assembly is a component of the same jaw as the first heating assembly, and wherein the second heating assembly includes a heater actuatable by a control assembly to generate heat for resistance welding of tissue; and
the control assembly is operably connected to activate the first heating assembly and the second heating assembly, wherein the control assembly is operable to energize the heating element for welding tissue, or for severing tissue, or for both welding and severing tissue, and the control assembly is operable to energize the heater to generate heat for resistance welding of tissue.

14. The surgical apparatus of claim 13, wherein the control assembly is configured to energize only one of the first heating assembly and the second heating assembly at a time.

* * * * *